United States Patent
Chapoux et al.

(10) Patent No.: US 9,796,686 B2
(45) Date of Patent: Oct. 24, 2017

(54) ANTIBACTERIAL QUINAZOLINE-4(3H)-ONE DERIVATIVES

(71) Applicant: IDORSIA PHARMACEUTICALS LTD, Allschwil (CH)

(72) Inventors: Gaëlle Chapoux, Allschwil (CH); Jean-Christophe Gauvin, Allschwil (CH); Azely Mirre, Allschwil (CH); Jean-Philippe Surivet, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/311,758

(22) PCT Filed: May 13, 2015

(86) PCT No.: PCT/EP2015/060653
§ 371 (c)(1),
(2) Date: Nov. 16, 2016

(87) PCT Pub. No.: WO2015/173329
PCT Pub. Date: Nov. 19, 2015

(65) Prior Publication Data
US 2017/0081292 A1 Mar. 23, 2017

(30) Foreign Application Priority Data
May 16, 2014 (EP) .................................. 14168718

(51) Int. Cl.
*C07D 239/90* (2006.01)
*A61K 31/517* (2006.01)
*C07D 405/06* (2006.01)

(52) U.S. Cl.
CPC .......... *C07D 239/90* (2013.01); *A61K 31/517* (2013.01); *C07D 405/06* (2013.01)

(58) Field of Classification Search
CPC .................................................. C07D 239/90
See application file for complete search history.

(56) References Cited

FOREIGN PATENT DOCUMENTS

| WO | WO 98/38163 A1 | 9/1998 |
|---|---|---|
| WO | WO 03/077914 A2 | 9/2003 |
| WO | WO 2010/024356 A1 | 3/2010 |
| WO | WO 2010/037210 A1 | 4/2010 |
| WO | WO 2010/060785 A1 | 6/2010 |
| WO | WO 2010/135536 A2 | 11/2010 |
| WO | WO 2011/045703 A2 | 4/2011 |
| WO | WO 2011/073845 A1 | 6/2011 |
| WO | WO 2012/154204 A1 | 11/2011 |
| WO | WO 2012/054332 A1 | 4/2012 |
| WO | WO 2012/093809 A2 | 7/2012 |
| WO | WO 2012/120397 A1 | 9/2012 |
| WO | WO 2012/137094 A1 | 10/2012 |
| WO | WO 2012/137099 A1 | 10/2012 |
| WO | WO 2012/170845 A2 | 12/2012 |

(Continued)

OTHER PUBLICATIONS

International Search Report and Written Opinion issued in PCT/IB2015/058919 dated Jan. 28, 2016.
U.S. Appl. No. 15/528,407, Gaelle Chapoux, Antibacterial Benzothiazole Derivatives, filed May 19, 2017.
"Methods for Dilution Antimicrobial Susceptibility Tests for Bacteria That Grow Aerobically," Approved Standard 7th ed., Clinical and Laboratory Standards Institute (CLSI) Document M7-A7, pp. 1-64 (2006).
Bellina et al., "Palladium Catalysts for the Suzuki Cross-Coupling Reaction: An Overview of Recent Advances," Synthesis, 2004, pp. 2419-2440.
Benz, Synthesis of Amides and Related Compounds, New York (1991), pp. 381-417.
Brown et al., "Potent Inhibitors of LpxC for the Treatment of Gram-Negative Infections," J. of Medical Chemistry, 2012, vol. 55, pp. 914-923.

(Continued)

*Primary Examiner* — Paul V Ward
(74) *Attorney, Agent, or Firm* — Arent Fox LLP

(57) ABSTRACT

The invention relates to antibacterial compounds of formula I

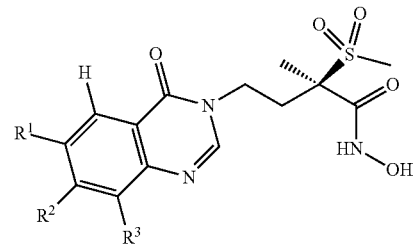

wherein $R^1$ is H or halogen; $R^2$ is the group M; $R^3$ is H or halogen; M is $M^A$ or $M^B$

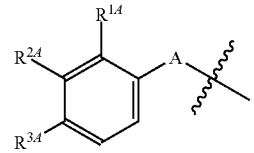

$M^A$

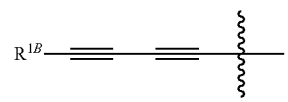

$M^B$ wherein A is a bond or C≡C; $R^{1A}$ is H or halogen; $R^{2A}$ is H, alkoxy or halogen; $R^{3A}$ is H, alkoxy, hydroxyalkoxy, hydroxyalkyl, 1,2-dihydroxyethyl, dialkylamino, 1-hydroxymethyl-cycloprop-1-yl, 1-((dimethylglycyl)oxy)methyl-cycloprop-1-yl, 3-hydroxyoxetan-3-yl, morpholin-4-ylalkyl or morpholin-4-ylalkoxy; and $R^{1B}$ is a group as defined in claim 1;
and salts thereof.

15 Claims, No Drawings

(56) References Cited

FOREIGN PATENT DOCUMENTS

| WO | WO 2013/170030 A1 | 11/2013 |
|---|---|---|
| WO | WO 2013/170165 A1 | 11/2013 |
| WO | WO 2015/024010 A2 | 2/2015 |
| WO | WO 2015/036964 A1 | 3/2015 |
| WO | WO 2015/091741 A1 | 6/2015 |
| WO | WO 2015/132228 A1 | 9/2015 |

OTHER PUBLICATIONS

Chodkiewicz et al., C.R. Hebd. Seances Acad. Sci. (1955), vol. 241, pp. 1055-1057.
Crossley et al., "An Alkynyliodide Cycloaddition Strategy for the Construction of Iodoisoxazoles," J. Org. Chem., vol. 75, 2010, pp. 5414-5416.
El-Zohry et al., "Synthesis of Some New 3-(2'-Heterocyclicethyl)-2-methyl-3,4-dihydroquinazolin-4-one Derivatives as Antimicrobial Agents," J. Chem. Tech. Biotechnol. vol. 55, pp. 209-215.
Fu, "The Development of Versatile Methods for Palladium-Catalyzed Coupling Reactions of Aryl Electrophiles through the Use of P(t-BU3) and PCY3 as Ligands," Accounts of Chem. Res. vol. 41, Nov. 2008, pp. 1555-1564.
International Search Report issued in International Patent Application No. PCT/EP2015/060653 dated Jul. 1, 2015.
Kantchev et al., "Pd-N-Heterocyclic Carbene (NHC) Catalysts for Cross-Coupling Reactions," Aldrichimica ACTA, vol. 39, 2006, pp. 97-111.
Larock, "Comprehensive Organic Transformations, A guide to Functional Group Preparations," 2nd Edition (1999), Section Nitriles, carboxylic acids and derivatives, pp. 1941-1949.
Lin et al., "Inhibition of LpxC Protects Mice from Resistant Acinetobacter baumannil by Modulating Inflammation and Enhancing Phagocytosis," mBio, vol. 3, 2012, pp. 1-10.
Marmer et al., "The Preparation and Reactions of Novel 0-Acylhydroxlamines," J. Org. Chem., vol. 37, 1972, pp. 3520-3523.
Mauger et al., "Synthetic Applications of Buchwald's Phosphines in Palladium-Catalyzed Aromatic-Bond-Forming Reactions," Aldrichimal ACTA., vol. 39, 2006, pp. 17-24.
McAllister et al., "Heterocyclic methylsulfone hydroxamic acid LpxC Inhibitors as Gram-negative antibacterial agents," Bioorganic & Medicinal Chemstry Letters, vol. 22, 2012, pp. 6832-6838.
Miyaura et al., "Palladium-Catalyzed Cross-Coupling Reactions of Organoboron Compounds," Chem. Rev. vol. 95, 1995, pp. 2457-2483.
Mohapatra et al, "The first asymmetric total synthesis of 3((1R,2R)- and 3((1S,2R)-2-(12-methyltridecyl)cyclopropy)propanoic acid," Tetrahedron Letters, vol. 53, 2012, pp. 6718-6720.
Montogomerry et al., "Pyridone Methylsulfone Hydroxamate LpxC Inhibitors for the Treatment of Serious Gram-Negative Infections," J. Med. Chem., vol. 55, 2012, pp. 1661-1670.
Oddo et al., "Design annd steroselective synthesis of C-aryl furanoside as a comformationally constrained CHIR-090 analogue," Carbohydrate REsearch, vol. 359, 2012, pp. 59-64.
Reddy et al., "Mild and efficient oxy-iodination of alkynes and phenols with potassium iodide and tert-butyl hydroxperoxide," Tetrahedron Letters, vol. 51, 2010, pp. 2170-2173.
Remington, The Science and Practice of Pharmacy, 21st Edition (2005), Part 5, "Pharmaceutical Manufacturing."
Sakagami et al., Synthesis, in vitro pharmacology, and pharmacokinetic profiles of 2[1-amino-1-carboxy-2-(9H-xanthen-9-yl)-ethyl]-1-fluoro-cyclopropanecarboxylic acid and its 6-heptyl ester, a potent mGluR2 antagonist, Bioorg. Med. Chem. vol. 16, 2008, pp. 4359-4366.
Sanford et al., "The Sanford Guide to Antimicrobial Therapy," 26th Edition, (Antimicrobial Therapy, Inc., 1996), pp. 1-4.
Sleveland et al., "Synthesis of Phenylboronic Acids in Continuous Flow by Means of a Multijet Oscillating Disc Reactor System Operating at Cryogenic Temperatures," Organic Process Research & Development, vol. 16, 2012, pp. 1121-1130.
Smith, III et al., "Spongipyran synthetic studies. Total synthesis of (+)-spongistatin 2," Tetrahedron, vol. 65, 2009, pp. 6470-6488.
Sonogashira, "Cross-coupling Reactions to sp Carbon Atoms," Metal-Catalyzed Reactions, 1998, pp. 203-229.
Stahl et al., "Pharmaceutical Salts Properties, Selection, and Use," 2008, pp. 1-24.
T.W. Greene et al., Protecting Groups in Organic Synthesis, 3rd Ed., 1999, pp. 23-147.
T.W. Greene, P.G.M., WUTS, Protective Groups in Organic Synthesis, 1999, pp. 1-3.
T.W. Greene, P.G.M., WUTS, Protective Groups in Organic Synthesis, 3rd Ed., 1999, pp. 369-441.
Tsuda et al., "Application of Modified Mosher's Method for Primary Alcohols with a Methyl Group at C2 Position," Chem. Pharm. Bull., vol. 51, 2003, pp. 448-451.
U.S. Appl. No. 15/106,790, filed Jun. 20, 2016.
U.S. Appl. No. 15/123,184, filed Sep. 1, 2016.
Wender et al., "Highly Efficient, Facile, Room Temperature Intermolecular [5+2] Cycloadditions Catalyzed by Cationic Rhodim (I): One Step to Cycloheptenes and Their Libraries," Organic Letters, vol. 12, 2010, pp. 1604-1607.
Wouters et al., "Pharmaceutical Salts and Co-crystals," 2012, pp. 1-10.

ANTIBACTERIAL QUINAZOLINE-4(3H)-ONE DERIVATIVES

CROSS REFERENCE TO RELATED APPLICATION

This application is a 35 U.S.C. §371 National Phase of PCT Application No. PCT/EP2015/060653 dated May 13, 2015, which claims priority to European Patent Application No. 14168718.6 dated May 16, 2014. The disclosure of these prior applications are hereby incorporated in their entirety by reference.

The present invention concerns antibacterial quinazoline-4(3H)-one derivatives, pharmaceutical compositions containing them and uses of these compounds in the manufacture of medicaments for the treatment of bacterial infections. These compounds are useful antimicrobial agents effective against a variety of human and veterinary pathogens, especially Gram-negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumonia, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new essential target. In this respect, LpxC, which is an enzyme in the biosynthesis of lipopolysaccharides (a major constituent of the outer membrane of Gram-negative bacteria), has received some attention and several patent applications relating to LpxC inhibitors have been published recently. For example, WO 2011/045703 describes antibacterial compounds of formula (A1)

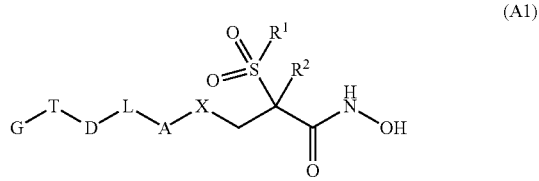

(A1)

wherein $R^1$ is $(C_1$-$C_3)$alkyl; $R^2$ is H or $(C_1$-$C_3)$alkyl; X is $CH_2$, O, NH, S or $SO_2$; A is an optionally substituted phenyl or a 6-membered heteroaryl group; L is absent or is S, SH, OH, $-(CH_2)_p-O-(CH_2)-$, $-(CH_2)_p-O-(CH_2)_z-$ $O-(CH_2)-$, $-S-(CH_2)_z-$ or $-(CH_2)_z-S-$; D is absent or is an optionally substituted group containing a carbocyclic or heterocyclic component with optionally a $(C_1$-$C_3)$alkyl chain appended; T is absent or is $-(CH_2)_z-$, $-(CH_2)_z-O-$ or $-O-(CH_2)_p-C(O)-(CH_2)-$; G is absent or is an optionally substituted carbocyclic or heterocyclic group; and n and p are integers each ranging from 0 to 3 and z is an integer ranging from 1 to 3.

WO 2011/073845 and WO 2012/120397 describe antibacterial compounds with a structural formula similar to formula (A1), whereby the group corresponding to the group A of formula (A1) however respectively represents a pyridin-2-one or a fluoropyridin-2-one residue.

WO 2012/137094 describes antibacterial compounds of formulae (A2) and (A3)

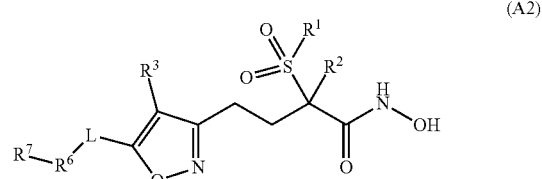

(A2)

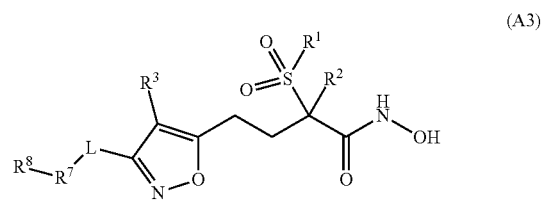

(A3)

wherein $R^1$ is $(C_1$-$C_3)$alkyl; $R^2$ is H or $(C_1$-$C_3)$alkyl; $R^3$ is H, $(C_1$-$C_3)$alkoxy, $(C_1$-$C_3)$alkyl, cyano, $(C_1$-$C_3)$haloalkoxy, $(C_1$-$C_3)$haloalkyl, halogen or hydroxy; L is a bond, $-(CH_2)_n-$, $-(CH_2)_nO(CH_2)_p-$, $-(CH_2)NR^4(CH_2)_p-$, $-(CH_2)SO_2NR^4(CH_2)_p-$, $-(CH_2)CONR^4(CH_2)_p-$ or $-(CH_2)NR^4CO(CH_2)_p-$; $R^4$ and $R^5$ are independently H, $(C_1$-$C_6)$alkyl, $(C_1$-$C_6)$alkylcarbonyl, $(C_3$-$C_8)$cycloalkyl, $(C_3$-$C_8)$cycloalkyl$(C_1$-$C_6)$alkyl or formyl; n is 0, 1, 2, 3 or 4; p is 0, 1, 2, 3 or 4; $R^6$ is $(C_1$-$C_6)$alkoxy$(C_1$-$C_6)$alkyl, $(C_1$-$C_6)$alkoxycarbonyl, $(C_1$-$C_6)$alkyl-$NR^4$—$(C_1$-$C_6)$alkyl, $(C_1$-$C_6)$alkylthio$(C_1$-$C_6)$alkyl, $(C_1$-$C_6)$alkylthiocarbonyl, $(C_6$-$C_{12})$aryl, $(C_6$-$C_{12})$aryloxy, $(C_6$-$C_{12})$arylthio, $(C_6$-$C_{12})$aryl-$NR^4$—, $(C_3$-$C_8)$cycloalkyl, $(C_3$-$C_8)$cycloalkyloxy, $(C_3$-$C_8)$cycloalkylthio, $(C_5$-$C_8)$cycloalkyl-$NR^4$—, $(C_5$-$C_{12})$heteroaryl, $(C_5$-$C_{12})$heteroaryloxy, $(C_5$-$C_{12})$heteroarylthio, $(C_5$-$C_{12})$heteroaryl-$NR^4$—, $(C_3$-$C_{13})$heterocyclyl, $(C_3$-$C_{13})$heterocyclyloxy, $(C_3$-$C_{13})$heterocyclylthio, $(C_3$-$C_{13})$heterocycle-$NR^4$—, hydroxy$(C_1$-$C_{10})$alkyl, mercapto$(C_1$-$C_6)$alkyl, $(NR^4R^5)$alkyl, or $(NR^4R^5)$carbonyl; and $R^7$ is absent or is $(C_6$-$C_{12})$aryl, $(C_6$-$C_{12})$aryl$(C_1$-$C_6)$alkyl, $(C_3$-$C_8)$cycloalkyl, $(C_3$-$C_8)$cycloalkyl$(C_1$-$C_6)$alkyl, $(C_5$-$C_{12})$heteroaryl, $(C_5$-$C_{12})$heteroaryl$(C_1$-$C_6)$alkyl, $(C_3$-$C_{13})$heterocyclyl or $(C_3$-$C_{13})$heterocyclyl$(C_1$-$C_6)$alkyl.

WO 2012/137099 describes antibacterial compounds of formula (A4)

(A4)

wherein $R^1$ is $(C_1-C_3)$alkyl; $R^2$ is H or $(C_1-C_3)$alkyl; $R^3$ is H or $(C_1-C_3)$alkyl; X is N or $CR^4$; Y is N or $CR^4$; $R^4$ is H or $(C_1-C_3)$alkyl; L is a bond, $(C_2-C_6)$alkenylene, $(C_1-C_6)$alkylene, $(C_2-C_6)$alkynylene, —$(CH_2)O(CH_2)_p$—, —$(CH_2)S(CH_2)_p$—, —$(CH_2)NR^5(CH_2)_p$—, —$(CH_2)SO_2NR^5(CH_2)_p$—, —$(CH_2)NR^5SO_2(CH_2)_p$—, —$(CH_2)CONR^5(CH_2)_p$— or —$(CH_2)NR^5CO(CH_2)_p$—; $R^5$ and $R^6$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$-$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_5-C_8)$cycloalkyl-$NR^5$—$(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocyclyl, $(C_3-C_{13})$heterocyclyloxy, $(C_3-C_{13})$heterocyclylthio, $(C_3-C_{13})$heterocyclyl-$NR^S$—, hydroxy$(C_1-C_{10})$alkyl, mercapto$(C_1-C_6)$alkyl, $(NR^5R^6)$alkyl, or $(NR^5R^6)$carbonyl; and $R^8$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2013/170165 describes notably antibacterial compounds of formula (A5)

(A5)

wherein A is a substituted alkyl group, wherein at least one substituent is hydroxy, or A is a substituted cycloalkyl group, wherein at least one substituent is hydroxy or hydroxyalkyl; G is a group comprising at least one carbon-carbon double or triple bond and/or a phenyl ring; D represents a group selected from Q is O or NR, wherein R is H or an unsubstituted $(C_1-C_3)$ alkyl; $R^1$ and $R^2$ independently are selected from the group consisting of H and substituted or unsubstituted $(C_1-C_3)$ alkyl, or $R^1$ and $R^2$, together with the carbon atom to which they are attached, form an unsubstituted $(C_3-C_4)$cycloalkyl group or an unsubstituted 4-6 membered heterocyclic group; and $R^3$ is selected from the group consisting of hydrogen, substituted or unsubstituted $(C_1-C_3)$alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In WO 2015/036964, we have reported antibacterial 2H-indazole derivatives of general formula (A6)

(A6)

wherein
$R^1$ is H or halogen; $R^2$ is $(C_3-C_4)$alkynyloxy or the group M; $R^3$ is H or halogen; M is one of the groups $M^A$ and $M^B$ represented below $M^A$ $M^B$ wherein A is a bond, $CH_2CH_2$, CH=CH or C≡C; $R^{1A}$ is H or halogen; $R^{2A}$ is H, alkoxy or halogen; $R^{3A}$ is H, alkoxy, hydroxyalkoxy, thioalkoxy, trifluoromethoxy, amino, dialkylamino, hydroxyalkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-(dialkylamino)oxetan-3-yl, 3-hydroxythietan-3-yl, morpholin-4-ylalkoxy, morpholin-4-ylalkyl, oxazol-2-yl or [1,2,3]triazol-2-yl; and $R^{1B}$ is 3-hydroxyoxetan-3-yl, 3-hydroxythietan-3-yl, hydroxyalkyl, aminoalkyl, trans-2-hydroxymethyl-cycloprop-1-yl or 4-hydroxytetrahydro-2H-pyran-4-yl.

In another previous, yet unpublished patent application, we have reported antibacterial 1H-indazole derivatives of general formula (A7)

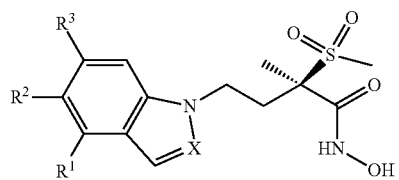
(A7)

wherein X is N or CH; $R^1$ is H or halogen; $R^2$ is $(C_3-C_4)$ alkynyloxy or the group M; $R^3$ is H or halogen; M is one of the groups $M^A$ and $M^B$ represented below

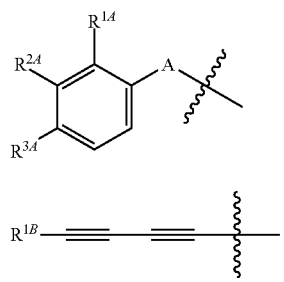
$M^A$ $M^B$ wherein A is a bond, $CH_2CH_2$, CH=CH or C≡C; $R^{1A}$ is H or halogen; $R^{2A}$ is H, $(C_1-C_3)$alkoxy or halogen; $R^{3A}$ is H, $(C_1-C_3)$alkoxy, hydroxy$(C_1-C_4)$alkyl, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl $(C_2-C_3)$alkoxy, morpholin-4-yl-$(C_1-C_2)$alkyl, oxazol-2-yl or [1,2,3]triazol-2-yl; and $R^{1B}$ is 3-hydroxyoxetan-3-yl, 3-hydroxythietan-3-yl, hydroxy$(C_1-C_3)$alkyl, amino$(C_1-C_3)$ alkyl, 1-hydroxymethyl-cycloprop-1-yl or trans-2-hydroxymethyl-cycloprop-1-yl.

In a further previous, yet unpublished patent application, we have reported antibacterial 1,2-dihydro-3H-pyrrolo[1,2-c]imidazol-3-one derivatives of general formula (A8)

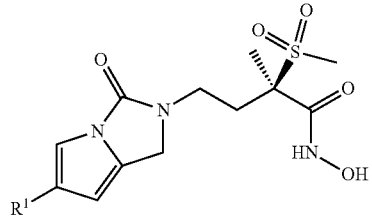
(A8)

wherein $R^1$ is the group M; M is one of the groups $M^A$ and $M^B$ represented below

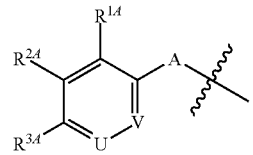
$M^A$

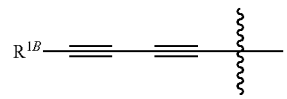
$M^B$ wherein A is a bond, CH=CH or C≡C; U is N or CH; V is N or CH; $R^{1A}$ is H or halogen; $R^{2A}$ is H, $(C_1-C_3)$alkoxy or halogen; $R^{3A}$ is H, $(C_1-C_3)$alkoxy, hydroxy$(C_2-C_4)$alkoxy, $(C_1-C_3)$alkoxy$(C_1-C_3)$alkoxy, $(C_1-C_3)$thioalkoxy, trifluoromethoxy, amino, hydroxy$(C_1-C_4)$alkyl, $(C_1-C_3)$alkoxy $(C_1-C_4)$alkyl, 3-hydroxy-3-methylbut-1-yn-1-yl, 2-hydroxyacetamido, (carbamoyloxy)methyl, 1-hydroxymethylcycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1,2-dihydroxyethyl,3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl$(C_2-C_3)$alkoxy, [4-N-$(C_1-C_3)$alkylpiperazin-1-yl]$(C_1-C_3)$alkyl, morpholin-4-yl-$(C_1-C_2)$alkyl, [1,2,3]triazol-2-yl or 3-[hydroxy$(C_2-C_3)$alkyl]-2-oxo-imidazolidin-1-yl; and $R^{1B}$ is 3-hydroxyoxetan-3-yl, 3-hydroxythietan-3-yl, 3-(hydroxy $(C_1-C_3)$alkyl)oxetan-3-yl, hydroxy$(C_1-C_3)$alkyl, 1,2-dihydroxyethyl, amino$(C_1-C_3)$alkyl, 1-hydroxymethyl-cycloprop-1-yl, trans-2-hydroxymethyl-cycloprop-1-yl, trans-(cis-3,4-dihydroxy)-cyclopent-1-yl or 3-hydroxymethylbicyclo [1,1,1]pentan-1-yl.

In WO 2011/073845, WO 2012/120397 or WO 2013/170165, further LpxC inhibitors are disclosed, among others the compounds of general formula (A9)

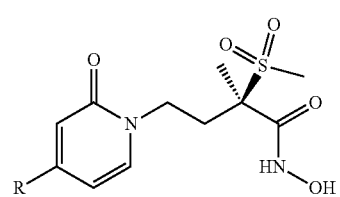
(A9)

wherein R can notably be phenylethynyl or styryl.

Besides, in Montgomery et al., *J. Med. Chem.* (2012), 55(4), 1662-1670, yet further LpxC inhibitors are disclosed, among others the compound of formula (A10)

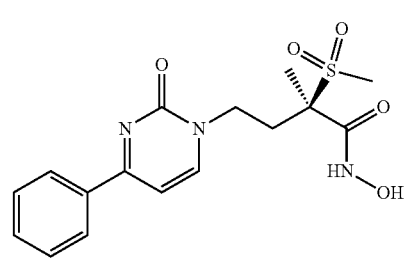
(A10)

The antibacterial compound of formula (A11)

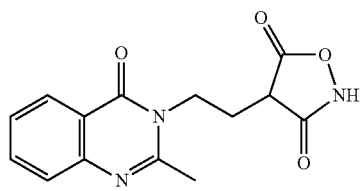

(A11)

has furthermore been described in El-Zohry and Abd-Alla, *J. Chem. Tech. Biotechnol.* (1992), 55, 209-215.

The instant invention provides new antibacterial quinazoline-4(3H)-one derivatives, namely the compounds of formula I described herein.

Various embodiments of the invention are presented hereafter:

1) The invention relates to compounds of formula I

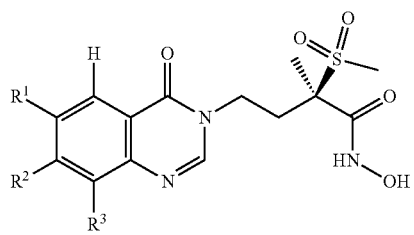

I wherein
$R^1$ is H or halogen;
$R^2$ is the group M;
$R^3$ is H or halogen;
M is one of the groups $M^A$ and $M^B$ represented below

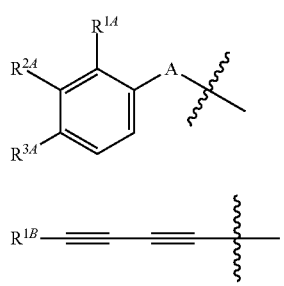

$M^A$ $M^B$ wherein A represents a bond or C≡C;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy $(C_1-C_4)$alkyl, 1,2-dihydroxyethyl, di$(C_1-C_3)$alkylamino, 1-hydroxymethyl-cycloprop-1-yl, 1-((dimethylglycyl)oxy)methyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, [di$(C_1-C_3)$alkylamino]-$(C_1-C_3)$alkyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy$(C_1-C_3)$alkyl)oxetan-3-yl, 3-hydroxythietan-3-yl, trans-(cis-3,4-dihydroxy)-cyclopent-1-yl, 3-(2-aminoacetamido)cyclopentyl, 3-hydroxymethylbicyclo[1,1,1]pentan-1-yl or 3-hydroxyoxetan-3-ylmethyl;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "halogen" refers to fluorine, chlorine, bromine or iodine, and preferably to fluorine or chlorine, and most preferably to fluorine.

The term "alkyl", used alone or in combination, refers to a straight or branched chain alkyl group containing from one to four carbon atoms. The term "$(C_x-C_y)$alkyl" (x and y each being an integer) refers to a straight or branched chain alkyl group containing x to y carbon atoms. For example, a $(C_1-C_3)$alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "hydroxyalkyl", used alone or in combination, refers to an alkyl group as defined before wherein one hydrogen atom has been replaced by a hydroxy group, with the proviso that none of the carbon atoms bears two oxygen atoms. The term "hydroxy$(C_x-C_y)$alkyl" (x and y each being an integer) refers to a hydroxyalkyl group as defined which contains x to y carbon atoms. For example, a hydroxy$(C_1-C_4)$alkyl group is a hydroxyalkyl group as defined before which contains from one to four carbon atoms. Representative examples of hydroxyalkyl groups include hydroxymethyl, 2-hydroxyethyl, 2-hydroxypropyl and 3-hydroxypropyl. Preferred are hydroxymethyl and 2-hydroxyethyl. Most preferred is hydroxymethyl.

The term "aminoalkyl", used alone or in combination, refers to an alkyl group as defined before wherein one hydrogen atom has been replaced by an amino group. The term "amino$(C_x-C_y)$alkyl" (x and y each being an integer) refers to an aminoalkyl group as defined which contains x to y carbon atoms. For example, an amino$(C_1-C_3)$alkyl group is an aminoalkyl group as defined before which contains from one to three carbon atoms. Representative examples of aminoalkyl groups include aminomethyl, 2-aminoethyl, 2-aminopropyl, 2-aminoprop-2-yl and 3-aminopropyl. Preferred are aminomethyl, 2-aminoethyl and 2-aminopropyl. Most preferred is 2-aminoprop-2-yl.

The term "dialkylamino", used alone or in combination, refers to an amino group wherein each hydrogen atom has been replaced by an alkyl group as defined before, whereby the alkyl groups may be the same or different. The term "di$(C_x-C_y)$alkylamino" (x and y each being an integer) refers to a dialkylamino group as defined before wherein each alkyl group independently contains x to y carbon atoms. For example, a di$(C_1-C_3)$ alkylamino group is a dialkylamino group as defined before wherein each alkyl group independently contains from one to three carbon atoms. Representative examples of dialkylamino groups include dimethylamino, diethylamino, N-ethyl-N-methyl-amino and N-iso-propyl-N-methyl-amino. Preferred are dimethylamino and diethylamino. Most preferred is dimethylamino.

The term [di($C_1$-$C_3$)alkylamino]-($C_1$-$C_3$)alkyl refers to an alkyl group containing from one to three carbon atoms as defined before wherein one of the hydrogen atoms has been replaced by di($C_1$-$C_3$)alkylamino group as defined before. Representative examples of [di($C_1$-$C_3$)alkylamino]-($C_1$-$C_3$)alkyl groups include dimethylaminomethyl, 2-(dimethylamino)-ethyl, 3-(dimethylamino)-propyl, diethylaminomethyl, 2-(diethylamino)-ethyl, 3-(diethylamino)-propyl, di(n-propyl)aminomethyl, 2-(di(n-propyl)amino)-ethyl and 3-(di(n-propyl)amino)-propyl. Preferred are dimethylaminomethyl, 2-(dimethylamino)-ethyl and 3-(dimethylamino)-propyl. Most preferred is dimethylaminomethyl.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "hydroxyalkoxy", used alone or in combination, refers to a straight or branched chain alkoxy group containing from one to four carbon atoms wherein one of the carbon atoms bears a hydroxy group. The term "hydroxy($C_x$-$C_y$)alkoxy" (x and y each being an integer) refers to a hydroxyalkoxy group as defined before containing x to y carbon atoms. For example, a hydroxy($C_2$-$C_4$)alkoxy group contains from two to four carbon atoms. Representative examples of hydroxyalkoxy groups include 2-hydroxyethoxy, 2-hydroxypropoxy, 3-hydroxypropoxy and 4-hydroxybutoxy. Preferred are 2-hydroxyethoxy and 3-hydroxypropoxy. Most preferred is 2-hydroxyethoxy.

The term "3-(hydroxy($C_1$-$C_3$)alkyl)oxetan-3-yl" refers to an oxetan-3-yl group wherein the hydrogen on the carbon at position 3 of the oxetane ring has been replaced by a hydroxy($C_1$-$C_3$)alkyl group as defined before. Examples of 3-(hydroxy($C_1$-$C_3$)alkyl)oxetan-3-yl groups are 3-hydroxymethyl-oxetan-3-yl and 3-(2-hydroxyethyl)-oxetan-3-yl. The most preferred 3-(hydroxy($C_1$-$C_3$)alkyl)oxetan-3-yl group is 3-hydroxymethyl-oxetan-3-yl.

The term "morpholin-4-yl-($C_1$-$C_2$)alkyl" refers to a ($C_1$-$C_2$)alkyl group as defined before wherein one of the hydrogen atoms has been replaced by a morpholin-4-yl group. Examples of morpholin-4-yl-($C_1$-$C_2$)alkyl groups are morpholin-4-ylmethyl and 2-morpholin-4-yl-ethyl. The most preferred morpholin-4-yl($C_1$-$C_2$)alkyl group is morpholin-4-ylmethyl.

The term "morpholin-4-yl($C_2$-$C_3$)alkoxy" refers to a ($C_2$-$C_3$)alkoxy group as defined before wherein one of the hydrogen atoms has been replaced by a morpholin-4-yl group. Examples of morpholin-4-yl($C_2$-$C_3$)alkoxy groups are 2-(morpholin-4-yl)ethoxy and 3-(morpholin-4-yl)propoxy.

The term "quinolone-resistant", when used in this text, refers to a bacterial strain against which ciprofloxacin has a Minimal Inhibitory Concentration of at least 16 mg/L (said Minimal Inhibitory Concentration being measured with the standard method described in "*Methods for Dilution Antimicrobial Susceptibility Tests for Bacteria that Grow Aerobically*", Approved standard, 7$^{th}$ ed., Clinical and Laboratory Standards Institute (CLSI) Document M7-A7, Wayne, Pa., USA (2006)).

The term "carbapenem-resistant", when used in this text, refers to a bacterial strain against which imipenem has a Minimal Inhibitory Concentration of at least 16 mg/L (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, amino-glycosides, phosphonic acids, tetracycline and polymixins. Clinical breakpoints are defined according to the latest available list published by Clinical and Laboratory Standards Institute (Wayne, Pa., U.S.A.). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example '*Handbook of Pharmaceutical Salts. Properties, Selection and Use.*', P. Heinrich Stahl, Camille G. Wermuth (Eds.), Wiley-VCH (2008) and '*Pharmaceutical Salts and Co-crystals*', Johan Wouters and Luc Quere (Eds.), RSC Publishing (2012).

In this text, a bond interrupted by a wavy line shows a point of attachment of the radical drawn to the rest of the molecule. For example, the radical drawn below

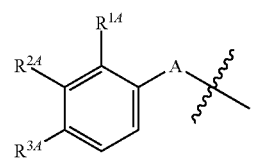

wherein A represents a bond, and each of $R^{1A}$, $R^{2A}$ and $R^{3A}$ represents H is the phenyl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention notably relates to compounds of formula I according to embodiment 1) that are also compounds of formula $I_P$

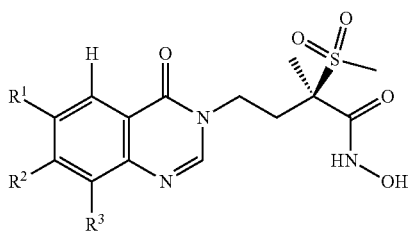

$I_P$ wherein
$R^1$ is H or halogen;
$R^2$ is the group M;
$R^3$ is H or halogen;
M is one of the groups $M^A$ and $M^B$ represented below

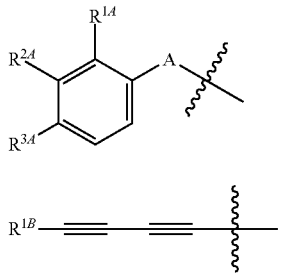

$M^A$ $M^B$ wherein A represents a bond or CC;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy $(C_1-C_4)$alkyl, 1,2-dihydroxyethyl, di$(C_1-C_3)$alkylamino, 1-hydroxymethyl-cycloprop-1-yl, 1-((dimethylglycyl)oxy)methyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, 1,2-dihydroxyprop-3-yl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, 3-(hydroxy$(C_1-C_3)$alkyl)oxetan-3-yl, 3-hydroxythietan-3-yl, trans-(cis-3,4-dihydroxy)-cyclopent-1-yl, 3-(2-amino acetamido)cyclopentyl or 3-hydroxymethylbicyclo[1,1,1]pentan-1-yl;
and to salts (in particular pharmaceutically acceptable salts) of said compounds of formula $I_P$.

3) The invention in particular relates to compounds of formula I according to embodiment 1) which are also compounds of formula $I_{CE}$

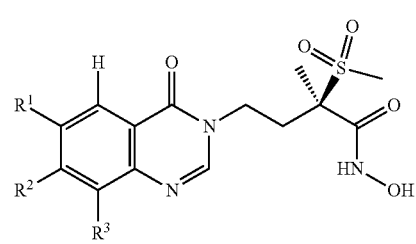

$I_{CE}$ wherein
$R^1$ is H or halogen;
$R^2$ is the group M;
$R^3$ is H or halogen;
M is one of the groups $M^A$ and $M^B$ represented below

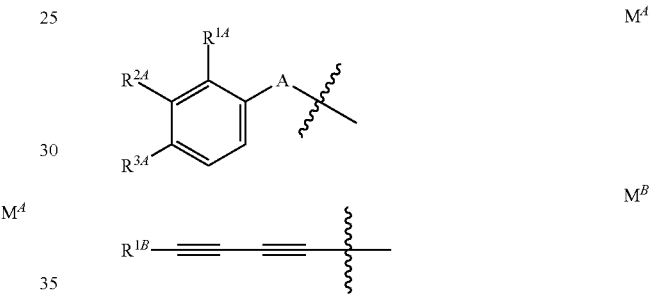

$M^A$ $M^B$ wherein A represents a bond or CC;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy $(C_1-C_4)$alkyl, 1,2-dihydroxyethyl, di$(C_1-C_3)$alkylamino, 1-hydroxymethyl-cycloprop-1-yl, 1-((dimethylglycyl)oxy)methyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, dimethylamino-$(C_1-C_3)$alkyl, 1,2-dihydroxyprop-3-yl, 1-aminocycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, trans-(cis-3,4-dihydroxy)-cyclopent-1-yl, 3-(2-aminoacetamido)cyclopentyl, 3-hydroxymethylbicyclo[1,1,1]pentan-1-yl or 3-hydroxyoxetan-3-ylmethyl;
and to salts (in particular pharmaceutically acceptable salts) of compounds of formula $I_{CE}$.

4) The invention in particular relates to compounds of formula $I_{CE}$ according to embodiment 3) which are also compounds of formula $I_{CEP}$ $I_{CEP}$

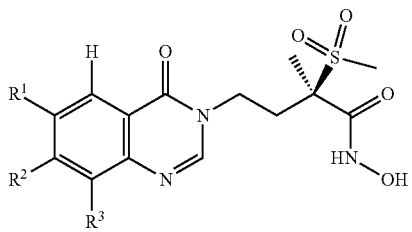

wherein
R¹ is H or halogen;
R² is the group M;
R³ is H or halogen;
M is one of the groups $M^A$ and $M^B$ represented below $M^A$

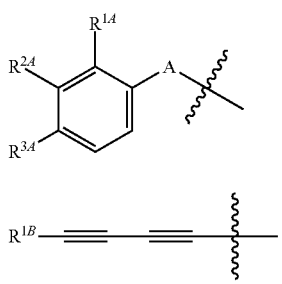

$M^B$

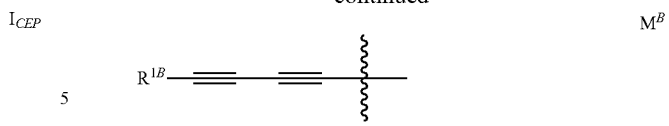

wherein A represents a bond or C≡C;
$R^{1A}$ is H or halogen;
$R^{2A}$ is H, (C₁-C₃)alkoxy or halogen;
$R^{3A}$ is H, (C₁-C₃)alkoxy, hydroxy(C₂-C₄)alkoxy, hydroxy (C₁-C₄)alkyl, 1,2-dihydroxyethyl, di(C₁-C₃)alkylamino, 1-hydroxymethyl-cycloprop-1-yl, 1-((dimethylglycyl)oxy)methyl-cycloprop-1-yl, 3-hydroxyoxetan-3-yl, morpholin-4-yl-(C₁-C₂)alkyl or morpholin-4-yl(C₂-C₃) alkoxy; and
$R^{1B}$ is hydroxy(C₁-C₃)alkyl, amino(C₁-C₃)alkyl, 1,2-dihydroxyprop-3-yl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, trans-(cis-3,4-dihydroxy)-cyclopent-1-yl, 3-(2-amino acetamido)cyclopentyl or 3-hydroxymethylbicyclo [1,1,1]pentan-1-yl;
and to salts (in particular pharmaceutically acceptable salts) of said compounds of formula $I_{CEP}$.

5) In particular, the compounds of formula $I_{CE}$ according to embodiment 3) will be such that R² is the group M and M is the group $M^A$ or $M^B$ $M^A$

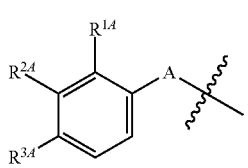

$M^B$

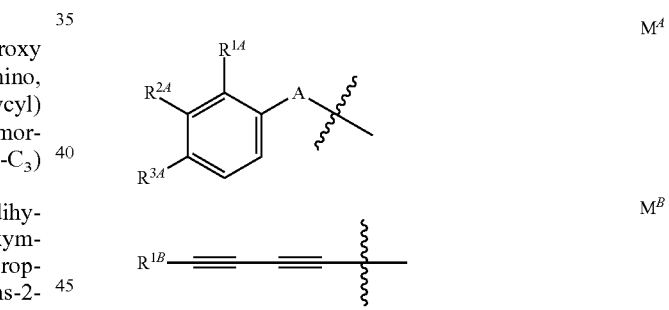

wherein A represents a bond or C≡C;
$R^{1A}$ is H or fluorine;
$R^{2A}$ is H, methoxy or fluorine;
$R^{3A}$ is H, methoxy, hydroxy(C₂-C₄)alkoxy, hydroxy(C₁-C₄)alkyl, 1,2-dihydroxyethyl, dimethylamino, 1-hydroxymethyl-cycloprop-1-yl, 1-((dimethylglycyl)oxy)methyl-cycloprop-1-yl, 3-hydroxyoxetan-3-yl, morpholin-4-yl-(C₁-C₂)alkyl or morpholin-4-yl(C₂-C₃)alkoxy; and
$R^{1B}$ is hydroxy(C₁-C₃)alkyl, amino(C₁-C₃)alkyl, dimethylaminomethyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, 1-(hydroxymethyl)cyclobut-1-yl, 3-hydroxyoxetan-3-yl, trans-(cis-3,4-dihydroxy)-cyclopent-1-yl, 3-(2-amino acetamido)cyclopentyl, 3-hydroxymethylbicyclo[1,1,1]pentan-1-yl or 3-hydroxyoxetan-3-ylmethyl.

6) The compounds of formula $I_{CEP}$ according to embodiment 4) will notably be such that R² is the group M and M is the group $M^A$ or $M^B$ $M^A$ $M^B$ wherein A represents a bond or C≡C;
$R^{1A}$ is H or fluorine;
$R^{2A}$ is H, methoxy or fluorine;
$R^{3A}$ is H, methoxy, hydroxy(C₂-C₄)alkoxy, hydroxy(C₁-C₄)alkyl, 1,2-dihydroxyethyl, dimethylamino, 1-hydroxymethyl-cycloprop-1-yl, 1-((dimethylglycyl)oxy)methyl-cycloprop-1-yl, 3-hydroxyoxetan-3-yl, morpholin-4-yl-(C₁-C₂)alkyl or morpholin-4-yl(C₂-C₃)alkoxy; and
$R^{1B}$ is hydroxy(C₁-C₃)alkyl, amino(C₁-C₃)alkyl, 1,2-dihydroxyprop-3-yl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, 3-hydroxyoxetan-3-yl, trans-(cis-3 ₅4-dihydroxy)-cyclopent-1-yl, 3-(2-aminoacetamido)cyclopentyl or 3-hydroxymethylbicyclo [1,1,1] pentan-1-yl.

7) In particular, the compounds of formula I according to one of embodiments 1) to 6) will be such that R¹ is H or fluorine, $R^3$ is H or fluorine, $R^{1A}$, when present, is H or fluorine and $R^{2A}$, when present, is H.

8) According to one main embodiment of this invention, the compounds of formula I as defined in one of embodiments 1) to 7) will be such that $R^1$ is the group $M^A$.

9) One sub-embodiment of embodiment 8) relates to the compounds of formula I as defined in embodiment 8) wherein A represents a bond.

10) Preferably, the compounds of formula I according to embodiment 9) will be such that $R^{1A}$ is H or halogen, $R^{2A}$ is H and $R^{3A}$ is ($C_1$-$C_3$)alkoxy.

11) More preferably, the compounds of formula I according to embodiment 9) will be such that $R^{1A}$ is H or fluorine, $R^{2A}$ is H and $R^{3A}$ is methoxy.

12) Even more preferably, the compounds of formula I according to embodiment 9) will be such that $R^{1A}$ represents fluorine, $R^{2A}$ represents H and $R^{3A}$ represents methoxy.

13) Another sub-embodiment of embodiment 8) relates to the compounds of formula I as defined in embodiment 8) wherein A represents C≡C.

14) Preferably, the compounds of formula I according to embodiment 13) will be such that $R^{1A}$ is H or halogen, $R^{2A}$ is H and $R^{3A}$ is hydroxy($C_2$-$C_4$)alkoxy, hydroxy($C_1$-$C_4$)alkyl, 1,2-dihydroxyethyl, 1-hydroxymethyl-cycloprop-1-yl or 3-hydroxyoxetan-3-yl.

15) More preferably, the compounds of formula I according to embodiment 13) will be such that $R^{1A}$ is H or fluorine, $R^{2A}$ is H and $R^{3A}$ is hydroxy($C_1$-$C_4$)alkyl, 1,2-dihydroxyethyl or 3-hydroxyoxetan-3-yl.

16) Even more preferably, the compounds of formula I according to embodiment 13) will be such that $R^{1A}$ is H or fluorine, $R^{2A}$ is H and $R^{3A}$ is hydroxymethyl, 1,2-dihydroxyethyl or 3-hydroxyoxetan-3-yl.

17) According to another main embodiment of this invention, the compounds of formula I as defined in one of embodiments 1) to 7) will be such that $R^1$ is the group $M^B$.

18) Preferably, the compounds of formula I according to embodiment 17) will be such that $R^{1B}$ is hydroxy($C_1$-$C_3$)alkyl, amino($C_1$-$C_3$)alkyl, [di($C_1$-$C_3$)alkylamino]-($C_1$-$C_3$)alkyl, 1,2-dihydroxyethyl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy($C_1$-$C_3$)alkyl)oxetan-3-yl, trans-(cis-3,4-dihydroxy)-cyclopent-1-yl, 3-(2-aminoacetamido)cyclopentyl, 3-hydroxymethylbicyclo [1,1,1]pentan-1-yl or 3-hydroxyoxetan-3-ylmethyl (and in particular such that $R^{1B}$ is hydroxy($C_1$-$C_3$)alkyl, amino($C_1$-$C_3$)alkyl, 1,2-dihydroxyethyl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, 3-(hydroxy($C_1$-$C_3$)alkyl)oxetan-3-yl, trans-(cis-3,4-dihydroxy)-cyclopent-1-yl, 3-(2-aminoacetamido)cyclopentyl or 3-hydroxymethylbicyclo [1,1,1]pentan-1-yl).

19) More preferably, the compounds of formula I according to embodiment 17) will be such that $R^{1B}$ is hydroxy($C_1$-$C_3$)alkyl, amino($C_1$-$C_3$)alkyl, dimethylamino-($C_1$-$C_3$)alkyl, 1,2-dihydroxyethyl, 1-amino-cycloprop-1-yl, 1-hydroxymethyl-cycloprop-1-yl, trans-2-hydroxymethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, trans-(cis-3,4-dihydroxy)-cyclopent-1-yl or 3-hydroxymethylbicyclo [1,1,1]pentan-1-yl (and in particular such that $R^{1B}$ is hydroxy($C_1$-$C_3$)alkyl, amino($C_1$-$C_3$)alkyl, 1,2-dihydroxyethyl, 1-amino-cycloprop-1-yl, 1-hydroxymethyl-cycloprop-1-yl, trans-2-hydroxymethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, trans-(cis-3,4-dihydroxy)-cyclopent-1-yl or 3-hydroxymethylbicyclo[1,1,1]pentan-1-yl).

20) Even more preferably, the compounds of formula I according to embodiment 17) will be such that $R^{1B}$ is 1-amino-cycloprop-1-yl, trans-2-hydroxymethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, trans-2-(1,2-dihydroxyethyl)-cycloprop-1-yl, trans-(cis-3,4-dihydroxy)-cyclopent-1-yl or 3-hydroxymethylbicyclo [1,1,1]pentan-1-yl (and in particular such that $R^{1B}$ is 1-amino-cycloprop-1-yl, trans-2-hydroxymethyl-cycloprop-1-yl, trans-2-hydroxymethyl-1-methyl-cycloprop-1-yl, trans-2-hydroxymethyl-2-methyl-cycloprop-1-yl, trans-2-(1,2-dihydroxyethyl)-cycloprop-1-yl, trans-(cis-3,4-dihydroxy)-cyclopent-1-yl or 3-hydroxymethylbicyclo[1,1,1]pentan-1-yl).

21) According to one variant of this invention, the compounds of formula I according to one of embodiments 1) to 7) will be such that $R^1$ represents H and $R^3$ represents H.

22) According to another variant of this invention, the compounds of formula I according to one of embodiments 1) to 7) will be such that $R^1$ represents fluorine and $R^3$ represents H.

23) According to yet another variant of this invention, the compounds of formula I according to one of embodiments 1) to 7) will be such that $R^1$ represents H and $R^3$ represents fluorine.

24) In a preferred embodiment, the compounds of formula I according to embodiment 1) will be such that:
$R^1$ is H or halogen;
$R^2$ is the group M;
$R^3$ is H or halogen;
M is the one of the groups $M^A$ and $M^B$ represented below

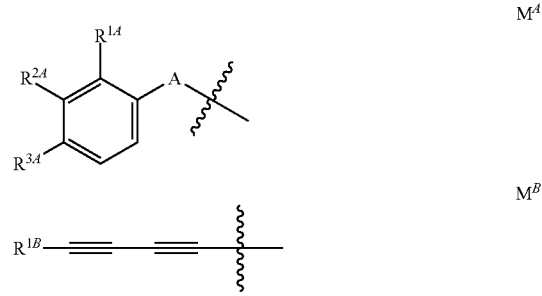

wherein A represents a bond or —C≡C—;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy$(C_1-C_4)$alkyl, 1,2-dihydroxyethyl, di$(C_1-C_3)$alkylamino, 1-hydroxymethyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, [di$(C_1-C_3)$alkylamino]-$(C_1-C_3)$alkyl, 1,2-dihydroxyethyl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy$(C_1-C_3)$alkyl)oxetan-3-yl, trans-(cis-3,4-dihydroxy)-cyclopent-1-yl, 3-(2-amino acetamido)cyclopentyl, 3-hydroxymethylbicyclo[1,1,1]pentan-1-yl or 3-hydroxyoxetan-3-ylmethyl.

25) In a preferred embodiment, the compounds of formula $I_P$ according to embodiment 2) will be such that:
$R^1$ is H or halogen;
$R^2$ is the group M;
$R^3$ is H or halogen;
M is the one of the groups $M^A$ and $M^B$ represented below

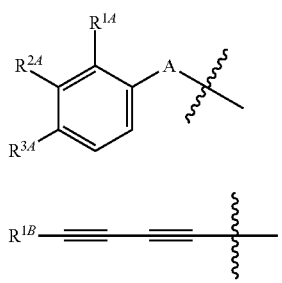

wherein A represents a bond or —C≡C—;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy$(C_1-C_4)$alkyl, 1,2-dihydroxyethyl, di$(C_1-C_3)$alkylamino, 1-hydroxymethyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, 1,2-dihydroxyethyl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, 3-(hydroxy$(C_1-C_3)$alkyl)oxetan-3-yl, trans-(cis-3,4-dihydroxy)-cyclopent-1-yl, 3-(2-aminoacetamido)cyclopentyl or 3-hydroxymethylbicyclo[1,1,1]pentan-1-yl.

26) In a more preferred embodiment, the compounds of formula I according to embodiment 1) or 3) will be such that:
$R^1$ is H or fluorine;
$R^2$ is the group M;
$R^3$ is H;
M is the one of the groups $M^A$ and $M^B$ represented below

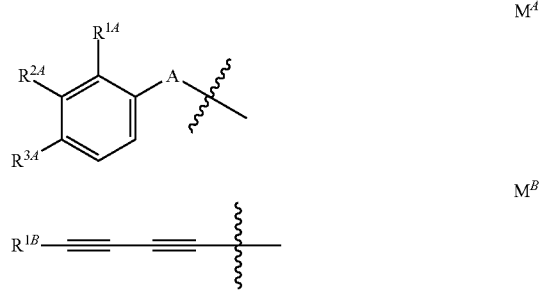

wherein A represents a bond or —C≡C—;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy$(C_1-C_4)$alkyl, 1,2-dihydroxyethyl, di$(C_1-C_3)$alkylamino, 1-hydroxymethyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, dimethylamino-$(C_1-C_3)$alkyl, 1,2-dihydroxyethyl, 1-amino-cycloprop-1-yl, 1-hydroxymethyl-cycloprop-1-yl, trans-2-hydroxymethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, trans-(cis-3,4-dihydroxy)-cyclopent-1-yl or 3-hydroxymethylbicyclo[1,1,1]pentan-1-yl.

27) In a more preferred embodiment, the compounds of formula $I_P$ according to embodiment 2) or 4) will be such that:
$R^1$ is H or fluorine;
$R^2$ is the group M;
$R^3$ is H;
M is the one of the groups $M^A$ and $M^B$ represented below

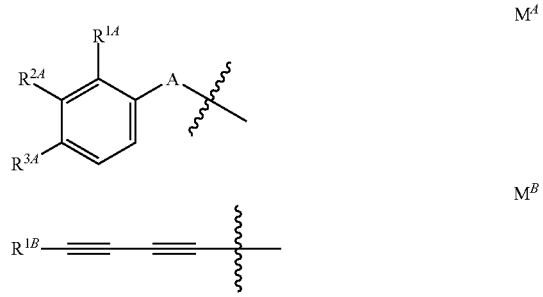

wherein A represents a bond or —C≡C—;
$R^{1A}$ is H or halogen;

$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy$(C_1-C_4)$alkyl, 1,2-dihydroxyethyl, di$(C_1-C_3)$alkylamino, 1-hydroxymethyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, 1,2-dihydroxyethyl, 1-amino-cycloprop-1-yl, 1-hydroxymethyl-cycloprop-1-yl, trans-2-hydroxymethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, trans-(cis-3,4-dihydroxy)-cyclopent-1-yl or 3-hydroxymethylbicyclo[1,1,1]pentan-1-yl.

28) In an even more preferred embodiment, the compounds of formula I according to embodiment 1) or 3) will be such that:
$R^1$ is H or fluorine;
$R^3$ is H;
$R^2$ is the group $M^B$ represented below

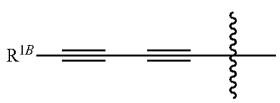

wherein $R^{1B}$ is 1-amino-cycloprop-1-yl, trans-2-hydroxymethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, trans-2-(1,2-dihydroxyethyl)-cycloprop-1-yl, trans-(cis-3,4-dihydroxy)-cyclopent-1-yl or 3-hydroxymethylbicyclo[1,1,1]pentan-1-yl.

29) In an even more preferred embodiment, the compounds of formula $I_P$ according to embodiment 2) or 4) will be such that:
$R^1$ is H or fluorine;
$R^3$ is H;
$R^2$ is the group $M^B$ represented below

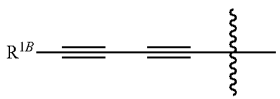

wherein $R^{1B}$ is 1-amino-cycloprop-1-yl, trans-2-hydroxymethyl-cycloprop-1-yl, trans-2-hydroxymethyl-1-methyl-cycloprop-1-yl, trans-2-hydroxymethyl-2-methyl-cycloprop-1-yl, trans-2-(1,2-dihydroxyethyl)-cycloprop-1-yl, trans-(cis-3,4-dihydroxy)-cyclopent-1-yl or 3-hydroxymethylbicyclo[1,1,1]pentan-1-yl.

30) Another embodiment of this invention relates to compounds of formula I as defined in one of embodiments 1) to 29) as well as to isotopically labelled, especially $^2$H (deuterium) labelled compounds of formula I as defined in one of embodiments 1) to 29), which compounds are identical to the compounds of formula I as defined in one of embodiments 1) to 29) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

31) Particularly preferred are the following compounds of formula I as defined in one of embodiments 1) to 4):
(R)-4-(7-(2-fluoro-4-methoxyphenyl)-4-oxoquinazolin-3(4H)-yl)-N-hydroxy-2-methyl-2-(methylsulfonyl)butanamide;
(R)-N-hydroxy-2-methyl-2-(methylsulfonyl)-4-(4-oxo-7-phenylquinazolin-3(4H)-yl)butanamide;
(R)-N-hydroxy-4-(7-(((1S,2S)-2-(hydroxymethyl)cyclopropyl)buta-1,3-diyn-1-yl)-4-oxoquinazolin-3(4H)-yl)-2-methyl-2-(methylsulfonyl)butanamide;
(R)-N-hydroxy-4-(7-((3-hydroxyoxetan-3-yl)buta-1,3-diyn-1-yl)-4-oxoquinazolin-3(4H)-yl)-2-methyl-2-(methylsulfonyl)butanamide;
(R)-N-hydroxy-4-(7-(((1R,2R)-2-(hydroxymethyl)cyclopropyl)buta-1,3-diyn-1-yl)-4-oxoquinazolin-3(4H)-yl)-2-methyl-2-(methylsulfonyl)butanamide;
(R)-N-hydroxy-4-(7-((1-(hydroxymethyl)cyclopropyl)buta-1,3-diyn-1-yl)-4-oxoquinazolin-3(4H)-yl)-2-methyl-2-(methylsulfonyl)butanamide;
(R)-4-(7-(5-amino-5-methylhexa-1,3-diyn-1-yl)-4-oxoquinazolin-3(4H)-yl)-N-hydroxy-2-methyl-2-(methylsulfonyl)butanamide;
(R)-N-hydroxy-4-(7-((4-(2-hydroxyethyl)phenyl)ethynyl)-4-oxoquinazolin-3(4H)-yl)-2-methyl-2-(methylsulfonyl)butanamide;
(R)-4-(6-fluoro-7-(((1S,2S)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-4-(7-((R)-5,6-dihydroxyhexa-1,3-diyn-1-yl)-4-oxoquinazolin-3(4H)-yl)-N-hydroxy-2-methyl-2-(methylsulfonyl)butanamide;
(R)-4-(6-fluoro-7-(((1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-4-(6-fluoro-7-((1-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-N-hydroxy-4-(7-((3-(hydroxymethyl)bicyclo[1.1.1]pentan-1-yl)buta-1,3-diyn-1-yl)-4-oxoquinazolin-3(4H)-yl)-2-methyl-2-(methylsulfonyl)butanamide;
(R)-N-hydroxy-4-(7-((4-(2-hydroxyethoxy)phenyl)ethynyl)-4-oxoquinazolin-3(4H)-yl)-2-methyl-2-(methylsulfonyl)butanamide;
(R)-4-(7-(((1s,3R,4S)-3,4-dihydroxycyclopentyl)buta-1,3-diyn-1-yl)-4-oxoquinazolin-3(4H)-yl)-N-hydroxy-2-methyl-2-(methylsulfonyl)butanamide;
(R)-N-hydroxy-4-(7-((4-(1-(hydroxymethyl)cyclopropyl)phenyl)ethynyl)-4-oxoquinazolin-3(4H)-yl)-2-methyl-2-(methylsulfonyl)butanamide;

(R)-N-hydroxy-4-(7-(((1S,2R)-2-(hydroxymethyl)-2-methylcyclopropyl)buta-1,3-diyn-1-yl)-4-oxoquinazolin-3(4H)-yl)-2-methyl-2-(methylsulfonyl)butanamide;

(R)-4-(7-((4-((R)-1,2-dihydroxyethyl)phenyl)ethynyl)-4-oxoquinazolin-3(4H)-yl)-N-hydroxy-2-methyl-2-(methylsulfonyl)butanamide;

(2R)-4-(7-((1-(1,2-dihydroxyethyl)cyclopropyl)buta-1,3-diyn-1-yl)-4-oxoquinazolin-3(4H)-yl)-N-hydroxy-2-methyl-2-(methylsulfonyl)butanamide;

(R)-N-hydroxy-4-(7-(((1R,2R)-2-(hydroxymethyl)-1-methylcyclopropyl)buta-1,3-diyn-1-yl)-4-oxoquinazolin-3(4H)-yl)-2-methyl-2-(methylsulfonyl)butanamide;

(R)-4-(8-fluoro-7-(1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-(1-(4-((3-(4-(hydroxyamino)-3-methyl-3-(methylsulfonyl)-4-oxobutyl)-4-oxo-3,4-dihydroquinazolin-7-yl)ethynyl)phenyl)cyclopropyl)methyl dimethylglycinate;

(R)-4-(8-fluoro-7-(((1S,2S)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-N-hydroxy-4-(7-(((1R,2S)-2-(hydroxymethyl)-2-methylcyclopropyl)buta-1,3-diyn-1-yl)-4-oxoquinazolin-3(4H)-yl)-2-methyl-2-(methylsulfonyl)butanamide;

(R)-4-(7-((1-aminocyclopropyl)buta-1,3-diyn-1-yl)-4-oxoquinazolin-3(4H)-yl)-N-hydroxy-2-methyl-2-(methylsulfonyl)butanamide;

(R)-4-(7-(((1R,2R)-2-((S)-1,2-dihydroxyethyl)cyclopropyl)buta-1,3-diyn-1-yl)-4-oxoquinazolin-3(4H)-yl)-N-hydroxy-2-methyl-2-(methylsulfonyl)butanamide;

(R)-4-(7-((3-(2-aminoacetamido)cyclopentyl)buta-1,3-diyn-1-yl)-6-fluoro-4-oxoquinazolin-3(4H)-yl)-N-hydroxy-2-methyl-2-(methylsulfonyl)butanamide;

(R)-4-(7-(((1R,2R)-2-(aminomethyl)cyclopropyl)buta-1,3-diyn-1-yl)-6-fluoro-4-oxoquinazolin-3(4H)-yl)-N-hydroxy-2-methyl-2-(methylsulfonyl)butanamide;

(R)-4-(6-fluoro-7-(5-hydroxy-5-methylhexa-1,3-diyn-1-yl)-4-oxoquinazolin-3(4H)-yl)-N-hydroxy-2-methyl-2-(methylsulfonyl)butanamide;

as well as the salts (in particular the pharmaceutically acceptable salts) thereof.

32) Further preferred are the following compounds of formula I as defined in one of embodiments 1) to 4):

(R)-4-(7-(2-fluoro-4-(3-morpholinopropoxy)phenyl)-4-oxoquinazolin-3(4H)-yl)-N-hydroxy-2-methyl-2-(methylsulfonyl)butanamide;

(R)-N-hydroxy-2-methyl-2-(methylsulfonyl)-4-(7-(4-(3-morpholinopropoxy)phenyl)-4-oxoquinazolin-3(4H)-yl)butanamide;

(R)-4-(7-(2-fluoro-4-(2-morpholinoethoxy)phenyl)-4-oxoquinazolin-3(4H)-yl)-N-hydroxy-2-methyl-2-(methylsulfonyl)butanamide;

(R)-4-(7-(2-fluoro-3-methoxyphenyl)-4-oxoquinazolin-3(4H)-yl)-N-hydroxy-2-methyl-2-(methylsulfonyl)butanamide;

(R)-4-(7-(3-fluoro-4-methoxyphenyl)-4-oxoquinazolin-3(4H)-yl)-N-hydroxy-2-methyl-2-(methylsulfonyl)butanamide;

(R)-4-(7-(4-(dimethylamino)phenyl)-4-oxoquinazolin-3(4H)-yl)-N-hydroxy-2-methyl-2-(methylsulfonyl)butanamide;

(R)-N-hydroxy-4-(7-(4-(hydroxymethyl)phenyl)-4-oxoquinazolin-3(4H)-yl)-2-methyl-2-(methylsulfonyl)butanamide;

(R)-N-hydroxy-2-methyl-2-(methylsulfonyl)-4-(7-(4-(morpholinomethyl)phenyl)-4-oxoquinazolin-3(4H)-yl)butanamide;

(R)-4-(6-fluoro-4-oxo-7-phenylquinazolin-3(4H)-yl)-N-hydroxy-2-methyl-2-methylsulfonyl)butanamide;

(R)-N-hydroxy-4-(7-(4-(hydroxymethyl)phenyl)ethynyl)-4-oxoquinazolin-3(4H)-yl)-2-methyl-2-(methylsulfonyl)butanamide;

(R)-N-hydroxy-4-(7-(4-(3-hydroxyoxetan-3-yl)phenyl)ethynyl)-4-oxoquinazolin-3(4H)-yl)-2-methyl-2-(methylsulfonyl)butanamide; and (R)-N-hydroxy-2-methyl-2-(methylsulfonyl)-4-(7-((4-(morpholinomethyl)phenyl)ethynyl)-4-oxoquinazolin-3(4H)-yl)butanamide;

as well as the salts (in particular the pharmaceutically acceptable salts) thereof.

33) Also particularly preferred are the following compounds of formula I as defined in embodiment 1) or 3):

(R)-4-(7-(((1R*,2R*)-1-fluoro-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-4-(7-(((1R*,2R*)-1-fluoro-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-(1((3-(4-(hydroxyamino)-3-methyl-3-(methylsulfonyl)-4-oxobutyl)-4-oxo-3,4-dihydroquinazolin-7-yl)buta-1,3-diyn-1-yl)cyclopropyl)methyl dihydrogen phosphate;

(R)-4-(7-(5-(dimethylamino)penta-1,3-diyn-1-yl)-6-fluoro-4-oxoquinazolin-3(4H)-yl)-N-hydroxy-2-methyl-2-(methylsulfonyl)butanamide;

(R)-4-(7-(((1R*,2R*)-2-fluoro-2-(hydroxymethyl)cyclopropyl)buta-1,3-diyn-1-yl)-4-oxoquinazolin-3 (4H)-yl)-N-hydroxy-2-methyl-2-(methylsulfonyl)butanamide;

(R)-4-(6-fluoro-7-((1-(hydroxymethyl)cyclobutyl)buta-1,3-diyn-1-yl)-4-oxoquinazolin-3(4H)-yl)-N-hydroxy-2-methyl-2-(methylsulfonyl)butanamide;

(R)-4-(6-fluoro-7-(5-(3-hydroxyoxetan-3-yl)penta-1,3-diyn-1-yl)-4-oxoquinazolin-3(4H)-yl)-N-hydroxy-2-methyl-2-(methylsulfonyl)butanamide;

as well as the salts (in particular the pharmaceutically acceptable salts) thereof.

34) The invention further relates to the compounds of formula I as defined in embodiment 1) or 3) which are selected from the group consisting of the compounds listed in embodiment 31), the compounds listed in embodiment 32) and the compounds listed in embodiment 33). In particular, it also relates to the groups of compounds of formula I selected from the group consisting of the compounds listed in embodiment 31), the compounds listed in embodiment 32) and the compounds listed in embodiment 33), which groups of compounds furthermore correspond to one of embodiments 2) to 29), as well as to the salts (in particular the pharmaceutically acceptable salts) of such compounds. The invention moreover relates to any individual compound of formula I selected from the group consisting of the compounds listed in embodiment 31), the compounds listed in embodiment 32) and the compounds listed in embodiment 33), and to the salts (in particular the pharmaceutically acceptable salts) of such individual compound.

The compounds of formula I according to this invention, i.e. according to one of embodiments 1) to 34) above, exhibit antibacterial activity, especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophile*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. such as *Borrelia Burgdorferi*, *Brucella* spp. such as *Brucella melitensis*, *Burkholderia* spp. such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae*, *Legionella pneumophila*, *Mannheimia haemolyticus*, *Moraxella catarrhalis* (beta-lactamase positive and negative), *Morganella morganii*, *Neisseria* spp. such as *Neisseria gonorrhoeae* or *Neisseria meningitidis*, *Pasteurella* spp. such as *Pasteurella multocida*, *Plesiomonas shigelloides*, *Porphyromonas* spp. such as *Porphyromonas asaccharolytica*, *Prevotella* spp. such as *Prevotella corporis*, *Prevotella intermedia* or *Prevotella endodontalis*, *Proteus* spp. such as *Proteus mirabilis*, *Proteus vulgaris*, *Proteus penneri* or *Proteus myxofaciens*, *Porphyromonas asaccharolytica*, *Plesiomonas shigelloides*, *Providencia* spp. such as *Providencia stuartii*, *Providencia rettgeri* or *Providencia alcalifaciens*, *Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens*, *Ricketsia prowazekii*, *Salmonella* spp. such as *Salmonella typhi* or *Salmonella paratyphi*, *Serratia marcescens*, *Shigella* spp. such as *Shigella flexneri*, *Shigella boydii*, *Shigella sonnei* or *Shigella dysenteriae*, *Streptobacillus moniliformis*, *Stenotrophomonas maltophilia*, *Treponema* spp., *Vibrio* spp. such as *Vibrio cholerae*, *Vibrio parahaemolyticus*, *Vibrio vulnificus*, *Vibrio alginolyticus*, *Yersinia* spp. such as *Yersinia enterocolitica*, *Yersinia pestis* or *Yersinia pseudotuberculosis*.

The compounds of formula I according to this invention are thus useful for treating a variety of infections caused by fermentative or non-fermentative Gram-negative bacteria, especially infections such as: nosocomial pneumonia (related to infection by *Legionella pneumophila*, *Haemophilus influenzae*, or *Chlamydia pneumonia*); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis;* pharynigitis, rheumatic fever, and glomerulonephritis related to infection by *Actinobacillus haemolyticum;* sexually transmitted diseases related to infection by *Chlamydia trachormatis*, *Haemophilus ducreyi*, *Treponema pallidum*, *Ureaplasma urealyticum*, or *Neisseria gonorrheae;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis*, *Neisseria gonorrhoeae* or *H. influenzae;* gastroenteritis related to infection by *Campylobacter jejuni;* persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and are suitable, for the prevention or treatment of a bacterial infection caused by Gram-negative bacteria selected from the group consisting of *Burkholderia* spp. (e.g. *Burkholderia cepacia*), *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia* and *Pseudomonas aeruginosa* (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection mediated by quinolone-resistant, carbapenem-resistant or multi-drug resistant *Klebsiella pneumoniae* bacteria).

The compounds of formula I according to this invention, or the pharmaceutically acceptable salts thereof, may more especially be used for the preparation of a medicament, and are suitable, for the prevention or treatment of a bacterial infection caused by Gram-negative bacteria selected from the group consisting of *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia* and *Pseudomonas aeruginosa* bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention display intrinsic antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, cefatazidime, cefepime, cefotaxime) a carbapenem antibiotic (such as imipenem, or meropenem), a monobactam antibiotic (such as aztreonam or carumonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

The compounds of formula I according to this invention, or the pharmaceutically acceptable salt thereof, may moreover be used for the preparation of a medicament, and are suitable, for the prevention or treatment (and especially the treatment) of infections caused by biothreat Gram negative bacterial pathogens as listed by the US Center for Disease Control (the list of such biothreat bacterial pathogens can be found at the web page http://www.selectagents.gov/Select%20Agents%20and%20Toxins%20List.html), and in particular by Gram negative pathogens selected from the group consisting of *Yersinia pestis, Francisella tularensis* (tularemia), *Burkholderia pseudomallei* and *Burkholderia mallei*.

One aspect of this invention therefore relates to the use of a compound of formula I according to one of embodiments 1) to 34), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 34), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 34), or a pharmaceutically acceptable salt thereof, as a medicament. Yet a further aspect of this invention relates to a pharmaceutical composition containing, as active principle, a compound of formula I according to one of embodiments 1) to 34), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I, $I_P$, $I_{CE}$ or $I_{CEP}$.

Any reference to a compound of formula I, $I_P$, $I_{CE}$ or $I_{CEP}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 34) or a pharmaceutically acceptable salt thereof. Accordingly, the invention provides a method for the prevention or the treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by quinolone-resistant, carbapenem-resistant or multi-drug resistant *Klebsiella pneumoniae* bacteria) in a patient, comprising the administration to said patient of a pharmaceutically active amount of a compound of formula I according to one of embodiments 1) to 34) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 34), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by *Klebsiella pneumoniae* quinolone-resistant, carbapenem-resistant or multi-drug resistant bacteria). The following embodiments relating to the compounds of formula I according to embodiment 1) are thus possible and intended and herewith specifically disclosed in individualised form:

1, 2+1, 3+1, 4+3+1, 5+3+1, 6+4+3+1, 7+1, 7+2+1, 7+3+1, 7+4+3+1, 7+5+3+1, 7+6+4+3+1, 8+1, 8+2+1, 8+3+1, 8+4+3+1, 8+5+3+1, 8+6+4+3+1, 8+7+1, 8+7+2+1, 8+7+3+1, 8+7+4+3+1, 8+7+5+3+1, 8+7+6+4+3+1, 9+8+1, 9+8+2+1, 9+8+3+1, 9+8+4+3+1, 9+8+5+3+1, 9+8+6+4+3+1, 9+8+7+1, 9+8+7+2+1, 9+8+7+3+1, 9+8+7+4+3+1, 9+8+7+5+3+1, 9+8+7+6+4+3+1, 10+9+8+1, 10+9+8+2+1, 10+9+8+3+1, 10+9+8+4+3+1, 10+9+8+5+3+1, 10+9+8+6+4+3+1, 10+9+8+7+1, 10+9+8+7+2+1, 10+9+8+7+3+1, 10+9+8+7+4+3+1, 10+9+8+7+5+3+1, 10+9+8+7+6+4+3+1, 11+9+8+1, 11+9+8+2+1, 11+9+8+3+1, 11+9+8+4+3+1, 11+9+8+5+3+1, 11+9+8+6+4+3+1, 11+9+8+7+1, 11+9+8+7+2+1, 11+9+8+7+3+1, 11+9+8+7+4+3+1, 11+9+8+7+5+3+1, 11+9+8+7+6+4+3+1, 12+9+8+1, 12+9+8+2+1, 12+9+8+3+1, 12+9+8+4+3+1, 12+9+8+5+3+1, 12+9+8+6+4+3+1, 12+9+8+7+1, 12+9+8+7+2+1, 12+9+8+7+3+1, 12+9+8+7+4+3+1, 12+9+8+7+5+3+1, 12+9+8+7+6+4+3+1, 13+8+1, 13+8+2+1, 13+8+3+1, 13+8+4+3+1, 13+8+5+3+1, 13+8+6+4+3+1, 13+8+7+1, 13+8+7+2+1, 13+8+7+3+1, 13+8+7+4+3+1, 13+8+7+5+3+1, 13+8+7+6+4+3+1, 14+13+8+1, 14+13+8+2+1, 14+13+8+3+1, 14+13+8+4+3+1, 14+13+8+5+3+1, 14+13+8+6+4+3+1, 14+13+8+7+1, 14+13+8+7+2+1, 14+13+8+7+3+1, 14+13+8+7+4+3+1, 14+13+8+7+5+3+1, 14+13+8+7+6+4+3+1, 15+13+8+1, 15+13+8+2+1, 15+13+8+3+1, 15+13+8+4+3+1, 15+13+8+5+3+1, 15+13+8+6+4+3+1, 15+13+8+7+1, 15+13+8+7+2+1, 15+13+8+7+3+1, 15+13+8+7+4+3+1, 15+13+8+7+5+3+1, 15+13+8+7+6+4+3+1, 16+13+8+1, 16+13+8+2+1, 16+13+8+3+1, 16+13+8+4+3+1, 16+13+8+5+3+1, 16+13+8+6+4+3+1, 16+13+8+7+1, 16+13+8+7+2+1, 16+13+8+7+3+1, 16+13+8+7+4+3+1, 16+13+8+7+5+3+1, 16+13+8+7+6+4+3+1, 17+1, 17+2+1, 17+3+1, 17+4+3+1, 17+5+3+1, 17+6+4+3+1, 17+7+1, 17+7+2+1, 17+7+3+1, 17+7+4+3+1, 17+7+5+3+1, 17+7+6+4+3+1, 18+17+1, 18+17+2+1, 18+17+3+1, 18+17+4+3+1, 18+17+5+3+1, 18+17+6+4+3+1, 18+17+7+1, 18+17+7+2+1, 18+17+7+3+1, 18+17+7+4+3+1, 18+17+7+5+3+1, 18+17+7+6+4+3+1, 19+17+1, 19+17+2+1, 19+17+3+1, 19+17+4+3+1, 19+17+5+3+1, 19+17+6+4+3+1, 19+17+7+1, 19+17+7+2+1, 19+17+7+3+1, 19+17+7+4+3+1, 19+17+7+5+3+1, 19+17+7+6+4+3+1, 20+17+1, 20+17+2+1, 20+17+3+1, 20+17+4+3+1, 20+17+5+3+1, 20+17+6+4+3+1, 20+17+7+1, 20+17+7+2+1, 20+17+7+3+1, 20+17+7+4+3+1, 20+17+7+5+3+1, 20+17+7+6+4+3+1, 21+1, 21+2+1, 21+3+1, 21+4+3+1, 21+5+3+1, 21+6+4+3+1, 21+7+1, 21+7+2+1, 21+7+3+1, 21+7+4+3+1, 21+7+5+3+1, 21+7+6+4+3+1, 22+1, 22+2+1, 22+3+1, 22+4+3+1, 22+5+3+1, 22+6+4+3+1, 22+7+1, 22+7+2+1, 22+7+3+1, 22+7+4+3+1, 22+7+5+3+1, 22+7+6+4+3+1, 23+1, 23+2+1, 23+3+1, 23+4+3+1, 23+5+3+1, 23+6+4+3+1, 23+7+1, 23+7+2+1, 23+7+3+1, 23+7+4+3+1, 23+7+5+3+1, 23+7+6+4+3+1, 24+1, 25+2+1, 26+1, 26+3+1, 27+2+1, 27+4+3+1, 28+1, 28+3+1, 29+2+1, 29+4+3+1, 30+1, 30+2+1, 31+1, 31+2+1, 32+1, 32+2+1, 33+1, 33+2+1, 34+1 and 34+2+1.

In the list above, the numbers refer to the embodiments according to their numbering provided hereinabove whereas "+" indicates the dependency from another embodiment. The different individualised embodiments are separated by commas. In other words, "4+3+1" for example refers to embodiment 4) depending on embodiment 3), depending on embodiment 1), i.e. embodiment "4+3+1" corresponds to embodiment 1) further limited by the features of embodiments 3) and 4). Likewise, "13+8+7+1" refers to embodiment 13) depending mutatis mutandis on embodiments 8) and 7), depending on embodiment 1), i.e. embodiment "13+8+7+1" corresponds to embodiment 1) further limited by the features of embodiments 7) and 8), further limited by the features of embodiment 13).

The compounds of formula I can be manufactured in accordance with the present invention using the procedures described hereafter.

PREPARATION OF THE COMPOUNDS OF FORMULA I

Abbreviations:
The following abbreviations are used throughout the specification and the examples:
Ac acetyl
AcOH acetic acid
aq. aqueous
Bs 4-bromobenzenesulfonyl (brosylate)
BuLi n-butyl lithium
CC column chromatography over silica gel
Cipro ciprofloxacin
Cy cyclohexyl
DAD diode array detection
dba dibenzylideneacetone
DCC dicyclohexylcarbodiimide
DCM dichloromethane
DEA diethylamine
DIBAH diisobutylaluminium hydride
DMAP dimethylaminopyridine
DME 1,2-dimethoxyethane
DMF N,N-dimethylformamide
DMSO dimethylsulfoxide
EA ethyl acetate
EDC N-(3-dimethylaminopropyl)-N'-ethylcarbodiimide hydrochloride
EL SD evaporative light scattering detector
ESI electron spray ionisation
eq. equivalent
Et ethyl
Et$_2$O diethyl ether
EtOH ethanol Gly glycine
HATU O-(7-azabenzotriazol-1-yl)-N,N,N',N'-tetramethyluronium hexafluorophosphate
Hept heptane
Hex hexane
HOBT hydroxybenzotriazole
HPLC high pressure liquid chromatography
iPr iso-propyl
IT internal temperature
LC liquid chromatography
Me methyl
MeCN acetonitrile
MeOH methanol
MS mass spectroscopy
Ms methylsulfonyl (mesyl)
nBu n-butyl
NBS N-bromosuccinimide
Nf nonafluorobutanesulfonyl
NMR Nuclear Magnetic Resonance
Ns 4-nitrobenzenesulfonyl (nosylate)
org. organic
Pd/C palladium on carbon
PE petroleum ether
PEPPSI™-Ipr [1,3-bis(2,6-diisopropylphenyl)imidazol-2-ylidene](3-chloropyridyl)palladium(II) dichloride
Ph phenyl
PPTS para-toluenesulfonic acid pyridinium salt
prep-HPLC preparative HPLC
Pyr pyridine
quant. quantitative yield
Q-phos 1,2,3,4,5-pentaphenyl-1'-(di-tert-butylphosphino)ferrocene
rt room temperature
sat. saturated
SK-CC01-A 2'-(dimethylamino)-2-biphenylyl-palladium(II) chloride dinorbornylphosphine complex
S-Phos 2-dicyclohexylphosphino-2',6'-dimethoxybiphenyl
TBAF tetra-n-butylammonium fluoride
TBDPS tert-butyldiphenylsilyl
tBu tert-butyl
tBuOH tert-butanol
TEA triethylamine
Tf trifluoromethylsulfonyl (triflyl)
TFA trifluoroacetic acid
THF tetrahydrofuran
THP tetrahydropyranyl
TLC thin layer chromatography
TMS trimethylsilyl
TMSE 2-(trimethylsilyl)ethyl
$t_R$ retention time
$T_S$ para-toluenesulfonyl
General Reaction Techniques:
General Reaction Technique 1 (hydroxamic acid Protecting Group Removal):

The protecting groups R of the hydroxamic acid ester derivatives (CONHOR) are removed as follows:
When R is THP, (2-methylpropoxy)ethyl, methoxymethyl, tBu, COOtBu or COtBu: by acidic treatment with e.g. TFA or HCl in an org. solvent such as DCM, dioxane, Et$_2$O or MeOH between 0° C. and rt or by treatment with pyridiniumpara-toluenesulfonate in EtOH between rt and 80° C.;
When R is trityl: by treatment with diluted acid such as citric acid or HCl in an org. solvent such as MeOH or DCM;
When R is benzyl: by hydrogenation using general reaction technique 8;
When R is TMSE: by using fluoride anion sources such as BF$_3$.etherate complex in MeCN at 0° C., TBAF in THF between 0° C. and +40° C. or HF in MeCN or water between 0° C. and +40° C., or using acidic conditions such as AcOH in THF/MeOH or HCl in MeOH;
When R is allyl: by treatment with Pd(PPh$_3$)$_4$ in a solvent such as MeOH in presence of K$_2$CO$_3$ or a scavenger such as dimedone, morpholine or tributyltin hydride;
When R is COMe: by treatment with diluted NaOH or Na$_2$CO$_3$ in a solvent such as MeOH.

Further general methods to remove hydroxamic acid protecting groups have been described in T. W. Greene & P. G. M. Wuts, *Protecting Groups in Organic Synthesis*, 3$^{rd}$ Ed (1999), 23-147 (Publisher: John Wiley and Sons, Inc., New York, N.Y.).

General Reaction Technique 2 (amide Coupling);

The carboxylic acid is reacted with the hydroxylamine derivative in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and 60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and 60° C. Further activating agents can be found in R. C. Larock, *Comprehensive Organic Transformations. A guide to Functional Group Preparations*, 2$^{nd}$ Edition (1999), section nitriles, carboxylic acids and derivatives, p. 1941-1949 (Wiley-VC; New York, Chichester, Weinheim, Brisbane, Singapore, Toronto).

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as K$_2$CO$_3$, Cs$_2$CO$_3$, K$_3$PO$_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as Pd(PPh$_3$)$_4$. These catalysts can also be prepared in situ from a common palladium source such as Pd(OAc)$_2$ or Pd$_2$(dba)$_3$ and a ligand such as trialkylphosphines (e.g. PCy$_3$ or P(tBu)$_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (alkyne-alkyne Cross Coupling or alkyne-haloalkyne Cross Coupling):

An alkyne derivative is coupled with a second alkyne or a haloalkyne derivative, using a catalytic amount of a palladium salt, an org. base such as TEA and a catalytic amount of a copper derivative (usually copper iodide) in a solvent such as DMF at a temperature from 20 to 100° C. (see Sonogashira, K. in *Metal-Catalyzed Reactions*, Diederich, F., Stang, P. J., Eds.; Wiley-VCH: New York (1998)). Alternatively, the alkyne-haloalkyne cross coupling reaction can be performed using only a catalytic amount of copper derivative in presence of aqueous hydroxylamine and a base such as piperidine or pyrrolidine (see Chodkiewicz and Cadiot, C. *R. Hebd. Seances Acad. Sci.* (1955), 241, 1055-1057).

General Reaction Technique 5 (Transformation of an ester into an acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in T. W. Greene & P. G. M. Wuts, *Protecting Groups in Organic Synthesis*, 3$^{rd}$ Ed. (1999), 369-441 (Publisher: John Wiley and Sons, Inc., New York, N.Y.).

General Reaction Technique 6 (alcohol Activation):

The alcohol is reacted with MsCl, TfCl, BsCl, NfCl, NsCl or TsCl in the presence of a base such as TEA in a dry aprotic solvent such as Pyr, THF or DCM between −30° C. and +50° C. In the case of the triflate or mesylate, Tf$_2$O or Ms$_2$O can also be used.

General Reaction Technique 7 (Formation of iodo, chloro or bromo Derivatives):

The sulfonates obtained using general reaction technique 6 can be reacted with a sodium halogenide such as NaI or NaBr in MeCN or DMF between 40° C. and 120° C., delivering the corresponding halogenated derivatives. Alternatively, the corresponding bromides or chlorides can also be obtained by reaction of the corresponding alcohol derivatives with PBr$_3$ or PCl$_3$ respectively.

General Reaction Technique 8 (Hydrogenation of a Double Bond):

The unsaturated derivative dissolved in a solvent such as MeOH, EA or THF is hydrogenated over a noble metal catalyst such as Pd/C or PtO$_2$, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups R$^1$, R$^2$, R$^3$, M, M$^A$, M$^B$, A, R$^{1A}$, R$^{2A}$, R$^{3A}$ and R$^{1B}$ are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example T. W. Greene and P. G. M. Wuts, *Protective Groups in Organic Synthesis*, 3$^{rd}$ Ed. (1999), Wiley-Interscience).

The compounds of formula I can be obtained by deprotecting a compound of formula II

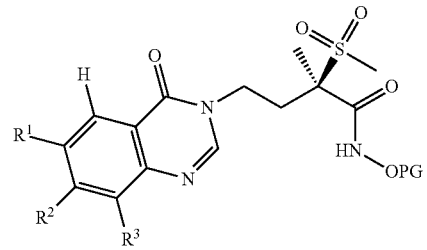

II wherein R$^1$, R$^2$ and R$^3$ have the same meanings as in formula I and PG represents THP, TMSE, benzyl, trityl, (2-methylpropoxy)ethyl, methoxymethyl, allyl, tBu, acetyl, COOtBu or COtBu using general reaction technique 1. The reaction can also be performed with racemic material and the (R) enantiomer can be obtained by chiral HPLC separation.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-Ol (R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II:

The compounds of formula II can be obtained by:

a) Reacting a Compound of Formula III

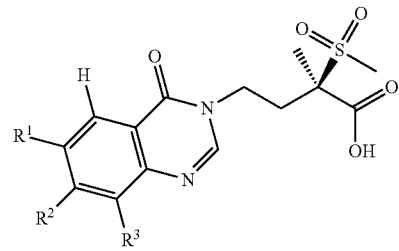

III wherein R$^1$, R$^2$ and R$^3$ have the same respective meanings as in formula I with a compound of formula IV

H$_2$N—OPG    IV wherein PG has the same meaning as in formula II using general reaction technique 2 (this reaction can also be performed with racemic compound of formula III and the (R)-enantiomer can then be obtained by chiral HPLC separation of the reaction product), whereby functional groups (e.g. amino or hydroxy) present on R² that would be incompatible with the coupling conditions mentioned in general reaction technique 2 can be protected (as carbamates or THP/silyl ethers respectively) before performing said reaction and deprotected after performing said reaction; or b) reacting a boron derivative of formula V

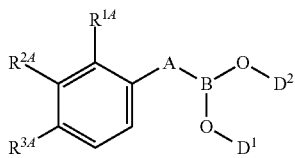

V wherein $R^{1A}$, $R^{2A}$ and $R^{3A}$ have the same respective meanings as in formula I, A represents a bond and $D^1$ and $D^2$ represent H, ($C_1$-$C_4$)alkyl such as methyl or ethyl or $D^1$ and $D^2$ together represent $CH_2C(Me)_2CH_2$ or $C(Me)_2C(Me)_2$ with a compound of formula VI

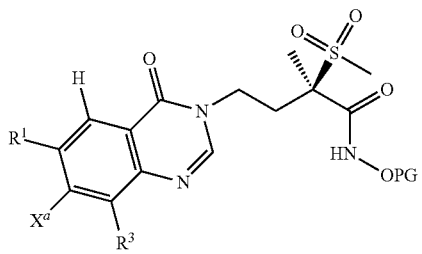

VI wherein $R^1$ and $R^3$ have the same respective meanings as in formula I, $X^a$ represents a halogen such as bromine or iodine and PG has the same meaning as in formula II, using general reaction technique 3 (this reaction can also be performed with racemic compound of formula VI and the (R)-enantiomer can then be obtained by chiral HPLC separation of the reaction product); or c) Reacting a Compound of Formula VII

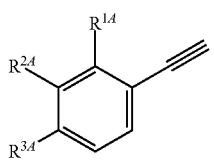

VII wherein $R^{1A}$, $R^{2A}$ and $R^{3A}$ have the same respective meanings as in formula I, with a compound of formula VI as defined in section b) above wherein $X^a$ represents iodine, using general reaction technique 4 (this reaction can also be performed with racemic compound of formula VI and the (R)-enantiomer can then be obtained by chiral HPLC separation of the reaction product); or d) Reacting a Compound of Formula VIII

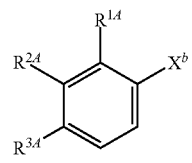

VIII wherein $R^{1A}$, $R^{2A}$ and $R^{3A}$ have the same respective meanings as in formula I and $X^b$ represents iodine or bromine (and preferably iodine), with a compound of formula VIa

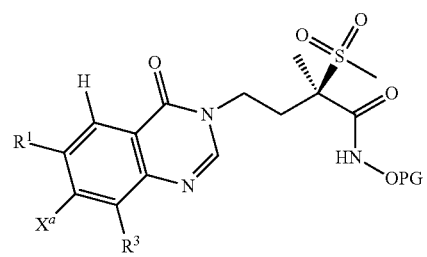

VIa wherein $R^1$ and $R^3$ have the same respective meanings as in formula I, $X^a$ represents ethynyl and PG has the same meaning as in formula II, using general reaction technique 4 (this reaction can also be performed with racemic compound of formula VIa and the (R)-enantiomer can then be obtained by chiral HPLC separation of the reaction product); or e) Reacting a Compound of Formula IX

IX wherein $R^{1B}$ has the same meaning as in formula I and $X^c$ represents iodine or bromine, with a compound of formula VIa as defined in section d) above, using general reaction technique 4 (this reaction can also be performed with racemic compound of formula VIa and the (R)-enantiomer can then be obtained by chiral HPLC separation of the reaction product).

Preparation of the Synthesis Intermediates of Formulae III, IV, V, VI, VIa, VII, VIII and IX:

Compounds of Formula III:

The compounds of formula III can be prepared as summarised in Scheme 1 hereafter.

Scheme 1

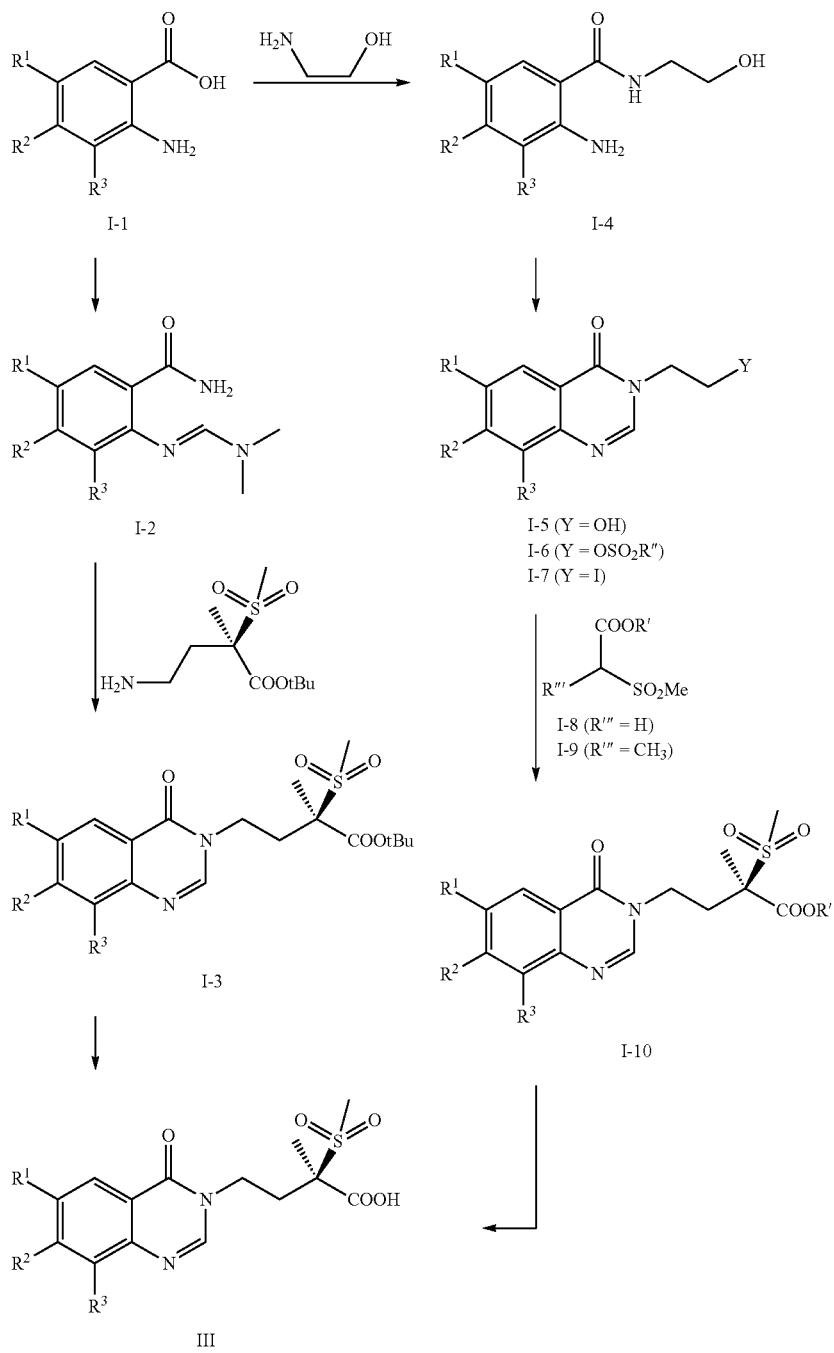

In Scheme 1, $R^1$, $R^2$ and $R^3$ have the same respective meanings as in formula I, R' represents ($C_1$-$C_5$)alkyl, allyl or benzyl, R'' represents alkyl, $CF_3$ or tolyl and R''' represents H or $CH_3$. The reactions can also be performed with racemic material and the (R)-enantiomer can be obtained by chiral HPLC separation at any step when suitable.

The derivatives of formula III can be obtained (Scheme 1) from the compounds of formula I-3 or from the compounds of formula I-10 wherein R' is alkyl using general reaction technique 5. The acids of formula I-1 can be reacted with dimethylformamide dimethyl acetal in a solvent such as DMF at a temperature ranging between 60° and 100° C., especially at around 80° C., to yield the compounds of formula I-2. The latter can be subsequently reacted with tert-butyl (R)-4-amino-2-methyl-2-(methylsulfonyl)butanoate in phenol at a temperature ranging between 60° C. and 100° C. to give compounds of formula I-3. Alternatively, the compounds of formula I-10 can be prepared from the compounds of formula I-5. The acids of formula I-1 can be reacted with ethanolamine using general reaction technique 2 to yield the compounds of formula I-4 that are reacted with a formaldehyde synthetic equivalent, such as dimethylformamide dimethyl acetal, in the presence of a catalytic amount of an acid such as HCl, in a solvent such as NMP at a temperature ranging between 60° C. and 100° C.; the compounds of formula I-5 thus obtained can be sequentially transformed into the derivatives of formulae I-6 and I-7 using general reaction techniques 6 and 7 respectively. The compounds of formula I-7 can be reacted either with the compounds of formula I-8 in the presence of NaH, followed by alkylation with MeI in the presence of NaH, or directly with the compounds of formula I-9 in the presence of NaH, affording the compounds of formula I-10.

Compounds of Formula IV:

The compounds of formula IV are commercially available (PG=THP, tBu, COOtBu or allyl) or can be prepared according to WO 2010/060785 (PG=(2-methylpropoxy)ethyl) or Marmer and Maerker, *J. Org. Chem.* (1972), 37, 3520-3523 (PG=COtBu).

available or can be prepared according to Sleveland et al., *Organic Process Research & Development* (2012), 16, 1121-1130 starting from tri(($C_1$-$C_2$)alkyl)borate and the corresponding commercially available bromo derivatives (optionally followed by acidic hydrolysis). The compounds of formula V wherein A represents a bond and $D^1$ and $D^2$ together represent $CH_2C(Me)_2CH_2$ or $C(Me)_2C(Me)_2$ are commercially available or can be prepared according to WO 2012/093809, starting from bis(pinacolato)diborane or 5,5-dimethyl-1,3,2-dioxaborinane (both commercially available) with the corresponding commercially available derivatives of formula VIII wherein $X^b$ is bromine.

Compounds of Formulae VI and VIa:

The compounds of formulae VI and VIa can be prepared as summarised in Scheme 2 hereafter.

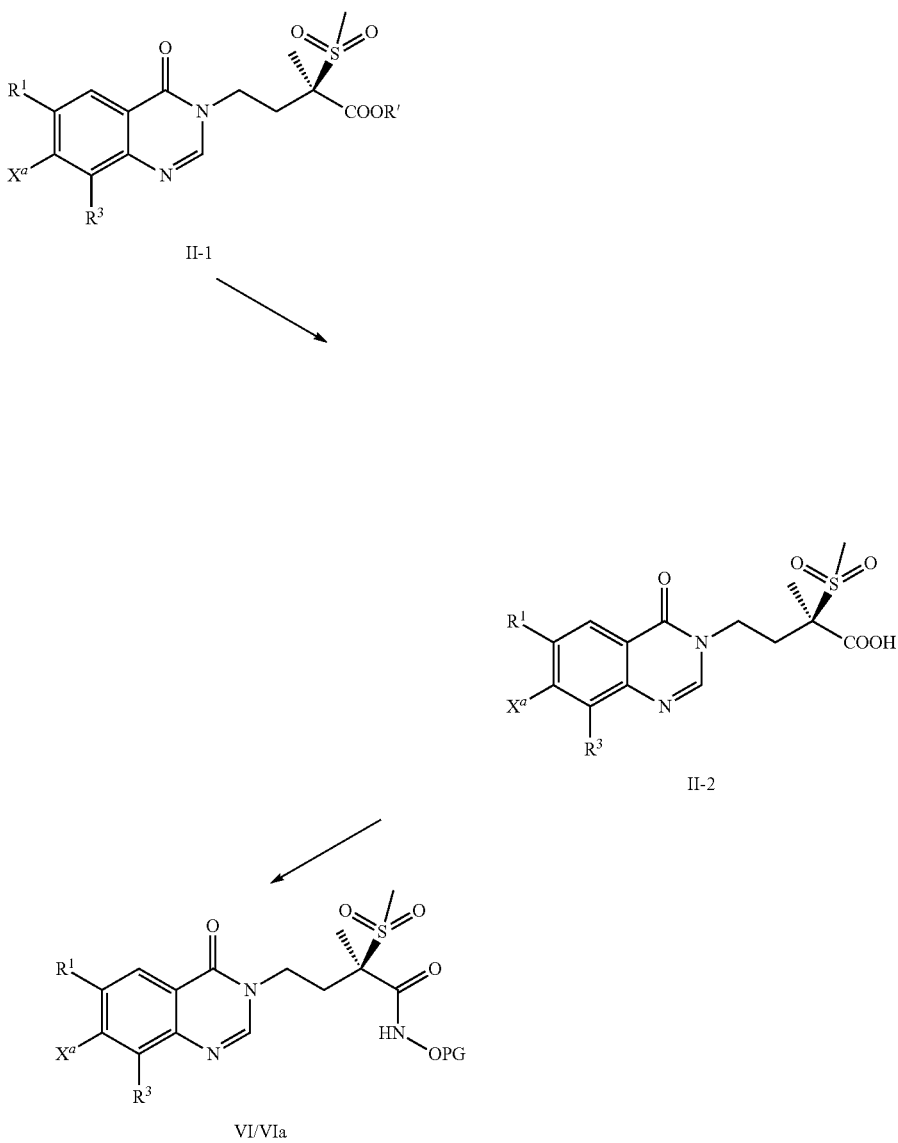

Compounds of Formula V:

The compounds of formula V wherein A is a bond and $D^1$ and $D^2$ each represent H or ($C_1$-$C_2$)alkyl are commercially In Scheme 2, $R^1$ and $R^3$ have the same respective meanings as in formula I, R' represents ($C_1$-$C_5$)alkyl, allyl or benzyl, $X^a$ represents a halogen (such as iodine or bromine)

or ethynyl and PG has the same meaning as in formula II. The reactions can also be performed with racemic material and the (R)-enantiomer can be obtained by chiral HPLC separation at any step when suitable.

The derivatives of formula II-1 can be transformed (Scheme 2) into the carboxylic acid derivatives of formula II-2 using general reaction technique 5 and further reacted with the compounds of formula IV using general reaction technique 2, thus affording the compounds of formula VI ($X^a$=halogen) or VIa ($X^a$=ethynyl). The compounds of formula VIa can also be obtained by reacting the corresponding compounds of formula VI wherein X' is Br or I with TMS-acetylene using general reaction technique 4, the TMS group being then removed by treatment with TBAF in THF or by treatment with $K_2CO_3$ in MeOH.

Compounds of Formula VII:

The compounds of formula VII are commercially available or can be prepared as summarised in Scheme 3 hereafter.

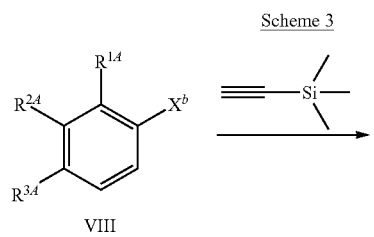

Scheme 3

VIII

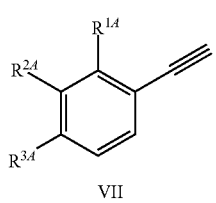

VII

In Scheme 3, $R^{1A}$, $R^{2A}$ and $R^{3A}$ have the same respective meanings as in formula I and $X^b$ represents a halogen such as bromine or iodine.

The derivatives of formula VIII wherein $X^b$ represents bromine can be transformed (Scheme 3) into the corresponding derivatives wherein $X^b$ represents iodine by reaction with NaI in the presence of CuI and trans-N,N'-dimethylcyclohexanediamine. The resulting compounds of formula VIII wherein $X^b$ represents iodine can be reacted with trimethylsilylacetylene in the presence of CuI and $PdCl_2(PPh_3)_2$, followed by treatment with an inorganic base such as $K_2CO_3$ in an appropriate alcoholic solvent such as MeOH, or by treatment with TBAF in THF, affording the derivatives of formula VII.

Compounds of Formula VIII:

The compounds of formula VIII wherein $X^b$ represents bromine are commercially available or can be prepared by standard methods known to one skilled in the art. The compounds of formula VIII wherein $X^b$ represents iodine can be obtained from the corresponding bromine derivatives by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at 150° C.

Compounds of Formula IX:

The compounds of formula IX wherein $X^c$ represents iodine can be prepared by iodination of the corresponding compounds wherein $X^c$ would be H with iodine in the presence of an inorganic base such as KOH.

Other Synthesis Intermediates and Starting Materials:

The compounds of formulae I-1, I-8 and I-9 are commercially available or can be prepared by standard methods known to one skilled in the art.

Tert-butyl (R)-4-amino-2-methyl-2-(methylsulfonyl)butanoate can be prepared in analogy to the methods described in the section entitled "EXAMPLES" hereafter (see Preparations A and G), or by standard methods known to one skilled in the art.

The compounds of formula II-1 wherein $X^a$ represents bromine can be prepared as summarised in Scheme 4 hereafter.

Scheme 4

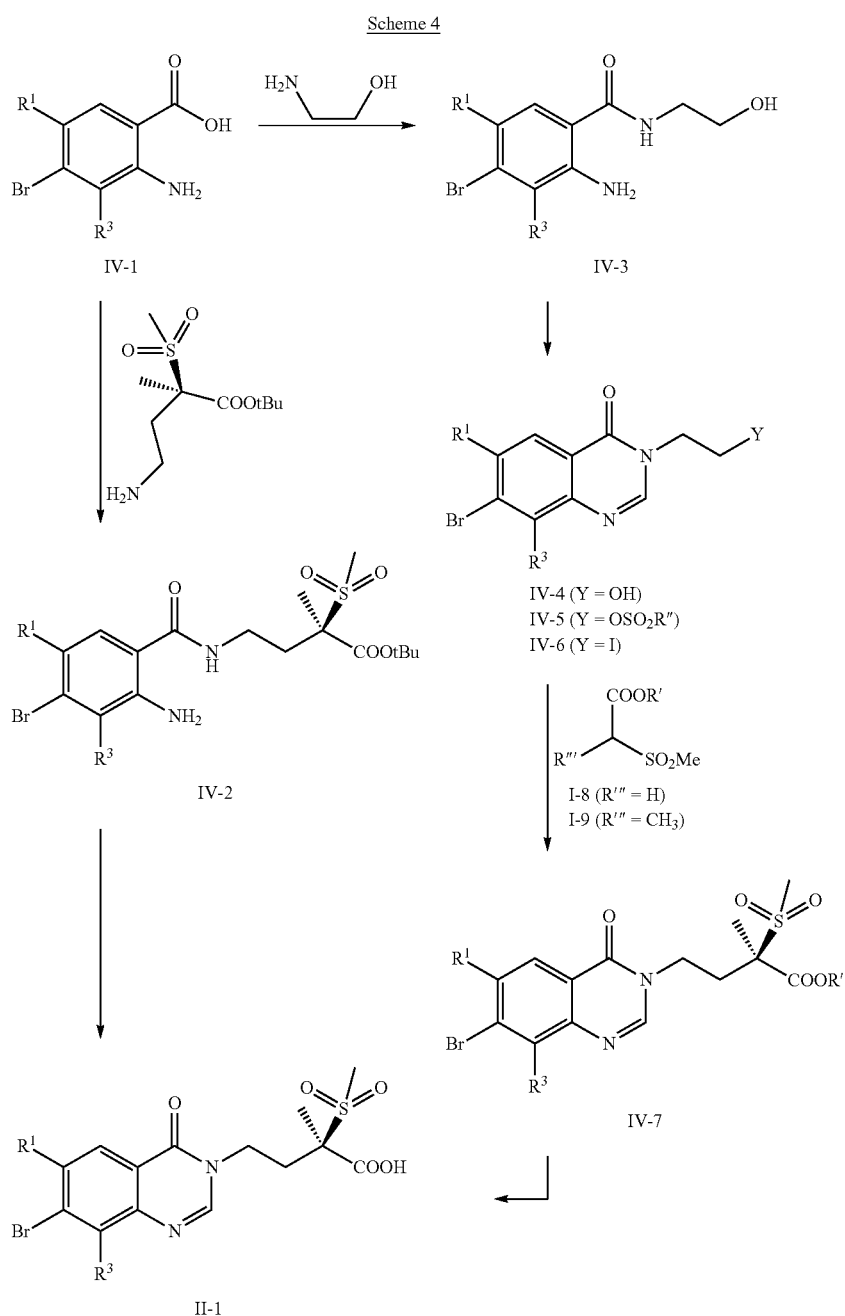

In Scheme 4, $R^{1A}$, $R^{2A}$ and $R^{3A}$ have the same respective meanings as in formula I, R' represents $(C_1\text{-}C_5)$alkyl, allyl or benzyl, R'' represents alkyl, $CF_3$ or tolyl and R''' represents H or $CH_3$. The reactions can also be performed with racemic material and the (R)-enantiomer can be obtained by chiral HPLC separation at any step when suitable.

The acids of formula IV-1 can be reacted (Scheme 4) with tert-butyl (R)-4-amino-2-methyl-2-(methylsulfonyl)butanoate using general reaction technique 2 to yield the compounds of formula IV-2. The latter can be transformed into the compounds of formula II-1 wherein $X^a$ represents bromine by reaction with a formaldehyde synthetic equivalent, in particular dimethylformamide dimethyl acetal, in the presence of a catalytic amount of an acid such as HCl, in a solvent such as NMP at a temperature ranging between 60° C. and 100° C. Alternatively, the acids of formula IV-1 can be reacted (Scheme 4) with 2-aminoethan-1-ol using general reaction technique 2 to afford the compounds of formula IV-3. The latter can be reacted with a formaldehyde synthetic equivalent, in particular dimethylformamide dimethyl acetal, in the presence of a catalytic amount of an acid such as HCl, in a solvent such as NMP at a temperature ranging between 60° C. and 100° C. to afford the compounds of formula IV-4. The latter can be sequentially transformed into the derivatives of formulae IV-5 and IV-6 using general reaction techniques 6 and 7 respectively. The compounds of formula IV-6 can then be reacted either with the compounds of formula I-8 in the presence of NaH, followed by alkylation with MeI in the presence of NaH, or directly with the compounds of formula I-9 in the presence of NaH, affording the compounds of formula II-1 wherein $X^a$ represents bromine.

The compounds of formula II-1 wherein $X^a$ represents an ethynyl group can be prepared from the compounds of formula II-1 wherein $X^a$ represents bromine by reaction with NaI in the presence of CuI and trans-N,N'-dimethylcyclohexanediamine. The resulting compounds of formula II-1 wherein $X^a$ represents iodine can be reacted with trimethylsilylacetylene in the presence of CuI and $PdCl_2(PPh_3)_2$, followed by treatment with an inorganic base such as $K_2CO_3$ in an appropriate alcoholic solvent such as MeOH, or by treatment with TBAF in THF.

The compounds of formula IV-1 are commercially available or can be prepared by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
Column: Zorbax SB-Aq, 30.5 µm, 4.6×50 mm;
Injection volume: 1 µL;
Column oven temperature: 40° C.;
Detection: UV 210 nm, ELSD and MS;
MS ionization mode: ESI+;
Eluents: A: $H_2O$+0.04% TFA; and B: MeCN;
Flow rate: 40.5 mL/min;
Gradient: 5% B to 95% B (0.0 min 1.0 min), 95% B (1.0 min 1.45 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
Method 1:
Column: Waters Atlantis T3 OBD, 10 µm, 30×75 mm;
Flow rate: 75 mL/min;
Eluents: A: $H_2O$+0.1% HCOOH; B: MeCN+0.1% HCOOH;
Gradient: 90% A to 5% A (0.0 min 4.0 min), 5% A (4.0 min 6.0 min).
Method 2:
Column: Waters Atlantis T3 OBD, 10 µm, 30×75 mm;
Flow rate: 75 mL/min;
Eluents: A: $H_2O$+0.5% HCOOH; B: MeCN;
Gradient: 95% A to 5% A (0.0 min 4.0 min), 5% A (4.0 min 6.0 min).

Besides, semi-preparative chiral HPLCs were performed using the conditions herafter.
Semi-preparative Chiral HPLC Method A:
The semi-preparative chiral HPLC is performed on a Daicel ChiralPak AZ-H column (20×250 mm, 5 µM) using the eluent mixture, flow rate and detection conditions indicated between brackets in the corresponding experimental protocol. The retention times are obtained by elution of analytical samples on a Daicel ChiralPak AZ-H column (4.6×250 mm, 5 µM) using the same eluent mixture with the flow rate indicated between brackets in the corresponding experimental protocol.
Semi-preparative Chiral HPLC Method B:
The semi-preparative chiral HPLC is performed on a Daicel ChiralPak AY-H column (20×250 mm, 5 µM) using the eluent mixture, flow rate and detection conditions indicated between brackets in the corresponding experimental protocol. The retention times are obtained by elution of analytical samples on a Daicel ChiralPak AY-H column (4.6×250 mm, 5 µM) using the same eluent mixture with the flow rate indicated between brackets in the corresponding experimental protocol.
Semi-preparative Chiral HPLC Method C:
The semi-preparative chiral HPLC is performed on a Daicel ChiralCel AS-H column (30×250 mm; 5 µM) using the eluent mixture, flow rate and detection conditions indicated between brackets in the corresponding experimental protocol. The retention times are obtained by elution of analytical samples on a Daicel ChiralCel AS-H column (4.6×250 mm; 5 µM) using the same eluent mixture with the flow rate indicated between brackets in the corresponding experimental protocol.
Procedures:
Procedure A:
A mixture of the bromo derivative (1.63 mmol), the phenylboronic acid or boronate ester derivative (1.8 mmol), $K_2CO_3$ (0.34 g; 2.4 mmol) and $Pd(PPh_3)_4$ (0.19 g; 0.16 mmol) is flushed with nitrogen for 15 min. Dioxane (6 mL) and water (1.5 mL) are added and the mixture is refluxed for 1 h. After cooling, water (15 mL) and EA (20 mL) are added and the two layers are separated. The aq. layer is extracted with EA (2×20 mL) and the combined org. layers are washed with brine, dried over $MgSO_4$ and concentrated to dryness. The residue is then purified by CC (Hept-EA).
Procedure B:
To the THP-protected hydroxamic acid derivative (0.119 mmol) in water (0.745 mL) was added TFA (0.357 mL, 4.62 mmol). After one hour stirring at rt, the mixture was directly purified by prep-HPLC using a suitable method.

Procedure C:

To a solution of the THP-protected hydroxamic acid derivative (0.84 mmol) in dioxane (3.6 mL) and water (0.8 mL) is added PPTS (0.12 g; 0.48 mmol). The reaction mixture is stirred at 70° C. for 2 h. The reaction is cooled to rt and concentrated to dryness. The residue is then purified by CC (DCM-MeOH).

Procedure D:

To the THP-protected hydroxamic acid derivative (0.02 mmol) in EtOH (3 mL) is added PPTS (0.025 g; 0.03 mmol). The mixture is stirred at 80° C. for 2 h, cooled to rt and directly purified by CC (DCM-MeOH) or by prep-HPLC using a suitable method.

Procedure E:

CuI (0.2 mmol), PdCl$_2$(PPh$_3$)$_2$ (0.1 mmol), the bromo derivative (1 mmol) and the terminal alkyne derivative (1.0 to 1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure F:

CuI (0.2 mmol), PdCl$_2$(PPh$_3$)$_2$ (0.1 mmol), the terminal alkyne derivative (1 mmol) and the iodo derivative (1.0 to 1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

Procedure G:

CuI (0.2 mmol), PdCl$_2$(PPh$_3$)$_2$ (0.1 mmol), the terminal alkyne derivative (1 mmol) and the halo-alkyne derivative (1.5 mmol) are introduced in a two-necked round flask. The atmosphere is flushed with nitrogen during 30 min, then degassed THF (5 mL) and degassed TEA (2.5 mmol) are added. The suspension is stirred under nitrogen atmosphere at 50° C. for 45 min. After concentration to dryness, the residue is then purified by CC (Hept-EA).

PREPARATIONS

Preparation A rac-tert-butyl 4-amino-2-methyl-2-(methylsulfonyl)butanoate

A.i. Rac-tert-butyl 2-(methylsulfonyl)propanoate

To a suspension of sodium methanesulfinate (15.63 g; 153 mmol) in tBuOH (50 mL) was added at rt and in one portion tert-butyl 2-bromopropionate (23.8 mL, 139 mmol). The mixture was refluxed overnight. The mixture was cooled down at rt and the solvent was removed under reduced pressure. The residue was taken up in EA (200 mL), filtered through Celite and the Celite was rinsed with EA (200 mL). The filtrate was concentrated to dryness to afford the title product as a white solid (28.4 g; 98% yield).

$^1$H NMR (d6-DMSO) δ: 4.24 (q, J=7.2 Hz, 1H); 3.11 (s, 3H); 1.45 (s, 9H); 1.40 (d, J=7.2 Hz, 3H).

A.ii. Rac-tert-butyl 4-bromo-2-methyl-2-(methylsulfonyl)butanoate:

To an ice-chilled suspension of NaH (8.95 g, 224 mmol) in DMF (250 mL) was added a solution of intermediate A.i (23.3 g, 112 mmol) in DMF (50 mL). The mixture was stirred at 0° C. for 10 min and at rt for 30 min. 1,2-dibromoethane (29.3 mL, 336 mmol) was added to the mixture and it was stirred at 70° C. overnight. Water was added. Then, the mixture was extracted three times with EA. The combined org. layers were washed with brine, dried over MgSO$_4$ and concentrated to dryness. The crude residue was purified by CC (Hept-EA) to afford the desired product as a yellow oil (16.56 g; 47% yield).

$^1$H NMR (d$_6$-DMSO) δ: 3.70-3.60 (m, 1H); 3.45-3.35 (m, 1H); 3.11 (s, 3H); 2.71-2.59 (m, 1H); 2.42-2.31 (m, 1H); 1.48 (s, 3H); 1.45 (s, 9H).

MS (ESI, m/z): no mass detected for C$_{10}$H$_{19}$O$_4$BrS; t$_R$=0.84 min.

A.iii. Rac-tert-butyl 4-azido-2-methyl-2-(methylsulfonyl)butanoate:

A mixture of intermediate A.ii (14.6 g; 32.4 mmol) and NaN$_3$ (7.93 g; 121 mmol) in DMF (160 mL) was stirred at 80° C. overnight. Water and EA were added and the phases were separated. The aq. layer was extracted twice with EA. The combined org. layers were washed with brine, dried over MgSO$_4$ and concentrated to dryness to afford the title product as a white solid (14 g; quant.).

$^1$H NMR (d6-DMSO) δ: 3.60-3.66 (m, 1H); 3.29-3.35 (overlapped m, 1H); 3.11 (s, 3H); 2.43-2.50 (overlapped m, 1H); 1.97-2.04 (m, 1H); 1.46 (s, 9H); 1.44 (s, 3H).

A.iv. Rac-tert-butyl 4-amino-2-methyl-2-(methylsulfonyl)butanoate:

To a solution of intermediate A.iii (14 g; 33.8 mmol) in THF (200 mL) was added PPh$_3$ (14.4 g; 54.3 mmol). The mixture was stirred at 60° C. for 1 h and water (70.4 mL) was added. The mixture was stirred at 60° C. for 1.5 h. The volatiles were removed under reduced pressure and the residue was diluted with DCM-MeOH 9-1 and water. The aq. layer was extracted several times with DCM-MeOH 9-1. The combined org. layers were washed with HCl (0.5M). Org. layer was removed and the pH of the aq. layer was adjusted above 10 with NaOH (0.5 M), then extracted several times with DCM/MeOH 8:2. The org. layers were combined, washed with brine, dried over MgSO$_4$ and concentrated under reduced pressure to afford the title product as a colourless oil (6.222 g; 73% yield).

$^1$H NMR (d6-DMSO) δ: 3.06 (s, 3H); 2.63-2.75 (m, 1H); 2.40-2.53 (overlapped m, 1H); 2.16-2.28 (m, 1H); 1.74-1.85 (m, 1H); 1.44 (s, 9H); 1.40 (s, 3H).

Preparation B rac-4-(7-bromo-4-oxoquinazolin-3(4H)-yl)-2-methyl-2-(methylsulfonyl)-N-((tetrahydro-2H-1-pyran-2-yl)oxy)butanamide:

B.i. Methyl (E)-4-bromo-2-(((dimethylamino)methylene)amino)benzoate:

A solution of methyl 2-amino-4-bromobenzoate (1.01 g; 4.28 mmol) in dry DMF (2.6 mL) was treated with dimethylformamide dimethyl acetal (3.6 mL; 25.5 mmol). The mixture was heated at 80° C. for 3 h. The mixture was concentrated to dryness to afford the title compound as a brown oil (1.224 g; quant.).

¹H NMR (d6-DMSO) δ: 7.71 (s, 1H); 7.40 (d, J=8.2 Hz, 1H); 7.17 (d, J=1.8 Hz, 1H); 7.13 (dd, J=1.8, 8.2 Hz, 1H); 3.73 (s, 3H); 3.02 (s, 3H); 2.89 (s, 3H).

MS (ESI, m/z): 287.0 [M+H$^+$] for $C_{11}H_{13}N_2O_2Br$; $t_R$=0.57 min.

B.ii. Rac-tert-butyl 4-(7-bromo-4-oxoquinazolin-3 (4H)-yl)-2-methyl-2-(methylsulfonyl)butanoate:

A mixture of intermediate B.i (1.22 g; 4.28 mmol), the compound of Preparation A (1.19 g, 4.71 mmol) and phenol (2.39 g; 25.4 mmol) was stirred at 80° C. for 16 h. The reaction mixture was purified by CC (Hept-EA) to afford the title compound as a white solid (1.49 g; 76% yield).

¹H NMR (d6-DMSO) δ: 8.46 (s, 1H); 8.08 (d, J=8.5 Hz, 1H); 7.91 (d, J=1.8 Hz, 1H); 7.72 (dd, J=1.8, 8.5 Hz, 1H); 3.96-4.12 (m, 2H); 3.14 (s, 3H); 2.45-2.60 (overlapped m, 1H); 2.16-2.26 (m, 1H); 1.57 (s, 3H); 1.43 (s, 9H).

MS (ESI, m/z): 459.0 [M+H$^+$] for $C_{18}H_{23}N_2O_5BrS$; $t_R$=0.87 min.

B.iii. Rac-4-(7-bromo-4-oxoquinazolin-3(4H)-yl)-2-methyl-2-(methylsulfonyl)butanoic acid hydrochloride:

To a mixture of intermediate B.ii (1.49 g; 3.24 mmol) in 4N HCl in dioxane (21 mL) was added water (1.5 mL). The mixture was stirred at rt for 18 h. The reaction mixture was concentrated to dryness and co-evaporated twice with Et$_2$O to give the title acid as a white solid (1.45 g; quant.).

¹-H NMR (d6-DMSO) δ: 8.45 (s, 1H); 8.06 (d, J=8.5 Hz, 1H); 7.91 (d, J=1.8 Hz, 1H); 7.72 (dd, J=1.8, 8.5 Hz, 1H); 3.99-4.17 (m, 2H); 3.14 (s, 3H); 2.44-2.64 (overlapped m, 1H); 2.16-2.28 (m, 1H); 1.59 (s, 3H).

MS (ESI, m/z): 403.1 [M+H$^+$] for $C_{14}H_{16}N_2O_5BrClS$; $t_R$=0.66 min.

B.iv. Rac-4-(7-bromo-4-oxoquinazolin-3(4H)-yl)-2-methyl-2-(methylsulfonyl)-N-((tetrahydro-2H-pyran-2-yl)oxy)butanamide:

To a solution of intermediate B.iii (1.425 g; 3.24 mmol) in DMF (17 mL) were added successively HOBT (0.925 g; 6.64 mmol), TEA (1.7 mL; 12.2 mmol), THPONH$_2$ (0.692 g; 5.79 mmol) and EDC.HCl (1.06 g; 5.48 mmol). The reaction mixture was stirred at rt for 18 h. The reaction mixture was concentrated in vacuo and partitioned between water (20 mL) and EA (30 mL). The org. layer was washed with water (25 mL), aq. 15% NaHSO$_4$ (25 mL), aq. sat. NaHCO$_3$ (25 mL) and brine (25 mL). The org. layer was dried over MgSO$_4$ and concentrated to dryness to give the title compound as a beige solid (1.58 g; 97% yield).

¹H NMR (d6-DMSO) δ (mixture of stereoisomers): 11.40 (s, 1H); 8.38 (d, J=6.7 Hz, 1H); 8.07 (d, J=8.5 Hz, 1H); 7.91 (d, J=1.6 Hz, 1H); 7.72 (dd, J=1.6, 8.5 Hz, 1H); 4.87-4.95 (m, 1H); 3.81-4.20 (m, 3H); 3.41-3.54 (m, 1H); 3.08 (s, 1.5H); 3.05 (s, 1.5H); 2.44-2.66 (overlapped m, 1H); 2.14-2.31 (m, 1H); 1.46-1.74 (overlapped m, 6H); 1.60 (s, 1.5H); 1.61 (s, 1.5H).

MS (ESI, m/z): 502.1 [M+H$^+$] for $C_{19}H_{24}N_3O_6BrS$; $t_R$=0.76 min.

Preparation C 4-(3-(3-fluoro-4-(4,4,5,5-tetramethyl-1,3,2-dioxaborolan-2-yl)phenoxy)propyl)morpholine C.i.
4-(3-(4-bromo-3-fluorophenoxy)propyl)morpholine To a solution of 4-(3-chloropropyl)morpholine (1 g; 6.11 mmol; commercial) and 4-bromo-3-fluorophenol (1.17 g; 6.11 mmol) in DMF (7.6 mL) were added Cs$_2$CO$_3$ (6.05 g; 18.4 mmol) and NaI (0.932 g; 6.16 mmol). The suspension was stirred at 100° C. for 17 h. After cooling to rt, the solids were filtered off, and the filtrate was diluted with water (5 mL) and EA (10 mL). The aq. layer was extracted twice with EA (2×10 mL) and the combined org. layers were washed with 1M NaOH (15 mL), dried over MgSO$_4$ and concentrated to dryness to afford the title product as a beige solid (1.53 g; 79% yield).

¹H NMR (d6-DMSO) δ: 7.53 (t, J=8.5 Hz, 1H); 7.00 (dd, J=2.8, 11.1 Hz, 1H); 6.75 (ddd, J=0.8, 2.8, 8.9 Hz, 1H); 4.01 (t, J=6.4 Hz, 2H); 3.49-3.57 (m, 4H); 2.27-2.41 (m, 6H); 1.84 (q, J=6.5 Hz, 2H).

MS (ESI, m/z): 320.1 [M+H$^+$] for $C_{13}H_{17}NO_2BrF$; $t_R$=0.59 min.

C.ii. 4-(3-(3-fluoro-4-(4,4,5,5-tetramethyl-1,3,2-dioxaborolan-2-yl)phenoxy)propyl)morpholine In a sealed tube were introduced intermediate C.i (0.2 g; 0.63 mmol), bis(pinacolato)diboron (0.179 g; 0.70 mmol), bis(diphenylphosphino)ferrocene palladium (II) dichloride (0.031 g; 0.038 mmol) and potassium acetate (0.187 g; 1.89 mmol). The mixture was stirred under nitrogen for 5 min and DME (3.9 mL) was added. The mixture was heated at 150° C. for 30 min under microwave irradiation. After cooling, the reaction mixture was concentrated to dryness and the residue was purified by CC (DCM-MeOH) to afford the title product as a dark brown oil (0.269 g; quant.).

¹H NMR (d6-DMSO) δ: 7.52 (t, J=7.6 Hz, 1H); 6.67-6.77 (m, 2H); 3.96-4.06 (m, 2H); 3.51-3.57 (m, 4H); 2.28-2.41 (m, 6H); 1.84 (q, J=6.4 Hz, 2H); 1.05 (s, 12H).

MS (ESI, m/z): 366.4 [M+H$^+$] for $C_{19}H_{29}NO_4BF$; $t_R$=0.68 min.

Preparation D rac-4-(7-bromo-6-fluoro-4-oxoquinazolin-3(4H)-yl)-2-methyl-2-(methylsulfonyl)-N-((tetrahydro-2H-pyran-2-yl)oxy)butanamide D.i. Methyl 2-amino-4-bromo-5-fluorobenzoate To a solution of methyl 4-bromo-5-fluoro-2-nitrobenzoate (3.43 g; 12.3 mmol, prepared as described in WO 2010/037210) in AcOH (40 mL) was added iron powder (6.15 g; 110 mmol). The resulting reaction mixture was stirred at 90° C. for 50 min. The mixture was filtered through a Celite bed and washed with EA (20 mL). The filtrate was evaporated under reduced pressure and co-evaporated three times with cyclohexane (3×50 mL) to give the title compound as a brownish solid (3.05 g; quant.).

¹H NMR (d6-DMSO) δ: 7.53 (d, J=9.7 Hz, 1H); 7.13 (d, J=6.1 Hz, 1H); 6.68 (s, 2H); 3.80 (s, 3H).

D.ii. Rac-tert-butyl 4-(7-bromo-6-fluoro-4-oxoquinazolin-3(4H)-yl)-2-methyl-2-(methylsulfonyl)butanoate:

A solution of intermediate D.i (3.05 g, 12.3 mmol) in dry DMF (7 mL) was treated with dimethylformamide dimethyl acetal (9.8 mL; 74 mmol). The mixture was heated at 80° C. for 2 h. The mixture was concentrated to dryness. To the residue were added the compound of Preparation A (0.265 g; 1.05 mmol) and phenol (0.355 g; 3.78 mmol). The mixture was stirred at 130° C. for 5 min and at 80° C. for 2.5 h. The crude mixture was purified by CC (Hept-EA) to give the title compound as a brown solid (4.55 g; 77% yield).

$^1$H NMR (d6-DMSO) δ: 8.46 (s, 1H); 8.13 (d, J=6.2 Hz, 1H); 7.99 (d, J=8.5 Hz, 1H); 4.05 (m, 2H); 3.33 (s, 2H); 2.53-2.60 (m, 1H); 2.18-2.25 (m, 1H); 1.58 (s, 3H); 1.44 (s, 9H).

MS (ESI, m/z): 477.0 [M+H$^+$] for $C_{18}H_{22}N_2O_5BrFS$; $t_R$=0.89 min.

D.iii. 4-(7-bromo-6-fluoro-4-oxoquinazolin-3(4H)-yl)-2-methyl-2-(methylsulfonyl)butanoic acid hydrochloride A mixture of intermediate D.ii (4.56 g; 9.55 mmol) in 4N HCl in dioxane (68 mL) and water (2 mL) was stirred at rt for 17 h. The reaction mixture was stirred at rt for 1.5 h. The reaction mixture was concentrated to dryness and co-evaporated twice with Et$_2$O to give the title acid as a yellow solid (4.37 g; quant.).

$^1$H NMR (d6-DMSO) δ: 8.44 (s, 1H); 8.12 (d, J=6.3 Hz, 1H); 7.98 (d, J=8.5 Hz, 1H); 4.10 (m, 2H); 2.55-2.61 (m, 1H); 2.20-2.26 (m, 1H).

MS (ESI, m/z): 421.0 [M+H$^+$] for $C_{14}H_{15}N_2O_5BrClFS$; $t_R$=0.69 min.

D.iv. Rac-4-(7-bromo-6fluoro-4-oxoquinazolin-3(4H)-yl)-2-methyl-2-(methylsulfonyl)-N-((tetrahydro-2H-pyran-2-yl)oxy)butanamide Starting from intermediate D.iii (4.37 g; 9.55 mmol) and proceeding in analogy to the Preparation B, step B.iv, the title compound was obtained, after purification by CC (Hept-EA), as a white solid (3.9 g; 78% yield).

$^1$H NMR (d6-DMSO) δ (mixture of stereoisomers): 11.44 (br. s, 0.5H); 11.43 (br. s, 0.5H); 8.38 (s, 0.5H); 8.36 (s, 0.5H); 8.13 (d, J=6.3 Hz, 1H); 7.98 (d, J=8.5 Hz, 1H); 4.92 (br. s, 0.5H); 4.88 (br. s, 0.5H); 3.98-4.16 (m, 2H); 3.86-3.96 (m, 1H); 3.47-3.53 (m, 1H); 3.08 (s, 1.5H); 3.06 (s, 1.5H); 2.55-2.64 (m, 1H); 2.16-2.25 (m, 1H); 1.62-1.71 (m, 3H); 1.62 (s, 1.5H); 1.62 (s, 1.5H); 1.49-1.56 (m, 3H).

MS (ESI, m/z): 520.1 [M+H$^+$] for $C_{19}H_{23}N_3O_6BrFS$; $t_R$=0.79 min.

Preparation E rac-4-(7-ethynyl-4-oxoquinazolin-3(4H)-yl)-2-methyl-2-(methylsulfonyl)-N-(((RS)-tetrahydro-2H-pyran-2-yl)oxy)butanamide E.i. Rac-2-methyl-2-(methylsulfonyl)-4-(4-oxo-7-((trimethylsilypethynyl)quinazolin-3(4H)yl)-N-(((RS)-tetrahydro-2H-pyran-2-yl)oxy)butanamide A mixture of the compound of Preparation B (0.514 g; 1.02 mmol), CuI (0.058 g; 0.31 mmol) and PdCl$_2$(PPh$_3$)$_2$ (0.112 g; 0.16 mmol) was flushed with N$_2$ and degassed THF (5.5 mL) was added, followed by TMS-acetylene (0.17 mL, 1.19 mmol) and degassed TEA (0.36 mL; 2.59 mmol). The reaction mixture was stirred at 50° C. for 21 h. The solvent was removed in vacuo. The residue was purified by CC (Hept-EA) to give the title compound as brown gum (0.527 g; 99% yield).

$^1$H NMR (d6-DMSO) δ: (mixture of diastereoisomer) 11.41 (s, 0.5H); 11.39 (s, 0.5H); 8.36 (d, J=7.0 Hz, 1H); 8.12 (d, J=8.2 Hz, 1H); 7.70 (d, J=1.2 Hz, 1H); 7.57 (dd, J=1.2, 8.2 Hz, 1H); 4.89-4.95 (m, 1H); 3.79-4.17 (m, 3H); 3.45-3.55 (m, 1H); 3.08 (s, 1.5H); 3.06 (s, 1.5H); 2.44-2.66 (overlapped m, 1H); 2.13-2.29 (m, 1H); 1.46-1.73 (overlapped m, 6H); 1.61 (s, 1.5H); 1.60 (s, 1.5H); 0.26 (s, 9H).

MS (ESI, m/z): 520.2 [M+H$^+$] for $C_{24}H_{33}N_3O_6SSi$; $t_R$=0.91 min.

E.ii. Rac-4-(7-ethynyl-4-oxoquinazolin-3(4H)-yl)-2-methyl-2-(methylsulfonyl)-N-((tetrahydro-2H-pyran-2-Aoxy)butanamide:

To a solution of intermediate E.i (0.527 g; 1.01 mmol) in MeOH (5.6 mL) was added K$_2$CO$_3$ (0.210 g; 1.52 mmol). The mixture was stirred at rt for 45 min. The mixture was diluted with DCM (50 mL) and water (50 mL). The phases were separated and the aq. layer was extracted twice with a DCM-MeOH mixture (9-1; 2×50 mL). The combined org. layers were washed with brine (60 mL), dried over MgSO$_4$ and evaporated under reduced pressure. The title compound was obtained as a brown foam (0.382 g; 84% yield).

$^1$H NMR (d6-DMSO) δ (mixture of diastereoisomers): 11.40 (br. s, 1H); 8.37 (d, J=6.7 Hz, 1H); 8.14 (d, J=8.2 Hz, 1H); 7.74-7.77 (m, 1H); 7.60 (dd, J=1.2, 8.2 Hz, 1H); 4.88-4.96 (m, 1H); 4.53 (s, 1H); 3.80-4.20 (m, 3H); 3.44-3.57 (m, 1H); 3.08 (s, 1.5H); 3.06 (s, 1.5H); 2.41-2.65 (overlapped m, 1H); 2.15-2.29 (m, 1H); 1.47-1.74 (overlapped m, 6H); 1.61 (s, 1.5H); 1.60 (s, 1.5H).

MS (ESI, m/z): 448.1 [M+H$^+$] for $C_{21}H_{25}N_3O_6S$; $t_R$=0.74 min.

Preparation F 3-(4-iodophenyl)oxetan-3-ol

A solution of 1,4-diiodobenzene (10.690 g; 32.4 mmol) in THF (100 mL) was treated at −78° C. with BuLi (1.35M in Hex; 20 mL). After stirring at this temperature for 30 min, the solution was treated with a suspension of 3-oxetanone (2.14 g; 29.7 mmol) in THF (20 mL). The reaction mixture was allowed to reach rt and was further stirred 1 h at rt. The reaction mixture was treated with 10% aq. NaHSO$_4$ (100 mL) and diluted with water and EA. The aq. layer was extracted with EA. The combined org. layers were washed with brine, dried over MgSO$_4$, filtered and concentrated under reduced pressure. The residue was purified by CC (Hept-EA) to afford the title alcohol as a white solid (5.3 g; 71% yield).

$^1$H NMR (d6-CDCl$_3$) δ: 7.75 (d, J=8.5 Hz, 2H); 7.36 (d, J=8.5 Hz, 2H); 4.82-4.91 (m, 4H); 2.54 (br. s, 1H).

Preparation G tert-butyl (R)-4-amino-2-methyl-2-(methylsulfonyl)butanoate

G.i. Tert-butyl (R)-4-azido-2-methyl-2-(methylsulfonyl)butanoate

Racemic intermediate A.iii (25.5 g) was separated by semi-preparative chiral HPLC Method C (Hept-EtOH-DEA 90-9.99-0.01; flow rate: 24 mL/min, UV detection at 217 nm), the respective retention times (flow rate: 0.8 mL/min) were 10.6 and 11.2 min. The title enantiomer was identified as the first eluting enantiomer and was obtained as a clear oil (11.6 g).

$^1$H NMR (d$_6$-DMSO) δ: 3.56-3.67 (m, 1H); 3.26-3.38 (overlapped m, 1H); 3.10 (s, 3H); 2.38-2.53 (overlapped m, 1H); 1.95-2.06 (m, 1H); 1.45 (s, 9H); 1.43 (s, 3H).

G.ii. Tert-butyl (R)-4-amino-2-methyl-2-(methylsulfonyl)butanoate

A solution of intermediate G.i (11.6 g, 42.7 mmol) in a tBuOH-EA mixture (1-1; 236 mL) was treated with 10%

Pd/C (0.6 g). The suspension was stirred at rt under hydrogen atmosphere for 3.5 h. The catalyst was filtered off, the filtrate was evaporated in vacuo to afford the title compound as a light green oil (10.68 g; 99% yield).

$^1$H NMR (d$_6$-DMSO) δ: 3.06 (s, 3H); 2.63-2.75 (m, 1H); 2.40-2.53 (overlapped m, 1H); 2.16-2.28 (m, 1H); 1.74-1.85 (m, 1H); 1.44 (s, 9H); 1.40 (s, 3H).

MS (ESI, m/z): 252.1 [M+H$^+$] for C$_{10}$H$_{21}$NO$_4$S; t$_R$=0.45 min.

Preparation H (R)-4-(7-ethynyl-4-oxoquinazolin-3(4H)-yl)-2-methyl-2-(methylsulfonyl)-N-((tetrahydro-21-1-pyran-2-yl)oxy)butanamide:

Starting from 2-amino-4-bromobenzoate (5.0 g; 21.4 mmol) and proceeding successively in analogy to Preparation B, steps B.i to B.iv and Preparation E, steps E.i to E.ii, the title compound was obtained as a brown oil (1.13 g, 93% yield).

$^1$H NMR (d$_6$-DMSO) δ (mixture of diastereoisomers): 11.43 (s, 0.5H); 11.42 (s, 0.5H); 8.38 (s, 0.5H); 8.36 (s, 0.5H); 8.14 (d, J=8.2 Hz, 1H); 7.76 (d, J=1.4 Hz, 1H); 7.58-7.61 (m, 1H); 4.92-4.94 (m, 0.5H); 4.89-4.91 (m, 0.5H); 4.55 (s, 1H); 3.99-4.17 (m, 2H); 3.83-3.95 (m, 1H); 3.47-3.54 (m, 1H); 3.08 (s, 1.5H); 3.06 (s, 1.5H); 2.47-2.65 (overlapped m, 1H); 2.17-2.25 (m, 1H); 1.59-1.70 (overlapped m, 3H); 1.62 (s, 1.5H); 1.60 (s, 1.5H); 1.49-1.58 (m, 3H).

MS (ESI, m/z): 447.9 [M+H$^+$] for C$_{21}$H$_{25}$N$_3$O$_6$S; t$_R$=0.74 min.

Preparation I ((1S,2S)-2-(bromoethynyl)cyclopropyl)methyl acetate AND ((1R,2R)-2-(bromoethynyl)cyclopropyl)methyl acetate I.i.
((1S*,2S*)-2-(2,2-dibromovinyl)cyclopropyl)methyl acetate To a solution of CBr$_4$ (36.56 g; 108 mmol) in DCM (76 mL) cooled at −20° C., was added dropwise over 1 h a solution of PPh$_3$ (55.39 g, 211 mmol) in DCM (127 mL). The mixture was stirred at this temperature for 45 min and then cooled to −78° C. A solution of ((1S*,2S*)-2-formylcyclopropyl)methyl acetate (7.54 g, 53 mmol, prepared as described in WO 2012/154204) in DCM (100 mL) was added dropwise over 1.5 h, keeping IT below −70° C. The mixture was stirred at this temperature for 30 min and allowed to warmto rt over 30 min. The solvent was removed in vacuo and the residue was purified by CC (EA-Hept) to afford the title acetate as a colourless oil (7.98 g; 50% yield).

$^1$H NMR (CDCl$_3$) δ: 5.84 (d, J=9.0 Hz, 1H); 3.97 (m, 2H); 2.07 (s, 3H); 1.61 (m, 1H); 1.33 (m, 1H); 0.78-0.92 (m, 2H).

MS (ESI, m/z): 295.0 [M+H$^+$] for C$_8$H$_{10}$O$_2$Br$_2$; t$_R$=0.87 min.

I.ii. ((1S,2S)-2-(bromoethynyl)cyclopropyl)methyl acetate AND ((1R,2R)-2-(bromoethynyl)cyclopropyl)methyl acetate To a solution of intermediate I.i (7.98 g; 26.8 mmol) in THF (160 mL) was added TBAF trihydrate (48 g; 151 mmol). The reaction mixture was heated at 60° C. for 3 h.

The reaction mixture was cooled to rt and diluted with Et$_2$O (150 mL). The org. phase was washed with water (60 mL) and brine (60 mL), dried over MgSO$_4$ and concentrated to dryness. The residue was purified by CC (EA-Hept) and by prep-HPLC (Method 1) to afford the title compound as a colourless oil (2.94 g; 51% yield). The racemic product was separated by semi-preparative chiral HPLC Method B (Hept-EtOH 9-1; flow rate: 16 mL/min, UV detection at 220 nm), the respective retention times (flow rate: 0.8 mL/min) were 5.9 and 8.7 min. The title enantiomers were obtained as colourless oils (1.4 g each).

First-eluting enantiomer, (1S,2S)-configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=+96° (c=1.03; MeOH).

Second-eluting enantiomer, (1R,2R)-configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=−94° (c=1.01; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation J 3-(iodoethynyl)oxetan-3-ol

To a solution of 3-ethynyloxetan-3-ol (1.097 g; 11.2 mmol; commercial) in MeOH (50 mL) and 1M aq. KOH (28 mL) was added iodine (3.549 g; 14 mmol). The reaction mixture was stirred for 2 h at rt. Water (150 mL) and DCM (500 mL) were added. The aq. layer was extracted with EA (500 mL). The org. layer were washed with brine, dried over MgSO$_4$, filtered and concentrated down to afford the desired compound as a light yellow solid (2.21 g; 88% yield).

$^1$H NMR (d$_6$-DMSO) δ: 4.60 (d, J=6.5 Hz, 2H); 4.45 (d, J=6.5 Hz, 2H).

Preparation K (1-(bromoethynyl)cyclopropyl)methoxy)(tert-butyl)diphenylsilane

To a mixture of (dibromomethyl)triphenylphosphonium bromide (8.527 g, 16.6 mmol) and THF (40 mL) was added a solution of tBuOK (1M in THF) (16.6 mL, 16.6 mmol). The resulting dark brown solution was stirred for 3 min at rt, then cooled to 0° C. A solution of 1-(((tert-butyldiphenylsilyl)oxy)methyl)cyclopropanecarbaldehyde (2.2 g; 6.62 mmol; prepared as described in WO 2010/135536) in THF (23 mL) was added dropwise. The reaction was stirred at 0° C. for 40 min. The reaction mixture was cooled to −78° C. and tBuOK (1M in THF, 29.1 mL, 29.1 mmol) was added rapidly and stirred at −78° C. for 30 min. The reaction mixture was quenched with brine (150 mL). The aq. layer was separated and extracted with Et$_2$O (3×150 mL). The combined org. phases were washed with brine, dried over MgSO$_4$, filtered, and concentrated to dryness. The residue was purified by CC (Hept-EA) to afford the title compound as a colourless oil (2.052 g; 75% yield).

¹H NMR (d₆-DMSO) δ: 7.60-7.66 (m, 4H); 7.42-7.48 (m, 6H); 3.57 (s, 2H); 1.02 (s, 9H); 0.84-0.88 (m, 2H); 0.72-0.76 (m, 2H).

Preparation L tert-butyl (4-iodo-2-methylbut-3-yn-2-yl)carbamate:

A solution of tert-butyl (2-methylbut-3-yn-2-yl)carbamate (1.027 g, 5.6 mmol) in THF (10 mL) was cooled to −78° C. under nitrogen and n-BuLi (1.6M in hexanes; 7 mL, 11.2 mmol) was added dropwise. The reaction mixture was stirred at −78° C. for 1 h. A solution of iodine (1.422 g, 5.6 mmol) in THF (5 mL) was added dropwise to the solution at −78° C. (brown solution) and the reaction mixture was stirred at −78° C. for 2 h. The reaction was then quenched by adding sat. Na₂S₂O₃ and allowed to warm up to rt. The mixture was extracted with Et₂O (3×15 mL). The combined org. layers were dried over MgSO₄, filtered and concentrated in vacuo to give the title compound as a light yellow solid (1.50 g; 86% yield).
¹H NMR (CDCl₃) δ: 4.64 (br. s, 1H); 1.56 (m, 6H); 1.45 (s, 9H).

Preparation M (R)-4-(7-ethynyl-6-fluoro-4-oxoquinazolin-3(4H)-yl)-2-methyl-2-(methylsulfonyl)-N-((tetrahydro-2H-pyran-2-yl)oxy)butanamide Starting from intermediate D.i (3.05 g; 12.3 mmol) and the compound of Preparation K (3.434 g; 13.7 mmol) and proceeding successively in analogy to Preparation D, steps D.ii to D.iv (yields: cyclization 77%; ester hydrolysis quant.; amide coupling with THPO-NH₂ 78%) and Preparation E, steps E.i and E.ii (yields: Sonogashira coupling 86%; TMS cleavage 95%), the title compound was obtained as an orange solid (2.9 g).
¹H NMR (d₆-DMSO) δ (mixture of diastereoisomers): 11.44 (br. s, 1H); 8.40 (s, 0.5H); 8.38 (s, 0.5H); 7.88-7.92 (m, 2H); 4.83-4.93 (overlapped m, 1H); 4.85 (s, 1H); 4.10-4.27 (m, 1H); 3.86-4.07 (m, 2H); 3.43-3.51 (m, 1H); 3.09 (s, 1.5H); 3.06 (s, 1.5H); 2.35-2.58 (overlapped m, 1H); 2.11-2.25 (m, 1H); 1.36-1.90 (m, 9H).
MS (ESI, m/z): 466.0 [M+H⁺] for $C_{21}H_{24}N_3O_6FS$; $t_R$=0.76 min.

Preparation N ((3-(bromoethynyl)bicyclo[1.1.1]pentan-1-yl)methoxy)(tert-butyl)diphenylsilane N.i. Bicyclo[1.1.1]pentane-1,3-diyldimethanol To a solution of dimethyl bicyclo[1.1.1]pentane-1,3-dicarboxylate (1.74 g; 9.45 mmol; commercial) in THF (12 mL), cooled at 0° C. was added dropwise LiAlH₄ (2.4M in THF; 5.29 mL; 12.7 mmol) over 45 min, keeping IT below 15° C. The suspension was stirred at rt for 3 h. The crude mixture was cooled to 0° C. and carefully quenched by water (0.48 mL), 15% aq. NaOH (0.48 mL) and water (1.44 mL). The mixture was stirred at rt for 35 min then THF (17 mL) and MgSO₄ (4 g) were added. The mixture was stirred at rt for 10 min. The resulting suspension was filtered, the solids were washed with THF (20 mL) and the filtrate was evaporated to dryness. The residue was purified by CC (Hept-EA) to afford the title compound as a colourless oil (1.2 g; 99% yield).
¹H NMR (d₆-DMSO) δ: 4.40 (t, J=5.5 Hz, 2H); 3.35 (d, J=5.6 Hz, 4H); 1.46 (s, 6H).

N.ii. (3-(((tert-butyldiphenylsilyl)oxy)methyl)bicyclo[1.1.1]pentan-1-yl)methanol To a suspension of NaH (60% in oil; 0.41 g; 10.2 mmol) in THF (8 mL) was added slowly, at rt, a solution of intermediate N.i (1.19 g; 9.31 mmol) in THF (5.7 mL). IT was kept under 27° C. After 1 h stirring, a solution of TBDPS-Cl (2.5 mL, 9.38 mmol) in THF (4.8 mL) was added dropwise over 16 min. The reaction mixture was stirred 3 h, then diluted in Et₂O (30 mL). The org. phase was washed twice with brine (20 mL), dried over Na₂SO₄ and concentrated in vacuo. The residue was purified by CC (Hept-EA) to afford the title compound as a colourless oil (0.61 g; 26% yield).
¹H NMR (d₆-DMSO) δ: 7.56-7.64 (m, 4H); 7.39-7.50 (m, 6H); 4.43 (t, J=5.6 Hz, 1H); 3.64 (s, 2H); 3.36 (d, J=5.5 Hz, 2H); 1.49 (s, 6H); 1.01 (s, 9H).

N.iii. 3-(((tert-butyldiphenylsilyl)oxy)methyl)bicyclo[1.1.1]pentane-1-carbaldehyde To a solution of intermediate N.ii (1.09 g; 2.98 mmol) in DCM (6.9 mL) cooled to −10° C., was added DIPEA (1.59 mL; 9.31 mmol) over 15 min. A solution of Pyr.SO₃ complex (45%; 1.44 g; 4.07 mmol) in DMSO (4.03 mL) was then added dropwise over 10 min, keeping IT below −5° C. The reaction mixture was stirred for 1.25 h at 0° C. and 1 h at rt. The reaction mixture was partitioned between water (35 mL) and DCM (20 mL). The two layers were separated and the aq. layer was extracted with DCM (15 mL). The combined org. layers were dried over Na₂SO₄ and concentrated to dryness. The residue was co-evaporated with toluene (2×10 mL) and purified by CC (Hept-EA) to afford the title aldehyde as a colourless oil (0.94 g; 87% yield).
¹H NMR (d6-DMSO) δ: 9.53 (s, 1H); 7.57-7.62 (m, 4H); 7.41-7.49 (m, 6H); 3.68 (s, 2H); 1.86 (s, 6H); 1.01 (s, 9H).

N.iv. Tert-butyl((3-(2,2-dibromovinyl)bicyclo[1.1.1]pentan-1-yl)methoxy)diphenylsilane Starting from intermediate N.iii (0.941 g; 2.58 mmol) and proceeding in analogy to Preparation I, step I.i., the title compound was obtained, after purification by CC (Hept-EA), as a yellow oil (1.196 g; 89% yield).
¹H NMR (d₆-DMSO) δ: 7.57-7.61 (m, 4H); 7.41-7.49 (m, 6H); 6.74 (s, 1H); 3.64 (s, 2H); 1.90 (s, 6H); 1.01 (s, 9H).

N.v. ((3-(bromoethynyl)bicyclo[1.1.1]pentan-1-yl)methoxy)(tert-butyl)diphenylsilane A solution of intermediate N.iv (0.45 g; 0.86 mmol) in dry THF (2 mL) cooled at −78° C. was treated with a solution of tBuOK (1M, 3.8 mL). IT was kept under −69° C. The reaction mixture was stirred at −78° C. for 30 min, was diluted with brine (8 mL) and was allowed to reach rt. Et₂O (15 mL) was added. The aq. layer was separated and extracted once again with Et₂O (15 mL). The combined org. layers were washed with brine (10 mL), dried over Na₂SO₄, filtered and concentrated to afford the title compound as a yellowish oil (0.37 g; 97% yield).

$^1$H NMR (d$_6$-DMSO) δ: 7.55-7.60 (m, 4H); 7.41-7.49 (m, 6H); 3.60 (s, 2H); 1.91 (s, 6H); 1.00 (s, 9H).

Preparation O (3aR,5S,6aS)-5-(bromoethynyl)-2,2-dimethyltetrahydro-4H-cyclopenta[d][1,3]dioxole Starting from (3aR,5S,6aS)-5-(2,2-dibromovinyl)-2,2-dimethyltetrahydro-4H-cyclopenta[d][1,3]dioxole (2.06 g; 6.32 mmol; prepared as described in WO 2013/170030) and proceeding in analogy to Preparation N, step N.v, the title compound was obtained as a yellow oil (1.37 g; 88% yield).

$^1$H NMR (CDCl$_3$) δ: 4.60-4.63 (m, 2H); 2.85-2.93 (m, 1H); 2.12-2.17 (m, 2H); 1.51-1.60 (overlapped m, 2H); 1.41 (s, 3H); 1.26 (s, 3H).

Preparation P (1-(4-iodophenyl)cyclopropyl)methanol

A sealed tube was charged with NaI (0.83 g; 5.49 mmol), CuI (0.1 g; 0.55 mmol) and 1-(4-bromophenyl)cyclopropyl)methanol (0.62 g; 2.74 mmol). 1,4-dioxane (3 mL) and trans-N,N-dimethylcyclohexa-1,2-diamine (0.17 mL; 1.1 mmol) were added. The reaction mixure was heated at 180° C. for 40 min under microwave irradiation. The mixture was filtered over Celite. Solids were washed with EA and the filtrate was concentrated to dryness. The residue was purified by CC (Hept-EA) to obtain the title product as a yellow oil which cristallized on standing (0.654 g; 87% yield).

$^1$H NMR (CDCl$_3$) δ: 7.61 (d, J=8.5 Hz, 1H); 7.11 (d, J=8.5 Hz, 1H); 4.70 (t, J=5.7 Hz, 1H); 3.50 (d, J=5.7 Hz, 1H); 0.70-0.73 (m, 1H); 0.81-0.84 (m, 1H).

Preparation Q (R)-5-iodopent-4-yne-1,2-diol

To a mixture of (R)-pent-3-yne-1,2-diol (0.299 g; 2.99 mmol; prepared as described in WO 2013/170030) and 1M KOH (7.5 mL) in MeOH (13 mL) was added, in one portion, I$_2$ (0.992 g; 3.91 mmol). The reaction mixture was stirred at rt for 1.75 h. Water (15 mL) and DCM (60 mL) were added. The phases were separated. The aq. layer was extracted with EA (3×20 mL). The combined org. layers were dried over MgSO$_4$ and concentrated to dryness to afford the title compound as a yellow oil (0.7 g; quant.).

$^1$H NMR (CDCl$_3$) δ: 3.85-3.91 (m, 1H); 3.71-3.77 (m, 1H); 3.56-3.62 (m, 1H); 2.62 (dd, J=3.2, 6.4 Hz, 2H); 2.36 (br. s, 1H); 1.92 (br. s, 1H).

Preparation R ((1R,2R)-2-(bromoethynyl)-1-methylcyclopropyl)methyl acetate

Starting from ((1R,2R)-2-formyl-1-methylcyclopropyl)methyl acetate (0.250 g; 1.6 mmol; prepared as described in WO 2012/154204) and proceeding in analogy to Preparation I, steps I.i (100% yield) and I.ii (43% yield), the title compound was obtained, after purification by CC (PE-EA), as a colourless oil (0.160 g).

$^1$H NMR (CDCl$_3$) δ: 3.89 (d, J=11.4 Hz, 1H); 3.80 (d, J=11.4 Hz, 1H); 2.07 (s, 3H); 1.39 (dd, J=5.5, 8.9 Hz, 1H); 1.27 (s, 3H); 0.94 (dd, J=4.8, 8.9 Hz, 1H); 0.64-0.67 (m, 1H).

Preparation S (dibromomethyl)triphenylphosphonium bromide

To a solution of PPh$_3$ (31.6 g; 121 mmol) in dry DCM (120 mL) was added dropwise over 45 min a solution of CBr$_4$ (20 g; 60.3 mmol) in DCM (25 mL) at rt. After 40 min, water (10 mL) was added slowly. The phases were separated and the org. phase was dried over MgSO$_4$ and concentrated to dryness. The residue was dissolved in boiling dry MeOH (25 mL) and the mixture was cooled to 20° C. After addition of EA (45 mL) and cooling to −30° C., the precipitate was filtered and dried over vacuum to afford the title compound as a yellow solid (24.33 g; 78% yield).

$^1$H NMR (CDCl$_3$) δ: 10.35 (d, J=2.4 Hz, 1H); 8.13-8.23 (m, 6H); 7.81-7-87 (m, 3H); 7.71-7.77 (m, 6H).

MS (ESI, m/z): 434.7 [M+H$^+$] for C$_{19}$H$_{is}$Br$_2$P; t$_R$=0.71 min.

Preparation T (RS)-4-(1-(bromoethynyl)cyclopropyl)-2,2-dimethyl-1,3-dioxolane

T.i. (RS)-1-(1-((benzyloxy)methyl)cyclopropyl)ethane-1,2-diol

To a solution of (((1-vinylcyclopropyl)methoxy)methyl)benzene (5.39 g, 17.5 mmol, prepared as described in Wender et al., *Org. Lett.* (2010), 12, 1604-1607) in DCM (65 mL) and water (17 mL) were added NMO (2.45 g, 21 mmol) and potassium osmate (0.191 g; 0.52 mmol). The mixture was stirred vigorously at rt overnight. Aq. 40% sodium bisulfite (30 mL) and DCM (30 mL) were added. The aq. layer was extracted with DCM (40 mL). The combined org. layers were washed with brine, dried over MgSO$_4$ and concentrated down. The crude product was purified by CC (Hept-EA) to afford the desired product as a white solid (5.40 g; quant.).

$^1$H NMR (d$_6$-DMSO) δ: 7.24-7.40 (m, 5H); 4.48 (d, J=4.6 Hz, 1H); 4.43 (s, 2H); 4.31 (t, J=5.5 Hz, 1H); 3.66 (d, J=9.9 Hz, 1H); 3.47-3.54 (m, 1H); 3.34-3.41 (overlapped m, 1H); 3.18-3.25 (m, 1H); 3.07 (d, J=10.1 Hz, 1H); 0.51-0.58 (m, 1H); 0.41-0.47 (m, 1H); 0.35-0.40 (m, 1H); 0.26-0.33 (m, 1H).

MS (ESI, m/z): 223.1 [M+H$^+$] for C$_{13}$H$_{18}$O$_3$; t$_R$=0.63 min.

T.ii. (RS)-4-(1-((benzyloxy)methyl)cyclopropyl)-2,2-dimethyl-1,3-dioxolane

To a solution of intermediate T.i (5.40 g; 24.3 mmol) in THF (122 mL) were added TsOH (0.231 g; 1.21 mmol) and 2,2-dimethoxypropane (9.14 mL; 72.9 mmol). The reaction mixture was stirred at rt overnight. Sat. aq. NaHCO$_3$ (20 mL) and EA (35 mL) were added.

The aq. layer was extracted once with EA (25 mL). The org. layer was washed with brine (20 mL), dried over MgSO$_4$ and evaporated under reduced pressure to afford the desired product as a colourless oil (6.78 g; quant.).

$^1$H NMR (d$_6$-DMSO) δ: 7.25-7.40 (m, 5H); 4.40-4.49 (m, 2H); 3.92-4.08 (m, 2H); 3.68 (t, J=7.6 Hz, 1H); 3.33 (d, J=10.2 Hz, 1H); 3.40 (d, J=10.1 Hz, 1H); 1.27 (s, 3H); 1.25 (s, 3H); 0.55 (m, 2H); 0.41 (m, 2H).

T.iii. (RS)-(1-(2,2-dimethyl-1,3-dioxolan-4-yl)cyclopropyl)methanol:

To a solution of intermediate T.ii (6.78 g; 30.5 mmol) in MeOH (200 mL) was added 10% Pd/C (3 g). The mixture was stirred at rt under hydrogen atmosphere. The catalyst was filtered off and rinsed with EA. The solvents were evaporated under reduced pressure. The crude product was purified by CC (Hept-EA) to afford the desired product as a colourless oil (2.16 g; 41% yield).

$^1$H NMR (d$_6$-DMSO) δ: 4.51 (t, J=5.6 Hz, 1H); 4.07 (dd, J=6.1, 7.5 Hz, 1H); 3.97 (dd, J=6.1, 8.1 Hz, 1H); 3.63 (t, J=7.8 Hz, 1H); 3.26-3.38 (m, 2H); 1.27 (s, 3H); 1.25 (s, 3H); 0.31-0.54 (m, 4H).

T.iv. (RS)-1-(2,2-dimethyl-1,3-dioxolan-4-yl)cyclopropane-1-carbaldehyde

Starting from intermediate T.iii (3.58 g; 20.8 mmol) and proceeding in analogy to Preparation N, step N.iii, the title compound was obtained, after purification by CC (Hept-EA), as a colourless oil (3.26 g; 92% yield).

$^1$H NMR (d$_6$-DMSO) δ: 8.83 (m, 1H); 4.45 (t, J=6.6 Hz, 1H); 4.16 (dd, J=6.4, 8.2 Hz, 1H); 3.54 (dd, J=6.9, 8.2 Hz, 1H); 1.30 (s, 3H); 1.26 (s, 3H); 1.07-1.24 (m, 4H).

T.v. (RS)-4-(1-(bromoethynyl)cyclopropyl)-2,2-dimethyl-1,3-dioxolane

To a solution of the compound from Preparation S (5.29 g; 10.3 mmol) in THF (25 mL) was rapidly added tBuOK (1M in THF; 13.2 mL; 13.2 mmol). The resulting dark brown solution was stirred for 3 min at rt and then cooled to 0° C. A solution of intermediate T.iv (0.5 g; 2.94 mmol) in THF (9 mL) was added dropwise. The reaction was stirred at 0° C. for 40 min. and cooled to -78° C. tBuOK (1M in THF; 12.9 mL; 12.9 mmol) was rapidly added. The reaction proceeded at -78° C. for 30 min. Brine (75 mL) was added and the mixture was allowed to reach rt. The aq. layer was separated and extracted with Et$_2$O (3×100 mL). The combined org. layers were washed with brine (100 mL), dried over MgSO$_4$ and concentrated to dryness. The residue was purified by CC (Hept-EA) to afford the title compound as a yellow oil (0.543 g; 75% yield).

$^1$H NMR (d$_6$-DMSO) δ: 4.06 (dd, J=6.4, 8.2 Hz, 1H); 3.77 (dd, J=7.0, 8.2 Hz, 1H); 3.56 (t, J=6.7 Hz, 1H); 1.35 (s, 3H); 1.26 (s, 3H); 0.74-0.96 (m, 4H).

Preparation U (((1R,2R)-2-(bromoethynyl)-2-methylcyclopropyl)methoxy)(tert-butyl)diphenylsilane U.i. ((1R, 2R)-2-(hydroxymethyl)-1-methylcyclopropyl)methyl acetate To a solution of ((1R,2R)-2-formyl-1-methylcyclopropyl)methyl acetate (0.925 g; 5.92 mmol, prepared as described in WO 2012/154204) in MeOH (10 mL) was added NaBH$_4$ (0.297 g; 7.7 mmol) portionwise at 0° C. The reaction was stirred for 80 min at 0° C., then for 30 min at rt. Water (10 mL) and DCM (40 mL) were added and the phases were separated. The aq. layer was extracted with DCM-MeOH 9-1 (2×15 mL) and the combined org. layers were dried over Na$_2$SO$_4$ and filtered. The filtrate was evaporated under reduced pressure to give the title compound as a colourless oil (0.968 g; quant.).

$^1$H NMR (CDCl$_3$) δ: 3.89 (d, J=11.3 Hz, 1H); 3.82 (d, J=11.3 Hz, 1H); 3.74-3.80 (m, 1H); 3.49-3.56 (m, 1H); 2.08 (s, 3H); 1.19 (s, 3H); 1.09-1.15 (m, 1H); 0.70-0.76 (m, 1H); 0.27-0.31 (m, 1H).

U.ii. ((1R, 2R)-2-(((tert-butyldiphenylsilyl)oxy)methyl)-1-methylcyclopropyl)methyl acetate To a solution of intermediate U.i (0.94 g; 5.92 mmol) in DCM (12 mL) was added imidazole (0.819 g; 11.9 mmol). The solution was cooled to 0° C. and TBDPS-Cl (1.6 mL; 6.03 mmol) was added dropwise. The reaction mixture was stirred at 0° C. for 20 min then at rt for 2.5 h. Aq. NaHSO$_4$ (15%; 20 mL) was added. The aq. phase was extracted with DCM (10 mL). The combined org. layers were dried over MgSO$_4$, filtered and the filtrate concentrated to dryness. The residue was purified by CC (Hept-EA) to afford the title compound as a colourless oil (2.29 g; 97% yield).

$^1$H NMR (CDCl$_3$) δ: 7.66-7.70 (m, 4H); 7.35-7.45 (m, 6H); 3.84 (s, 2H); 3.82-3.88 (overlapped m, 1H); 3.46-3.55 (m, 1H); 2.07 (s, 3H); 1.14 (s, 3H); 1.05 (s, 9H); 1.03-1.11 (overlapped m, 1H); 0.59-0.65 (m, 1H); 0.14-0.19 (m, 1H).

MS (ESI, m/z): 397.01 [M+H$^+$] for C$_{24}$H$_{32}$O$_3$Si; t$_R$=1.13 min.

U.iii. ((1R, 2R)-2-(((tert-butyldiphenylsilyl)oxy)methyl)-1-methylcyclopropyl)methanol To a solution of intermediate U.ii (2.29 g; 5.77 mmol) in MeOH (50 mL) was added K$_2$CO$_3$ (1.59 g; 11.5 mmol). The suspension was stirred at rt for 4 h. The reaction mixture was filtered and the solid was washed with DCM. The filtrate was evaporated under reduced pressure. The residue was partitioned between water (30 mL) and DCM (40 mL).

The aq. layer was extracted with DCM-MeOH 9-1 (40 mL) and EA-MeOH 9-1 (40 mL). The combined org. layers were dried over MgSO$_4$, filtered and evaporated under reduced pressure. The residue was purified by CC (Hept-EA) to afford the title compound as a colourless oil (1.59 g; 78% yield).

$^1$H NMR (CDCl$_3$) δ: 7.66-7.72 (m, 4H); 7.36-7.45 (m, 6H); 3.86 (dd, J=5.8, 11.1 Hz, 1H); 3.49 (dd, J=8.7, 11.1 Hz, 1H); 3.38 (d, J=11.0 Hz, 1H); 3.30 (d, J=11.0 Hz, 1H); 1.16 (s, 3H); 1.05 (s, 9H); 0.95-1.02 (m, 1H); 0.55 (dd, J=4.8, 9.0 Hz, 1H); 0.12-0.16 (m, 1H).

U.iv. (((1R,2R)-2-(bromoethynyl)-2-methylcyclopropyl)methoxy)(tert-butyl)diphenylsilane Starting from intermediate U.iii (1.59 g; 4.5 mmol) and proceeding successively in analogy to Preparation N, step N.iii (92% yield), Preparation I, step I.i (85% yield) and Preparation N, step N.v (98% yield), the title compound was obtained as a yellow oil (1.48 g).

$^1$H NMR (CDCl$_3$) δ: 7.65-7.72 (m, 4H); 7.36-7.46 (m, 6H); 3.79 (dd, J=5.6, 11.5 Hz, 1H); 3.49 (dd, J=8.4, 11.5 Hz, 1H); 1.43-1.51 (m, 1H); 1.25 (s, 3H); 1.05 (s, 9H); 1.02 (dd, J=4.7, 9.1 Hz, 1H); 0.37 (dd, J=4.7, 6.4 Hz, 1H).

Preparation V (R)-4-(7-ethynyl-8-fluoro-4-oxoquinazolin-3(4H)-yl)-2-methyl-2-(methylsulfonyl)-N-((tetrahydro-2H-pyran-2-yl)oxy)butanamide V.i. Methyl 2-amino-4-bromo-3-fluorobenzoate Starting from 2-amino-4-bromo-3-fluorobenzoic acid (1.742 g, 7.44 mmol; prepared according to WO 2012/170845) and TMS-diazomethane (2M in hexanes; 8.5 mL; 17 mmol) and proceeding in analogy to Preparation D, step D.i, the title compound was obtained, after purification by CC (Hept-EA), as a yellow solid (1.17 g, 63% yield).

$^1$H NMR (d$_6$-DMSO) δ: 7.48 (dd, J=1.7, 8.8 Hz, 1H); 6.79-6.82 (m, 3H); 3.82 (s, 3H).

MS (ESI, m/z): 290.7 [M+41] for C$_8$H$_7$NO$_2$BrF; t$_R$=0.86 min.

V.ii. Methyl (E)-4-bromo-2-(((dimethylamino)methylene)amino)-3-fluorobenzoate Starting from intermediate V.i (1.17 g; 4.72 mmol) and proceeding in analogy to Preparation B, step B.i, the title compound was obtained as a purple oil (1.38 g; 96% yield).

$^1$H NMR (d$_6$-DMSO) δ: 7.59 (d, J=2.3 Hz, 1H); 7.34 (dd, J=1.4, 8.5 Hz, 1H); 7.24 (dd, J=6.2, 8.5 Hz, 1H); 3.73 (s, 3H); 3.00 (s, 3H); 2.92 (s, 3H).

MS (ESI, m/z): 304.9 [M+H$^+$] for C$_{11}$H$_{12}$N$_2$O$_2$BrF; t$_R$=0.54 min.

V.iii. Tert-butyl (R)-4-(7-bromo-8-fluoro-4-oxoquinazolin-3(4H)-yl)-2-methyl-2-(methylsulfonyl)butanoate Starting from intermediate V.ii (1.38 g, 4.55 mmol) and the compound of Preparation G (1.26 g; 5.03 mmol) and proceeding in analogy to Preparation B, step B.ii, the compound was obtained, after purification by CC (Hept-EA), as a beige solid (1.69 g; 78% yield).

$^1$H NMR (d$_6$-DMSO) δ: 8.52 (s, 1H); 7.90 (dd, J=1.2, 8.7 Hz, 1H); 7.82 (dd, J=6.1, 8.7 Hz, 1H); 3.98-4.14 (m, 2H); 3.14 (s, 3H); 2.47-2.60 (overlapped m, 1H); 2.18-2.29 (m, 1H); 1.57 (s, 3H); 1.43 (s, 9H).

MS (ESI, m/z): 478.9 [M+H$^+$] for C$_{18}$H$_{22}$N$_2$O$_5$BrFS; t$_R$=0.88 min.

V.iv. (R)4-(7-bromo-8-fluoro-4-oxoquinazolin-3(4H)-yl)-2-methyl-2-(methylsulfonyl)butanoic acid hydrochloride Starting from intermediate V.iii (1.69 g; 3.53 mmol) and proceeding in analogy to Preparation B, step B.iii, the title compound was obtained as a white solid (1.59 g; quant.).

$^1$H NMR (d$_6$-DMSO) δ: 8.50 (s, 1H); 7.88 (dd, J=1.1, 8.7 Hz, 1H); 7.81 (dd, J=6.0, 8.7 Hz, 1H); 4.02-4.20 (m, 2H); 3.14 (s, 3H); 2.46-2.65 (overlapped m, 1H); 2.19-2.29 (m, 1H); 1.59 (s, 3H).

MS (ESI, m/z): 422.8 [M+H$^+$] for C$_{14}$H$_{14}$N$_2$O$_5$BrFS; t$_R$=0.67 min.

V.v. (R)-4-(7-bromo-8fluoro-4-oxoquinazolin-3(4H)-yl)-2-methyl-2-(methylsulfonyl)-N-((tetrahydro-2H-pyran-2-yl)oxy)butanamide Starting from intermediate V.iv (1.59 g; 3.47 mmol) and proceeding in analogy to Preparation B, step B.iv, the title product was obtained as a white solid (1.53 g; 85% yield).

$^1$H NMR (d$_6$-DMSO) δ: 11.41 (s, 1H); 8.45 (s, 0.5H); 8.43 (s, 0.5H); 7.89 (dd, J=0.8, 8.7 Hz, 1H); 7.79-7.85 (m, 1H); 4.91-4.93 (m, 0.5H); 4.86-4.89 (m, 0.5H); 3.85-4.19 (m, 3H); 3.45-3.56 (m, 1H); 3.08 (s, 1.5H); 3.06 (s, 1.5H); 2.46-2.67 (overlapped m, 1H); 2.15-2.26 (m, 1H); 1.59-1.70 (overlapped m, 3H); 1.62 (s, 1.5H); 1.61 (s, 1.5H); 1.48-1.57 (m, 3H).

MS (ESI, m/z): 521.9 [M+H$^+$] for C$_{19}$H$_{23}$N$_3$O$_6$BrFS; t$_R$=0.77 min.

V.vi. (R)-4-(8-fluoro-4-oxo-7-((trimethylsilyl)ethynyl)quinazolin-3(4H)-yl)-2-methyl-2-(methylsulfonyl)-N-((tetrahydro-2H-pyran-2-yl)oxy)butanamide Starting from intermediate V.v (1.532 g; 2.94 mmol) and TMS-acetylene (0.47 mL, 3.3 mmol) and proceeding in analogy to Preparation E, step E.i, the title compound was obtained, after purification by CC (Hept-EA), as a beige solid (1.44 g; 91% yield).

$^1$H NMR (d$_6$-DMSO) δ: (mixture of diastereoisomers) 11.42 (s, 0.5H); 11.41 (s, 0.5H); 8.43 (s, 0.5H); 8.41 (s, 0.5H); 7.91 (d, J=8.3 Hz, 1H); 7.57-7.62 (m, 1H); 4.89-4.94 (m, 1H); 3.98-4.17 (m, 2H); 3.85-3.96 (m, 1H); 3.46-3.54 (m, 1H); 3.08 (s, 1.5H); 3.06 (s, 1.5H); 2.45-2.67 (overlapped m, 1H); 2.16-2.26 (m, 1H); 1.59-1.70 (overlapped m, 3H); 1.62 (s, 1.5H); 1.61 (s, 1.5H); 1.49-1.57 (m, 3H); 0.28 (s, 9H).

MS (ESI, m/z): 538.0 [M+H$^+$] for C$_{24}$H$_{32}$N$_3$O$_6$FSSi; t$_R$=0.92 min.

V.vii. (R)-4-(7-ethynyl-8-fluoro-4-oxoquinazolin-3(4H)-yl)-2-methyl-2-(methylsulfonyl)-N-((tetrahydro-2H-pyran-2-yl)oxy)butanamide Starting from intermediate V.vi (1.44 g; 2.68 mmol) and proceeding in analogy to Preparation E, step E.ii, the title compound was obtained, after purification by CC (DCM-MeOH), as a yellow solid (0.761 g; 61% yield).

$^1$H NMR (d$_6$-DMSO) δ (mixture of diastereoisomers): 11.42 (s, 0.5H); 11.41 (s, 0.5H); 8.44 (s, 0.5H); 8.42 (s, 0.5H); 7.93 (d, J=8.3 Hz, 1H); 7.59-7.65 (m, 1H); 4.91-4.93 (m, 0.5H); 4.87-4.90 (m, 0.5H); 4.85 (s, 1H); 3.98-4.17 (m, 2H); 3.87-3.97 (m, 1H); 3.46-3.54 (m, 1H); 3.08 (s, 1.5H); 3.06 (s, 1.5H); 2.44-2.67 (overlapped m, 1H); 2.16-2.26 (m, 1H); 1.59-1.70 (overlapped m, 3H); 1.62 (s, 1.5H); 1.61 (s, 1.5H); 1.48-1.58 (m, 3H).

MS (ESI, m/z): 465.9 [M+H$^+$] for C$_{21}$H$_{24}$N$_3$O$_6$FS; t$_R$=0.75 min.

Preparation W

(1-(4-iodophenyl)cyclopropyl)methyl dimethylglycinate

To a solution of (1-(4-iodophenyl)cyclopropyl)methanol (0.46 g; 1.68 mmol; commercial) in DCM (19 mL) were added N,N-dimethylglycine (0.18 g, 1.69 mmol), EDC.HCl (0.44 g; 2.3 mmol) and DMAP (0.27 g; 2.19 mmol). The reaction was stirred at rt for 31 h. A solution of 5% aq. NaHCO$_3$ (5 mL) was added to the reaction mixture and the two phases were separated. The aq. layer was extracted twice with DCM (3×20 mL). The combined org. layers were dried over MgSO$_4$ and evaporated under vacuum. The crude was purified by CC (DCM-MeOH) to afford the title compound as a colourless oil (0.48 g; 79% yield).

$^1$H NMR (d$_6$-DMSO) δ: 7.61-7.65 (m, 2H); 7.08-7.12 (m, 2H); 4.17 (s, 2H); 3.10 (s, 2H); 2.17 (s, 6H); 0.95-0.98 (m, 2H); 0.86-0.90 (m, 2H).

MS (ESI, m/z): 361.0 [M+H$^+$] for C$_{14}$H$_{18}$NO$_2$I; t$_R$=0.66 min.

Preparation X

((1S,2S)-2-(bromoethynyl)-1-methylcyclopropyl)methyl acetate

Xi. (R,E)-3-(2,2-dimethyl-1,3-dioxolan-4-yl)-2-methylallyl acetate

To a solution of (R,E)-3-(2,2-dimethyl-1,3-dioxolan-4-yl)-2-methylprop-2-en-1-ol (1.4 g; 8.1 mmol; prepared as described in Smith et al., *Tetrahedron* (2009), 65(33), 6470-6488) in THF (48 mL) was added TEA (2.8 mL, 20.1 mmol). Acetyl chloride (1.2 mL; 8.2 mmol) was added dropwise over 10 min at 0° C. The reaction mixture was stirred at 0° C. for 2 h. The reaction was poured into water (80 mL) and the aq. layer was extracted three times with EA (3×50 mL). The combined org. layers were dried over MgSO$_4$ and the solvent was removed under reduce pressure. The crude was purified by CC (PE-EA) to afford the product as a colourless oil (1.64 g; 94% yield).

$^1$H NMR (CDCl$_3$) δ: 5.48-5.51 (m, 1H); 4.79-4.84 (m, 1H); 4.44-4.52 (m, 2H); 4.07-4.11 (m, 1H); 3.55 (t, J=8.0 Hz, 1H); 2.09 (s, 3H); 1.75 (d, J=1.3 Hz, 3H); 1.43 (s, 3H); 1.40 (s, 3H).

Xii. ((1S,2S)-2-((R)-2,2-dimethyl-1,3-dioxolan-4-yl)-1-methylcyclopropyl)methyl acetate To a solution of intermediate X.i (1.64 g; 7.65 mmol) in toluene (102 mL), in a reactor equipped with a mechanical stirrer, cooled at −25° C., was added dropwise ZnEt$_2$ (15% in toluene; 34.5 mL, 38.3 mmol) over 20 min, keeping IT below −20° C. Upon the addition, diiodomethane (6.5 mL; 76.9 mmol) was added dropwise over 10 min, keeping IT below −20° C. with a vigorous stirring. The reaction mixture was stirred at −20° C. for 2 h. Then, the reaction mixture was allowed to slowly warm up to rt and stirred overnight at this temperature. The reaction mixture was quenched by addition of sat. aq. NH$_4$Cl (33 mL) and extracted four times with Et$_2$O (4×30 mL). The combined org. layers were washed with sat. aq. Na$_2$S$_2$O$_3$ (30 mL), water (30 mL) and brine (30 mL), then dried over MgSO$_4$, filtered and evaporated under reduced pressure. The crude was purified by CC (PE-EA) to afford a yellow oil (1.4 g; 80% yield).

$^1$H NMR (CDCl$_3$) δ: 4.09 (dd, J=5.9, 7.9 Hz, 1H); 3.89 (d, J=11.3 Hz, 1H); 3.74 (d, J=5.9, 7.9 Hz, 1H); 3.70-3.76 (overlapped m, 1H); 3.61-3.66 (m, 1H); 2.07 (s, 3H); 1.45 (s, 3H); 1.36 (s, 3H); 1.13 (s, 3H); 0.85-0.95 (m, 2H); 0.56 (t, J=5.0 Hz, 1H).

Xiii. ((1S,2S)-2-((R)-1,2-dihydroxyethyl)-1-methylcyclopropyl)methyl acetate A mixture of intermediate X.ii (1.4 g; 6.1 mmol) in AcOH 80% (14 mL) was stirred at rt for 23 h. The mixture was added to NaHCO$_3$ (100 mL; pH 6-7) and the aq. layer was extracted three times with DCM (3×60 mL). The combined org. layers were washed with water (10 mL) and brine (20 mL), dried over MgSO$_4$ and evaporated under reduced pressure. The residue was co-evaporated with cyclohexane. The crude was purified by CC (DCM-MeOH) to afford a colourless oil (1 g; 87% yield).

$^1$H NMR (CDCl$_3$) δ: 3.89 (d, J=11.3 Hz, 1H); 3.74 (d, J=11.3 Hz, 1H); 3.68 (dd, J=3.4, 11.2 Hz, 1H); 3.57 (dd, J=7.4, 11.2 Hz, 1H); 3.33-3.39 (m, 1H); 2.07 (s, 3H); 1.16 (s, 3H); 0.89 (td, J=5.7, 9.0 Hz, 1H); 0.80 (dd, J=4.9, 8.8 Hz, 1H); 0.48 (t, J=5.3 Hz, 1H).

X.iv. ((1S,2S)-2-formyl-1-methylcyclopropyl)methyl acetate

Intermediate X.iii (1 g; 5.3 mmol) was dissolved in a mixture of THF (16.5 mL), water (3.4 mL) and sat. aq. NaHCO$_3$ (1.6 mL). The solution was cooled in a ice-cooled bath and NaIO$_4$ (1.48 g; 6.9 mmol) was added. The reaction mixture was stirred at 0° C. for 30 min.

The reaction mixture was filtered. The solid was washed with Et$_2$O and the phases were separated. The aq. layer was extracted three times with Et$_2$O (3×40 mL). The combined org. layers were dried over MgSO$_4$ and the solvent was removed under reduce pressure to give the product as a colourless oil (0.81 g; 98% yield).

$^1$H NMR (CDCl$_3$) δ: 9.47 (d, J=4.7 Hz, 1H); 4.00 (d, J=11.4 Hz, 1H); 3.85 (d, J=11.4 Hz, 1H); 2.09 (s, 3H); 1.92-1.97 (m, 1H); 1.39 (t, J=5.3 Hz, 1H); 1.32 (s, 3H); 1.21 (dd, J=5.0, 8.3 Hz, 1H).

X.v. ((1S,2R)-2-(2,2-dibromovinyl)-1-methylcyclopropyl)methyl acetate:

Starting from intermediate X.iv (0.81 g; 5.2 mmol) and proceeding in analogy to Preparation I, step I.i, the title compound was obtained, after purification by CC (PE-TBME), as a colourless oil (1.31 g; 81% yield).

$^1$H NMR (CDCl$_3$) δ: 6.09 (d, J=8.6 Hz, 1H); 3.90 (s, 2H); 2.08 (s, 3H); 1.63 (td, J=5.6, 8.7 Hz, 1H); 1.18 (s, 3H); 1.07 (dd, J=5.1, 8.9 Hz, 1H); 0.59 (t, J=5.3 Hz, 1H).

MS (ESI, m/z): no mass detected for C$_9$H$_{12}$O$_2$Br$_2$; t$_R$=0.91 min.

X.vi. ((1S,2S)-2-(bromoethynyl)-1-methylcyclopropyl)methyl acetate

Starting from intermediate X.v (1.3 g; 4.2 mmol) and proceeding in analogy to Preparation I, step I.ii, the title compound was obtained, after purification by CC (PE-TBME), as a colourless oil (0.6 g; 62% yield).

$^1$H NMR (CDCl$_3$) δ: 3.89 (d, J=11.4 Hz, 1H); 3.80 (d, J=11.4 Hz, 1H); 2.07 (s, 3H); 1.39 (dd, J=5.5, 8.9 Hz, 1H); 1.27 (s, 3H); 0.94 (dd, J=4.8, 8.9 Hz, 1H); 0.65 (t, J=5.1 Hz, 1H).

MS (ESI, m/z): no mass detected for C$_9$H$_{11}$O$_2$Br; t$_R$=0.86 min.

Preparation Y tert-butyl (1-(iodoethynyl)cyclopropyl)carbamate

Starting from tert-butyl (1-ethynylcyclopropyl)carbamate (0.885 g; 4.88 mmol; commercial) and proceeding in analogy to Preparation Q, the title compound was obtained as a crude light yellow solid (1.36 g; 91% yield).

$^1$H NMR (CDCl$_3$) δ: 5.00 (br. s, 1H); 1.49 (s, 9H); 1.23 (s, 2H); 1.11 (s, 2H).

Preparation Z (S)-4-((1R,2R)-2-(bromoethynyl)cyclopropyl)-2,2-dimethyl-1,3-dioxolane Starting from (1R,2R)-2-((S)-2,2-dimethyl-1,3-dioxolan-4-yl)cyclopropane-1-carbaldehyde (1 g; 5.88 mmol; prepared as described in Mohapatra et al., *Tetrahedron Lett.* (2012), 53(49), 6718-6720) and proceeding successively in analogy to Preparation I, step I.i (79% yield) and Preparation N, step N.v (92% yield), the title compound was obtained, after purification by CC (PE-TBME), as a colourless oil (1.05 g).

$^1$H NMR (CDCl$_3$) δ: 4.08-4.13 (m, 1H); 3.72-3.77 (m, 1H); 3.63-3.68 (m, 1H); 1.41 (s, 3H); 1.20-1.35 (overlapped m, 2H); 1.32 (s, 3H); 0.83-1.00 (m, 2H).

MS (ESI, m/z): no mass detected for $C_{10}H_{13}O_2Br$; $t_R$=0.83 min.

Preparation AA tert-butyl (2-((3-(iodoethynyl)cyclopentyl)amino)-2-oxoethyl)carbamate AA.i. Methyl 3-(2-((tert-butoxycarbonyl)amino) acetamido)cyclopentane-1-carboxylate Starting from methyl 3-aminocyclopentane carboxylate hydrochloride (0.87 g; 4.58 mmol; commercial) and Boc-Gly-OH (0.845 g; 4.82 mmol; commercial) and proceeding in analogy to the Preparation B, step B.iv, the title compound was obtained, without any purification, as a colourless oil (1.41 g; quant.).

$^1$H NMR ($d_6$-DMSO) δ: 7.78 (d, J=7.3 Hz, 1H); 6.86 (t, J=6.0 Hz, 1H); 3.60 (s, 3H); 3.47 (d, J=6.1 Hz, 2H); 2.76-2.85 (m, 1H); 2.08-2.16 (m, 1H); 1.77-1.87 (m, 3H); 1.54-1.62 (m, 1H); 1.41-1.48 (m, 1H); 1.33-1.39 (overlapped m, 1H); 1.37 (s, 9H).

MS (ESI, m/z): 301.05 [M+H$^+$] for $C_{14}H_{24}N_2O_5$; $t_R$=0.67 min.

AA.ii. Tert-butyl (2((3-(hydroxymethyl)cyclopentyl) amino)-2-oxoethyl)carbamate

To a solution of intermediate AA.i (1.38 g; 4.58 mmol) in THF (9 mL) was added DIBAH (1M in toluene; 19 mL) at 0° C. over 90 min, keeping the internal temperature below 5° C. The reaction mixture was stirred overnight at rt. The reaction mixture was quenched with the slow addition of water (11 mL). After 2 h stirring, the mixture was filtered through a Celite bed and the filtrate was evaporated under reduced pressure. The crude was purified by CC (DCM-MeOH) to afford the title compound as a white foam (0.604 g; 48% yield).

$^1$H NMR ($d_6$-DMSO) δ: 7.68 (d, J=7.4 Hz, 1H); 6.82 (t, J=6.0 Hz, 1H); 4.50 (t, J=5.2 Hz, 1H); 3.91-4.06 (m, 1H); 3.46 (d, J=6.0 Hz, 2H); 3.28-3.32 (m, 2H); 1.90-2.02 (m, 2H); 1.72-1.81 (m, 1H); 1.56-1.64 (m, 1H); 1.31-1.44 (overlapped m, 2H); 1.37 (s, 9H); 1.01-1.11 (m, 1H).

MS (ESI, m/z): 273.07 [M+H$^+$] for $C_{13}H_{24}N_2O_4$; $t_R$=0.56 min.

AA.iii. Tert-butyl (24(3-formylcyclopentyl)amino)-2-oxoethyl)carbamate

Starting from intermediate AA.ii (0.604 g; 2.22 mmol) and proceeding in analogy to the Preparation N, step N.iii, the title compound was obtained, after purification by CC (DCM-MeOH), as a yellow oil (0.483 g; 81% yield).

MS (ESI, m/z): 271.09 [M+H$^+$] for $C_{13}H_{22}N_2O_4$; $t_R$=0.59 min.

AA.iv. Tert-butyl (2((3-ethynylcyclopentyl)amino)-2-oxoethyl)carbamate

A suspension of intermediate AA.iii (0.483 g; 1.79 mmol) and $K_2CO_3$ (0.500 g; 3.62 mmol) in MeOH (16 mL) was treated dropwise with dimethyl (1-diazo-2-oxopropyl) phosphonate (0.382 g; 1.99 mmol; commercial). The reaction mixture was stirred at rt overnight. The solvent was evaporated and the residue was dissolved in DCM (15 mL) and water (10 mL). The aq. layer was extracted once with DCM (15 mL). The combined org. layers were washed with brine (10 mL), filtered and concentrated. The crude product was purified by CC (DCM-MeOH) to afford the desired product as a yellow oil (0.416 g; 87% yield).

$^1$H NMR (CDCl$_3$) δ: 6.32 (br. s, 0.5H); 6.03 (br. s, 0.5H); 5.06 (br.s, 1H); 4.30-4.45 (m, 1H); 3.71-3.77 (m, 2H); 2.74-2.86 (m, 1H); 2.17-2.30 (m, 1H); 2.01-2.14 (m, 1.5H); 1.91-2.00 (m, 0.5H); 1.78-1.90 (m, 1H); 1.55-1.76 (m, 2H); 1.38-1.48 (overlapped m, 1H); 1.46 (s, 4.5H); 1.46 (s, 4.5H).

MS (ESI, m/z): 267.10 [M+H$^+$] for $C_{14}H_{22}N_2O_3$; $t_R$=0.71 min.

AA.v. Tert-butyl (2-((3-(iodoethynyl)cyclopentyl) amino)-2-oxoethyl)carbamate

To a solution of intermediate AA.iv (0.416 g; 1.56 mmol) in MeOH (13 mL) and aq. KOH (1M; 12 mL) was added iodine (0.524 g; 2.06 mmol). The reaction mixture was stirred at rt for 2.75 h. Water (30 mL) and DCM (50 mL) were added. The phases were separated and the aq. layer was extracted with DCM-MeOH (9-1; 30 mL), then EA (30 mL). The combined org. layers were washed with brine (20 mL), dried over MgSO$_4$, filtered and evaporated under reduced pressure to afford the title compound as a yellow foam (0.552 g; cis-trans mixture; 90% yield).

$^1$H NMR (CDCl$_3$) δ: 6.13-6.20 (m, 0.5H); 6.01-6.08 (m, 0.5H); 5.08 (br. s, 1H); 4.26-4.41 (m, 1H); 3.75 (d, J=5.3 Hz, 1H); 3.72 (d, J=5.9 Hz, 1H); 2.88-3.00 (m, 1H); 2.26-2.33 (m, 0.5H); 2.16-2.24 (m, 0.5H); 1.99-2.12 (m, 0.5H); 1.90-1.98 (m, 0.5H); 1.67-1.88 (m, 2H); 1.54-1.66 (overlapped m, 1H); 1.36-1.49 (overlapped m, 1H); 1.47 (s, 4.5H); 1.45 (s, 4.5H).

MS (ESI, m/z): 392.88 [M+H$^+$] for $C_{14}H_{21}N_2O_3I$; $t_R$=0.80 min.

Preparation AB tert-butyl (((1R,2R)-2-(iodoethynyl)cyclopropyl) methyl)carbamate AB.i. Tert-butyl (((1R,2R)-2-ethynylcyclopropyl)methyl)carbamate Starting from tert-butyl (((1R,2R)-2-formylcyclopropyl) methyl)carbamate (0.560 g, 2.81 mmol; commercial) and proceeding in analogy to Preparation AA, step AA.iv, the title compound was obtained, without purification, as a yellow oil (0.563 g; quant.).

$^1$H NMR (CDCl$_3$) δ: 4.64 (br. s, 1H); 3.08-3.16 (m, 1H); 2.94-3.00 (m, 1H); 1.80 (d, J=2.1 Hz, 1H); 1.45 (s, 9H); 1.30-1.37 (m, 1H); 1.12-1.18 (m, 1H); 0.89-0.94 (m, 1H); 0.70-0.75 (m, 1H).

AB.ii. Tert-butyl (((1R,2R)-2-(iodoethynyl)cyclopropyl)methyl)carbamate

Starting from intermediate AB.i (0.523 g; 2.68 mmol) and proceeding in analogy to Preparation AA, step AA.v, the title compound was obtained as a yellow oil (0.746 g; 87% yield).

$^1$H NMR (CDCl$_3$) δ: 4.64 (br. s, 1H); 3.08-3.17 (m, 1H); 2.90-2.97 (m, 1H); 1.44 (s, 9H); 1.30-1.38 (m, 1H); 1.24-1.30 (m, 1H); 0.90-0.95 (m, 1H); 0.68-0.74 (m, 1H).

Preparation AC (((1R*,2R*)-2-(bromoethynyl)-2-fluorocyclopropyl)methoxy)(tert-butyl)diphenylsilane

AC.i. ((1R*,2R*)-2-(((tert-butyldiphenylsilyl)oxy)methyl)-1-fluorocyclopropyl)methanol To a solution of ethyl (1R*,2R *)-2-(((tert-butyldiphenylsilyl)oxy)methyl)-1-fluorocyclopropane-1-carboxylate (0.5 g; 1.25 mmol; prepared as described in Sakagami et al., *Bioorg. Med. Chem.* (2008), 16(8), 4359-4366) in THF (9 mL), cooled to −78° C., was added dropwise LiBH$_4$ (2M in THF; 2.2 mL; 4.4 mmol). The reaction mixture was allowed to reach rt and stirred at rt for 24 h. MeOH (2 mL) was carefully added, the reaction mixture was stirred for 20 min, concentrated to dryness and partitioned between water (10 mL) and DCM (15 mL). The aq. layer was extracted with DCM (2×10 mL). The combined org. layers were dried over Na$_2$SO$_4$ and filtered. After concentration of the filtrate to dryness, the title compound was obtained as a colourless oil (0.429 g; 96% yield).

$^1$H NMR (CDCl$_3$) δ: 7.66-7.72 (m, 4H); 7.36-7.45 (m, 6H); 3.89 (ddd, J=1.6, 6.0, 11.0 Hz, 1H); 3.80-3.83 (m, 1H); 3.70-3.78 (m, 2H); 1.74 (t, J=6.4 Hz, 1H); 1.24-1.33 (m, 1H); 1.05 (s, 9H); 0.79-0.88 (m, 2H).

MS (ESI, m/z): 358.95 [M+H$^+$] for C$_2$,H$_{27}$O$_2$FSi; t$_R$=1.01 min.

AC. ii. (((1R*,2R*)-2-(bromoethynyl)-2-fluorocyclopropyl)methoxy)(tert-butyl)diphenylsilane Starting from intermediate AC.i (2.04 g; 5.7 mmol) and proceeding successively in analogy to Preparation N, steps N.iii (83% yield), N.iv (17% yield) and N.v (99% yield), the title compound was obtained as a brown oil (0.351 g).

$^1$H NMR (CDCl$_3$) δ: 7.66-7.70 (m 4H); 7.36-7.45 (m, 6H); 3.84 (ddd, J=1.6, 5.8, 11.3 Hz, 1H); 3.71 (ddd, J=1.1, 8.0, 11.3 Hz, 1H); 1.56-1.64 (m, 1H); 1.14-1.20 (m, 1H); 1.06 (s, 9H); 0.98-1.04 (m, 1H).

Preparation AD (1-(bromoethynyl)cyclopropyl)methyl di-tert-butyl phosphate

AD.i. Di-tert-butyl ((1-(((tert-butyldiphenylsilypoxy)methyl)cyclopropyl)methyl) phosphate To a solution of (1-(((tert-butyldiphenylsilyl)oxy)methyl)cyclopropyl)methanol (13.1 g, 38.5 mmol, prepared as described in WO 2010/135536) in THF (140 mL) at rt was added tetrazole (0.45M in MeCN; 170 mL) and di-tert-butyl diisopropylphosphoramidite (17.2 mL; 51.8 mmol). The reaction mixture was stirred at 40° C. overnight. 35% H$_2$O$_2$ (330 mL) and was added slowly at 0° C. over 75 min, keeping the internal temperature below 10° C. After stirring 1 h at 10° C., water (400 mL) was added. The aq. layer was extracted with EA (3×100 mL). The combined org. layers were collected, washed with 10% aq. NaHSO$_3$ (5×100 mL) and brine (100 mL), dried over MgSO$_4$, filtered and concentrated to dryness. The residue was purified by CC (Hept-EA) to afford a colourless oil (7.16 g; 35% yield).

$^1$H NMR (CDCl$_3$) δ: 7.62-7.68 (m, 4H); 7.35-7.45 (m, 6H); 3.97 (d, J=5.5 Hz, 2H); 3.60 (s, 2H); 1.46 (s, 18H); 1.05 (s, 9H); 0.50-0.53 (m, 2H); 0.40-0.44 (m, 2H).

MS (ESI, m/z): 533.10 [M+H$^{+]}$ for C$_{29}$H$_{45}$O$_5$PSi; t$_R$=1.15 min.

AD.ii. Di-tert-butyl ((1-(hydroxymethyl)cyclopropyl)methyl) phosphate

To a solution of intermediate AD.i (7.16 g; 13.4 mmol) in THF (32 mL) was added TBAF (1M in THF; 27 mL). The reaction proceeded at rt for 3.5 h. The reaction mixture was concentrated in vacuo and the residue (15.62 g) was purified by CC (DCM-MeOH) to give the title compound as a colourless oil (3.72 g; 94% yield).

$^1$H NMR (500 MHz, CDCl$_3$) δ: 3.92 (d, J=9.0 Hz, 2H); 3.52 (s, 2H); 1.49 (s, 18H); 0.53-0.55 (m, 4H).

MS (ESI, m/z): 295.03 [M+H$^+$] for C$_{13}$H$_{27}$O$_5$P; t$_R$=0.72 min.

AD. iii. Di-tert-butyl ((1-formylcyclopropyl)methyl) phosphate

Starting from intermediate AD.ii (3.69 g, 12.5 mmol) and proceeding in analogy to Preparation N, step N.iii (85% yield), the title compound was obtained as a colourless oil (3.12 g).

$^1$H NMR (CDCl$_3$) δ: 9.08 (s, 1H); 4.20 (d, J=6.7 Hz, 2H); 1.48 (s, 18H); 1.20-1.30 (m, 4H).

MS (ESI, m/z): 293.00 [M+H$^+$] for C$_{13}$H$_{25}$O$_5$P; t$_R$=0.77 min.

AD. iv. Di-tert-butyl ((1-ethynylcyclopropyl)methyl) phosphate

A suspension of intermediate AD.iii (1 g; 3.44 mmol) and K$_2$CO$_3$ (0.947 g; 6.85 mmol) in MeOH (30 mL) was treated dropwise with dimethyl(1-diazo-2-oxo-propyl)phosphate (0.992 g, 5.16 mmol). The reaction mixture was stirred at rt overnight. The solvent was evaporated and the residue was dissolved in DCM (30 mL) and water (30 mL). The aq. layer was extracted with EA (20 mL). The combined org. layer were dried over MgSO$_4$, filtered and concentrated to dryness to afford the title compound as a yellow oil (0.93 g; 94% yield).

$^1$H NMR (CDCl$_3$) δ: 3.87 (d, J=6.4 Hz, 2H); 1.90 (s, 1H); 1.49 (s, 18H); 0.98-1.01 (m, 2H); 0.88-0.91 (m, 2H).

MS (ESI, m/z): 289.01 [M+H$^+$] for C$_{14}$H$_{25}$O$_4$P; t$_R$=0.85 min.

AD.v. (1-(bromoethynyl)cyclopropyl)methyl di-tert-butyl phosphate

To a solution of intermediate AD.iv (0.93 g, 3.22 mmol) and NBS (0.691 g, 3.88 mmol) in acetone (13 mL) was added AgNO$_3$ (0.0586 g, 0.345 mmol). The mixture was stirred at rt for 2.25 h. The reaction mixture was filtered through Celite and the filtrate was concentrated to dryness. The residue was purified by CC (Hept-EA) to give the title compound as a colourless oil (1.07 g, 91% yield).

$^1$H NMR (CDCl$_3$) δ: 3.84 (d, J=6.3 Hz, 2H); 1.49 (s, 18H); 0.98-1.01 (m, 2H); 0.86-0.88 (m, 2H).

MS (ESI, m/z): 368.80 [M+H$^+$] for C$_{14}$H$_{24}$O$_4$BrP; $t_R$=0.92 min.

Preparation AE ((1R*,2R*)-2-(bromoethynyl)-1-fluorocyclopropyl) methyl acetate:

AE.i. ((1R*,2R*)-2-(((tert-butyldiphenylsilyl)oxy) methyl)-1-fluorocyclopropyl)methyl acetate Starting from intermediate AC.i (2.12 g; 5.91 mmol) and proceeding in analogy to Preparation X, step X.i, the crude product was obtained as a yellow oil (2.3 g).

$^1$H NMR (CDCl$_3$) δ: 7.66-7.71 (m, 4H); 7.36-7.45 (m, 6H); 4.27-4.35 (m, 2H); 3.90 (ddd, J=1.6, 5.8, 11.0 Hz, 1H); 3.69 (ddd, J=1.2, 8.3, 11.0 Hz, 1H); 2.11 (s, 3H); 1.31-1.40 (m, 1H); 1.06 (s, 9H); 0.80-0.94 (m, 2H).

MS1 (ESI, m/z): 400.98 [M+H$^+$] for C$_{12}$H$_{18}$NO$_2$; $t_R$=1.09 min.

AE.ii. ((1R,2R)-1-fluoro-2-(hydroxymethyl)cyclopropyl)methyl acetate

To a solution of intermediate AE.i (2.16 g; 5.39 mmol) in THF (10 mL) was added TBAF (1M in THF; 7 mL). The reaction mixture was stirred at rt for 1 h. The reaction mixture was concentrated in vacuo and purified by CC (DCM-MeOH) to afford the title alcohol as a yellow oil (0.726 g; 83% yield).

$^1$H NMR (CDCl$_3$) δ: 4.27-4.41 (m, 2H); 3.94 (m, 1H); 3.64 (m, 1H); 2.13 (s, 3H); 1.51 (m, 1H); 1.41 (m, 1H); 0.98-1.06 (m, 2H)

AE.iii. ((1R,2R)-2-(bromoethynyl)-1-fluorocyclopropyl)methyl acetate

Starting from intermediate AE.ii (0.725 g; 4.46 mmol) and proceeding successively in analogy to Preparation N, step N.iii (100% yield), step N.iv (52% yield) and step N.v (57% yield), the title compound was obtained as a colourless oil (0.351 g).

$^1$H NMR (CDCl$_3$) δ: 6.21 (dd, J=1.3, 8.8 Hz, 1H); 4.32-4.38 (m, 2H); 2.14 (s, 3H); 1.90-1.98 (m, 1H); 1.22-1.35 (m, 2H).

Preparation AF ((1-(bromoethynyl)cyclobutyl)methoxy)(tert-butyl) diphenylsilane:

Starting from cyclobutane-1,1-diyldimethanol (3.03 g; 24.8 mmol; commercial) and proceeding successively in analogy to Preparation N, steps N.ii (98% yield), N.iii (86% yield), N.iv (93% yield) and N.v (quant.), the title compound was obtained as a colourless oil (4.79 g).

$^1$H NMR (CDCl$_3$) δ: 7.70-7.74 (m 4H); 7.40-7.48 (m, 6H); 3.67 (s, 2H); 2.18-2.29 (m, 4H); 2.00-2.08 (m, 1H); 1.86-1.95 (m, 1H); 1.11 (s, 9H).

Preparation AG 3-(3-iodoprop-2-yn-1-yl)oxetan-3-ol

A flask charged with ZnBr$_2$ (1.08 g, 4.80 mmol) and Mg turnings (5.85 g) was heated with stirrring under vacuum at 150° C. for 2 h and then cooled to rt. Et$_2$O (90 mL) and a few drops of 1,2-dibromoethane were added. Propargyl bromide (9 mL; 118.78 mmol) in Et$_2$O (70 mL) was then added dropwise. The mixture was stirred at the same temperature for 1 h. In a separate flask were introduced 3-oxetanone (3.15 g; 43.71 mmol) and THF (420 mL).

The Grignard reagent solution (127 mL; 65.56 mmol), cannulated in a graduated addition funnel, was added dropwise. The solution was stirred at the same temperature for 1 h and diluted with sat. aq. NH$_4$Cl and Hex (100 mL). The two layers were separated and the aq. layer was extracted with Hex (100 mL). The combined org. layers were dried over MgSO$_4$, filtered and concentrated under reduced pressure. Starting from the crude intermediate thus obtained (4.33 g; 38.63 mmol) and proceeding in analogy to Preparation K, the title compound was obtained as a yellow solid (3.01 g; 33% yield).

$^1$H NMR (CDCl$_3$) δ: 4.51 (d, J=7.4 Hz, 2H); 4.66 (d, J=7.1 Hz, 2H); 2.98 (s, 2H); 2.55 (s, 1H).

REFERENCE EXAMPLES

Reference Example 1

(RS)-4-(7-(2-fluoro-4-(3-morpholinopropoxy)phenyl)-4-oxoquinazolin-3(4H)-yl)-N-hydroxy-2-methyl-2-(methylsulfonyl)butanamide formate

RE1.i. (RS)-4-(7-(2-fluoro-4-(3-morpholinopropoxy)phenyl)-4-oxoquinazolin-3(4H)-yl)-2-methyl-2-(methylsulfonyl)-N-((tetrahydro-2H-pyran-2-ypoxy)butanamide:

Starting from the compound of Preparation B (0.249 g; 0.50 mmol) and the compound of Preparation C (0.230 g; 0.63 mmol) and proceeding in analogy to Procedure A, the title product was obtained, after purification by CC (DCM-MeOH, then DCM-MeOH+1% NH$_4$OH), as an off-white foam (0.235 g; 72% yield).

$^1$H NMR (d$_6$-DMSO) δ: 11.42 (s, 1H); 8.38 (s, 0.5H); 8.36 (s, 0.5H); 8.21 (d, J=8.5 Hz, 1H); 7.78 (s, 1H); 7.68-7.73 (m, 1H); 7.55-7.64 (m, 1H); 6.91-7.05 (m, 2H); 4.93-4.97 (m, 0.5H); 4.89-4.92 (m, 0.5H); 3.84-4.22 (m, 5H); 3.46-3.62 (m, 5H); 3.09 (s, 1.5H); 3.07 (s, 1.5H); 2.18-2.69 (overlapped m, 8H); 1.84-1.97 (m, 2H); 1.47-1.72 (overlapped m, 6H); 1.63 (s, 1.5H); 1.62 (s, 1.5H).

MS (ESI, m/z): 661.3 [M+H$^+$] for C$_{32}$H$_{41}$N$_4$O$_8$FS; $t_R$=0.66 min.

RE1.ii. (RS)-4-(7-(2-fluoro-4-(3-morpholinopropoxy)phenyl)-4-oxoquinazolin-3(4H)-yl)-N-hydroxy-2-methyl-2-(methylsulfonyl)butanamide formate:

Starting from intermediate RE1.i (0.235 g; 0.36 mmol) and using Procedure B, the title product was obtained, after purification by prep-HPLC (Method 1), as an off-white solid (0.136 g; 61% yield).

$^1$H NMR (d$_6$-DMSO) δ: 11.00 (s, 1H); 9.23 (s, 1H); 8.38 (s, 1H); 8.22 (d, J=8.3 Hz, 1H); 8.13 (s, 1H); 7.79 (s, 1H); 7.60-7.74 (m, 2H); 6.93-7.07 (m, 2H); 4.09-4.21 (m, 3H); 3.83-4.04 (m, 3H); 3.59-3.80 (m, 2H); 3.10 (s, 3H); 2.40-2.65 (overlapped m, 5H); 2.08-2.29 (m, 5H); 1.61 (s, 3H).

MS (ESI, m/z): 577.2 [M+H$^+$] for C$_{28}$H$_{35}$N$_4$O$_9$FS; $t_R$=0.49 min.

Reference Example 2

(RS)-N-hydroxy-2-methyl-2-(methylsulfonyl)-4-(7-(4-(3-morpholinopropoxy)phenyl)-4-oxoquinazolin-3(4H)-yl)butanamide formate Starting from the compound of Preparation B (0.158 g; 0.315 mmol) and (4-(3-morpholinopropoxy)phenyl)boronic acid (0.096 g; 0.362 mmol; commercial) and proceeding in analogy to Procedure A (84% yield) and Procedure B (64% yield), the title product was obtained, after purification by prep-HPLC (Method 1), as a white foam (0.100 g).

$^1$H NMR (d$_6$-DMSO) δ: 11.01 (br. s, 1H); 9.23 (br. s, 1H); 8.37 (s, 1H); 8.19 (d, J=8.3 Hz, 1H); 8.13 (s, 1H); 7.77-7.92 (overlapped m, 2H); 7.81 (d, J=8.7 Hz, 2H); 7.10 (d, J=8.7 Hz, 2H); 4.09-4.21 (m, 3H); 3.70-3.97 (m, 5H); 3.15-3.49 (overlapped m, 4H); 3.10 (s, 3H); 2.47-2.65 (overlapped m, 3H); 2.11-2.29 (m, 3H); 1.61 (s, 3H).

MS (ESI, m/z): 559.1 [M+H$^+$] for C$_{28}$H$_{36}$N$_4$O$_9$S; t$_R$=0.55 min.

Reference Example 3

(RS)-4-(7-(2-fluoro-4-(2-morpholinoethoxy)phenyl)-4-oxoquinazolin-3(4H)-yl)-N-hydroxy-2-methyl-2-(methylsulfonyl)butanamide formate Starting from the compound of Preparation B (0.123 g; 0.245 mmol) and 4-(2-(4-(4,4,5,5-tetramethyl-1,3-dioxolan-2-yl)phenoxy)ethyl)morpholine (0.137 g; 0.292 mmol; commercial) and proceeding in analogy to Procedure A (49% yield) and Procedure B (50% yield), the title product was obtained, after purification by prep-HPLC (Method 1), as a white foam (0.0364 g).

$^1$H NMR (d$_6$-DMSO) δ: 11.00 (br. s, 1H); 9.23 (br. s, 1H); 8.39 (s, 1H); 8.22 (d, J=8.4 Hz, 1H); 8.13 (s, 1H); 7.79 (s, 1H); 7.62-7.75 (m, 2H); 6.99-7.17 (m, 2H); 4.37-4.51 (m, 2H); 4.10-4.22 (m, 1H); 3.84-4.06 (m, 3H); 3.42-3.80 (m, 4H); 3.10 (s, 3H); 2.41-2.66 (overlapped m, 5H); 2.16-2.30 (m, 1H); 1.62 (s, 3H).

MS (ESI, m/z): 563.1 [M+H$^+$] for C$_{27}$H$_{33}$N$_4$O$_9$FS; t$_R$=0.54 min.

Reference Example 4

(RS)-4-(7-(2-fluoro-3-methoxyphenyl)-4-oxoquinazolin-3(4H)-yl)-N-hydroxy-2-methyl-2-(methylsulfonyl)butanamide

RE4.i. (RS)-4-(7-(2-fluoro-3-methoxyphenyl)-4-oxoquinazolin-3(4H)-yl)-2-methyl-2-(methylsulfonyl)-N-((tetrahydro-2H-pyran-2-yl)oxy)butanamide Starting from the compound of Preparation B (0.114 g; 0.226 mmol) and 2-fluoro-3-methoxyphenylboronic acid (0.045 g; 0.270 mmol; commercial) and proceeding in analogy to Procedure A, the title product was obtained, after purification by CC (Hept-EA), as a colourless gum (0.079 g; 64% yield).

$^1$H NMR (d$_6$-DMSO) δ (mixture of diastereoisomers): 11.41 (br. s, 1H); 8.39 (s, 0.5H); 8.37 (s, 0.5H); 8.23 (d, J=8.3 Hz, 1H); 7.80 (s, 1H); 7.68-7.74 (m, 1H); 7.23-7.32 (m, 2H); 7.12-7.21 (m, 1H); 4.93-4.96 (m, 0.5H); 4.88-4.92 (m, 0.5H); 3.90 (s, 3H); 3.83-4.23 (overlapped m, 3H); 3.46-3.56 (m, 1H); 3.09 (s, 1.5H); 3.07 (s, 1.5H); 2.44-2.68 (overlapped m, 1H); 2.17-2.32 (m, 1H); 1.63 (s, 1.5H); 1.62 (s, 1.5H); 1.60-1.73 (overlapped m, 3H); 1.48-1.58 (m, 3H).

MS (ESI, m/z): 548.1 [M+H$^+$] for C$_{26}$H$_{30}$N$_3$O$_7$FS; t$_R$=0.83 min.

RE4.ii. (RS)-4-(7-(2-fluoro-3-methoxyphenyl)-4-oxoquinazolin-3(4H)-yl)-N-hydroxy-2-methyl-2-(methylsulfonyl)butanamide Starting from intermediate RE4.i (0.079 g; 0.14 mmol) and using Procedure D, the title product was obtained, after filtration and drying to a constant weight, as a white solid (0.046 g; 68% yield).

$^1$H NMR (d$_6$-DMSO) δ: 11.00 (d, J=1.5 Hz, 1H); 9.23 (d, J=1.5 Hz, 1H); 8.39 (s, 1H); 8.23 (d, J=8.3 Hz, 1H); 7.79-7.82 (m, 1H); 7.69-7.74 (m, 1H); 7.25-7.30 (m, 2H); 7.13-7.21 (m, 1H); 4.10-4.22 (m, 1H); 3.90 (s, 3H); 3.84-3.96 (overlapped m, 1H); 3.10 (s, 3H); 2.48-2.65 (overlapped m, 1H); 2.16-2.29 (m, 1H); 1.61 (s, 3H).

MS (ESI, m/z): 464.1 [M+H$^+$] for C$_{21}$H$_{22}$N$_3$O$_6$FS; t$_R$=0.71 min.

Reference Example 5

(RS)-4-(7-(3-fluoro-4-methoxyphenyl)-4-oxoquinazolin-3(4H)-yl)-N-hydroxy-2-methyl-2-(methylsulfonyl)butanamide Starting from the compound of Preparation B (0.101 g; 0.202 mmol) and 3-fluoro-4-methoxyphenylboronic acid (0.045 g; 0.264 mmol; commercial) and proceeding successively in analogy to Procedure A (73% yield) and Procedure D (87% yield), the title product was obtained, after precipitation in water, as a white solid (0.059 g).

$^1$H NMR (d$_6$-DMSO) δ: 11.00 (s, 1H); 9.23 (s, 1H); 8.37 (s, 1H); 8.19 (d, J=8.3 Hz, 1H); 7.95 (d, J=1.5 Hz, 1H); 7.88 (dd, J=1.5, 8.3 Hz, 1H); 7.76 (dd, J=2.2, 12.9 Hz, 1H); 7.64-7.70 (m, 1H); 7.26-7.35 (m, 1H); 4.09-4.20 (m, 1H); 3.91 (s, 3H); 3.83-3.95 (overlapped m, 1H); 3.10 (s, 3H); 2.36-2.65 (overlapped m, 1H); 2.15-2.30 (m, 1H); 1.61 (s, 3H).

MS (ESI, m/z): 464.1 [M+H$^+$] for C$_{21}$H$_{22}$N$_3$O$_6$FS; t$_R$=0.71 min.

Reference Example 6

(RS)-4-(7-(4-(dimethylamino)phenyl)-4-oxoquinazolin-3(4H)-yl)-N-hydroxy-2-methyl-2-(methylsulfonyl)butanamide Starting from the compound of Preparation B (0.0816 g; 0.162 mmol) and 4-(N,N-dimethylamine)phenylboronic acid (0.036 g; 0.214 mmol; commercial) and proceeding successively in analogy to Procedure A (74% yield) and Procedure D (73% yield), the title product was obtained, after precipitation in water, as a yellow solid (0.040 g).

$^1$H NMR (d$_6$-DMSO) δ: 11.00 (s, 1H); 9.23 (s, 1H); 8.33 (s, 1H); 8.14 (d, J=8.5 Hz, 1H); 7.78-783 (m, 2H); 7.70 (d, J=8.5 Hz, 2H); 6.84 (d, J=8.8 Hz, 2H); 4.07-4.20 (m, 1H); 3.80-3.94 (m, 1H); 3.10 (s, 3H); 2.98 (s, 6H); 2.43-2.65 (overlapped m, 1H); 2.15-2.29 (m, 1H); 1.61 (s, 3H).

MS (ESI, m/z): 459.1 [M+H$^+$] for C$_{22}$H$_{26}$N$_4$O$_5$S; t$_R$=0.58 min.

Reference Example 7

(RS)-N-hydroxy-4-(7-(4-(hydroxymethyl)phenyl)-4-oxoquinazolin-3(4H)-yl)-2-methyl-2-(methylsulfonyl)butanamide Starting from the compound of Preparation B (0.094 g; 0.187 mmol) and 4-(hydroxymethyl)phenylboronic acid (0.031 g; 0.200 mmol) and proceeding successively in analogy to Procedure A (73% yield) and Procedure D (66% yield), the title product was obtained, after precipitation in water, as a white solid (0.039 g).

$^1$H NMR (d$_6$-DMSO) δ: 11.00 (br. s, 1H); 9.22 (br. s, 1H); 8.38 (s, 1H); 8.22 (d, J=8.3 Hz, 1H); 7.93 (d, J=1.6 Hz, 1H); 7.88 (dd, J=1.6, 8.3 Hz, 1H); 7.79 (d, J=8.3 Hz, 2H); 7.47 (d, J=8.3 Hz, 2H); 5.26 (t, J=5.8 Hz, 1H); 4.57 (d, J=5.8 Hz, 2H); 4.09-4.22 (m, 1H); 3.83-3.96 (m, 1H); 3.10 (s, 3H); 2.46-2.66 (overlapped m, 1H); 2.15-2.30 (m, 1H); 1.61 (s, 3H).

MS (ESI, m/z): 446.1 [M+H$^+$] for C$_{21}$H$_{23}$N$_3$O$_6$S; t$_R$=0.59 min.

Reference Example 8

(RS)-N-hydroxy-2-methyl-2-(methylsulfonyl)-4-(7-(4-(morpholinomethyl)phenyl)-4-oxoquinazolin-3(4H)-yl)butanamide formate Starting from the compound of Preparation B (0.079 g; 0.157 mmol) and 4-(4-(4,4,5,5-tetramethyl-1,3,2-dioxaborolan-2-yl)benzyl)morpholine (0.066 g; 0.218 mmol) and proceeding successively in analogy to Procedure A (94% yield) and Procedure B (58% yield), the title product was obtained, after purification by prep-HPLC (Method 1) and trituration in Et$_2$O, as a white solid (0.045 g).

$^1$H NMR (d$_6$-DMSO) δ: 11.01 (s, 1H); 9.23 (br. s, 1H); 8.40 (s, 1H); 8.25 (d, J=8.3 Hz, 1H); 8.13 (s, 1H); 7.89-8.02 (m, 4H); 7.60-7.68 (m, 2H); 4.35-4.52 (m, 2H); 4.10-4.23 (m, 1H); 3.83-4.05 (m, 3H); 3.55-3.74 (m, 2H); 3.04-3.47 (overlapped m, 4H); 3.10 (s, 3H); 2.41-2.66 (overlapped m, 1H); 2.15-2.30 (m, 1H); 1.62 (s, 3H).

MS (ESI, m/z): 515.2 [M+H$^+$] for C$_{26}$H$_{32}$N$_4$O$_8$S; t$_R$=0.50 min.

Reference Example 9

(RS)-4-(6-fluoro-4-oxo-7-phenylquinazolin-3(4H)-yl)-N-hydroxy-2-methyl-2-(methylsulfonyl)butanamide Starting from the compound of Preparation D (0.071 g; 0.136 mmol) and phenylboronic acid (0.022 g; 0.169 mmol) and proceeding successively in analogy to Procedure A (77% yield) and Procedure D (50% yield), the title product was obtained, after precipitation in water, as a white solid (0.023 g).

$^1$H NMR (d$_6$-DMSO) δ: 10.99 (s, 1H); 9.22 (s, 1H); 8.38 (s, 1H); 7.94 (d, J=10.4 Hz, 1H); 7.83 (d, J=7.1 Hz, 1H); 7.63-7.71 (m, 2H); 7.48-7.59 (m, 3H); 4.07-4.22 (m, 1H); 3.84-3.98 (m, 1H); 3.09 (s, 3H); 2.43-2.66 (overlapped m, 1H); 2.15-2.29 (m, 1H); 1.61 (s, 3H).

MS (ESI, m/z): 433.9 [M+H$^+$] for C$_{20}$H$_{20}$N$_3$O$_5$FS; t$_R$=0.72 min.

Reference Example 10

(RS)-N-hydroxy-4-(7-((4-(hydroxymethyl)phenyl)ethynyl)-4-oxoquinazolin-3(4H)-yl)-2-methyl-2-(methylsulfonyl)butanamide Starting from the compound of Preparation B (0.217 g; 0.43 mmol) and 4-ethynylbenzyl alcohol (0.113 g; 0.85 mmol), and proceeding successively in analogy to Procedure E (38% yield) and Procedure D (40% yield), the title product was obtained, after purification by prep-HPLC (Method 1), as a white solid (0.031 g).

$^1$H NMR (d$_6$-DMSO) δ: 10.99 (s, 1H); 9.22 (s, 1H); 8.39 (s, 1H); 8.17 (d, J=8.2 Hz, 1H); 7.82 (s, 1H); 7.67 (dd, J=1.4, 8.2 Hz, 1H); 7.59 (d, J=8.2 Hz, 2H); 7.41 (d, J=8.2 Hz, 2H); 5.30 (t, J=5.8 Hz, 1H); 4.55 (d, J=5.8 Hz, 2H); 4.07-4.19 (m, 1H); 3.82-3.94 (m, 1H); 3.09 (s, 3H); 2.43-2.66 (overlapped m, 1H); 2.14-2.29 (m, 1H); 1.61 (s, 3H).

MS (ESI, m/z): 470.1 [M+H$^+$] for C$_{23}$H$_{23}$N$_3$O$_6$S; t$_R$=0.66 min.

Reference Example 11

(RS)-N-hydroxy-4-(7-((4-(3-hydroxyoxetan-3-yl)phenyl)ethynyl)-4-oxoquinazolin-3(4H)-yl)-2-methyl-2-(methylsulfonyl)butanamide Starting from the compound of Preparation E (0.100 g; 0.223 mmol) and the compound of Preparation F (0.068 g; 0.246 mmol) and proceeding successively in analogy to Procedure F (70% yield) and Procedure D (27% yield), the title product was obtained, after purification by prep-HPLC (Method 1), as a yellow solid (0.022 g).

$^1$H NMR (d$_6$-DMSO) δ: 11.00 (br. s, 1H); 9.23 (br. s, 1H); 8.39 (s, 1H); 8.18 (d, J=8.2 Hz, 1H); 7.84 (d, J=1.2 Hz, 1H); 7.64-7.74 (m, 5H); 6.48 (s, 1H); 4.80 (d, J=6.6 Hz, 2H); 4.69 (d, J=6.6 Hz, 2H); 4.07-4.20 (m, 1H); 3.83-3.96 (m, 1H); 3.09 (s, 3H); 2.43-2.66 (overlapped m, 1H); 2.14-2.29 (m, 1H); 1.61 (s, 3H).

MS (ESI, m/z): 512.1 [M+H$^+$] for C$_{25}$H$_{25}$N$_3$O$_7$S; t$_R$=0.65 min.

Reference Example 12

(RS)-N-hydroxy-2-methyl-2-(methylsulfonyl)-4-(7-((4-(morpholinomethyl)phenyl)ethynyl)-4-oxoquinazolin-3(4H)-yl)butanamide formate Starting from the compound of Preparation B (0.181 g; 0.359 mmol) and 4-(4-ethynylbenzyl)morpholine (0.050 g; 0.377 mmol; prepared as described in Oddo and Holl, *Carbohydrate Research* 2012(359), 59-64) and proceeding successively in analogy to Procedure E (11% yield) and Procedure D (61% yield), the title product was obtained, after purification by prep-HPLC (Method 1), as a brown solid (0.014 g).

$^1$H NMR (d$_6$-DMSO) δ: 10.99 (s, 1H); 9.22 (s, 1H); 8.39 (s, 1H); 8.18 (d, J=8.2 Hz, 1H); 8.13 (s, 1H); 7.83 (s, 1H); 7.56-7.71 (m, 3H); 7.38-7.51 (m, 2H); 4.06-4.23 (m, 1H); 3.80-3.99 (m, 1H); 3.45-3.70 (m, 6H); 3.09 (s, 3H); 2.11-2.66 (overlapped m, 6H); 1.61 (s, 3H).

MS (ESI, m/z): 539.2 [M+H$^+$] for C$_{28}$H$_{32}$N$_4$O$_8$S; t$_R$=0.56 min.

EXAMPLES OF COMPOUNDS ACCORDING TO THE INVENTION

Example 1

(R)-4-(7-(2-fluoro-4-methoxyphenyl)-4-oxoquinazolin-3(4H)-yl)-N-hydroxy-2-methyl-2-(methylsulfonyl)butanamide 1.i. (RS)-4-(7-(2-fluoro-4-methoxyphenyl)-4-oxoquinazolin-3(4H)-yl)-2-methyl-2-(methylsulfonyl)-N-((tetrahydro-2H-pyran-2-yl)oxy)butanamide Starting from the compound of Preparation B (0.186 g; 0.37 mmol) and 2-fluoro-4-methoxyphenylboronic acid (0.066 g; 0.38 mmol) and using Procedure A, the title product was obtained, after purification by CC (Hept-EA), as a yellowish gum (0.144 g, 71% yield).

$^1$H NMR (d$_6$-DMSO) δ: (mixture of diastereoisomers) 11.42 (br. s, 1H); 8.38 (s, 0.5H); 8.36 (s, 0.5H); 8.21 (d, J=8.3 Hz, 1H); 7.78 (s, 1H); 7.67-7.73 (m, 1H); 7.51-7.66 (m, 1H); 6.91-7.05 (m, 2H); 4.93-4.96 (m, 0.5H); 4.88-4.92 (m, 0.5H); 3.88-4.23 (m, 3H); 3.84 (s, 3H); 3.44-3.57 (m, 1H); 3.09 (s, 1.5H); 3.07 (s, 1.5H); 2.41-2.76 (overlapped m, 1H); 2.17-2.31 (m, 1H); 1.63 (s, 1.5H); 1.62 (s, 1.5H); 1.59-1.71 (overlapped m, 3H); 1.48-1.58 (m, 3H).

MS (ESI, m/z): 548.2 [M+H$^+$] for C$_{26}$H$_{30}$N$_3$O$_7$FS; $t_R$=0.86 min.

1.ii. (R)-4-(7-(2-fluoro-4-methoxyphenyl)-4-oxoquinazolin-3(4H)-yl)-N-hydroxy-2-methyl-2-(methylsulfonyl)butanamide Starting from intermediate 1.i (0.144 g; 0.262 mmol) and proceeding in analogy to Procedure D, the racemic mixture was obtained, after precipitation in water, as a white solid (0.082 g). The products were separated by semi-preparative chiral HPLC Method A (Hept-MeOH-EtOH-TFA 20-40-40-0.8; flow rate: 24 mL/min, UV detection at 265 nm), the respective retention times (flow rate: 1.2 mL/min) were 13.6 and 19.7 min. The title enantiomer was identified as the first-eluting enantiomer and was obtained as a pinkish orange solid (0.030 g).

$^1$H NMR (d$_6$-DMSO) δ: 11.00 (s, 1H); 9.23 (br. s, 1H); 8.38 (s, 1H); 8.21 (d, J=8.3 Hz, 1H); 7.79 (s, 1H); 7.71 (d, J=8.3 Hz, 1H); 7.57-7.66 (m, 1H); 6.91-7.05 (m, 2H); 4.08-4.22 (m, 1H); 3.84 (s, 3H); 3.75-3.99 (overlapped m, 1H); 3.10 (s, 3H); 2.38-2.67 (overlapped m, 1H); 2.15-2.30 (m, 1H); 1.61 (s, 3H).

MS (ESI, m/z): 464.1 [M+H$^+$] for C$_{21}$H$_{22}$N$_3$O$_6$FS; $t_R$=0.72 min.

Example 2

(R)-N-hydroxy-2-methyl-2-(methylsulfonyl)-4-(4-oxo-7-phenylquinazolin-3(4H)-yl)butanamide 2.i. 3-amino-[1,1'-biphenyl]-1-4-carboxylic acid To a mixture of 2-amino-4-bromobenzoic acid (0.992 g; 4.46 mmol), phenylboronic acid (0.832 g; 6.69 mmol) and Pd(PPh$_3$)$_4$ (0.052 g; 0.045 mmol) under nitrogen was added degassed DMF (10 mL) and aq. 1M K$_2$CO$_3$ (7 mL). The resulting mixture was stirred at 80° C. for 16 h. DMF was removed under reduced pressure. The residue was taken up in 4N NaOH (40 mL) and the aq. phase was washed twice with EA (2×50 mL). The pH of the aq. layer was adjusted to 5 by addition of 4N HCl. The aq. phase was extracted three times with EA (3×50 mL) and once with DCM-MeOH 9-1 (50 mL). The combined org. layers were dried over MgSO$_4$ and evaporated under reduced pressure to give a beige solid. It was triturated in Et$_2$O, filtered and dried to give the title compound as a beige solid (0.721 g; 76% yield).

MS (ESI, m/z): 214.3 [M+H$^+$] for C$_{13}$H$_{11}$NO$_2$; $t_R$=0.78 min.

2.ii. 3-amino-N-(2-hydroxyethyl)[1,1'-biphenyl]-4-carboxamide

Starting from intermediate 2.i (0.721 g; 3.38 mmol) and ethanolamine (0.34 mL; 5.65 mmol) and proceeding in analogy to Preparation B, step B.iv, the title compound was obtained as a beige solid (0.820 g; 95% yield).

MS (ESI, m/z): 257.3 [M+H$^+$] for C$_{15}$H$_{16}$N$_2$O$_2$; $t_R$=0.65 min.

2.iii. 3-(2-hydroxyethyl)-7-phenylquinazolin-4(3H)-one

To a solution of intermediate 2.ii (0.147 g; 0.57 mmol) in NMP (0.57 mL) were added triethylorthoformate (0.293 mL; 1.72 mmol) and HCl in dioxane (4N; 0.072 mL). The solution was heated at 110° C. for 3 h, then stirred at rt overnight. Water (10 mL) was added and the mixture was extracted three times with EA (3×10 mL). The combined org. layers were washed twice with water (2×5 mL), then with brine (5 mL). The org. phase was dried over MgSO$_4$ and evaporated under reduced pressure. The crude was purified by CC (Hept-EA) to give the title compound as a white solid (0.095 g; 62% yield).

$^1$H NMR (d$_6$-DMSO) δ: 8.30 (s, 1H); 8.23 (d, J=8.3 Hz, 1H); 7.92-7.95 (m, 1H); 7.79-7.90 (m, 3H); 7.42-7.57 (m, 3H); 4.95 (t, J=5.6 Hz, 1H); 4.06 (t, J=5.2 Hz, 2H); 3.65-3.72 (m, 2H).

MS (ESI, m/z): 267.3 [M+H$^+$] for C$_{16}$H$_{14}$N$_2$O$_2$; $t_R$=0.71 min.

2.iv. 2-(4-oxo-7-phenylquinazolin-3(4H)-yl) ethyl methanesulfonate

To a solution of intermediate 2.iii (0.347 g; 1.3 mmol) in DCM (15 mL), cooled at 0° C., were added TEA (0.364 mL; 2.61 mmol) and MsCl (0.121 mL, 1.57 mmol). The reaction was stirred at 0° C. for 40 min. Sat. aq. NaHCO$_3$ (10 mL) and DCM (5 mL) were added. The two layers were decanted. The aq. layer was extracted once with DCM (10 mL). The combined org. layers were dried over Na$_2$SO$_4$ and concentrated to dryness to give the title compound as a yellow gum (0.476 g; quant.).

$^1$H NMR (d$_6$-DMSO) δ: 8.37 (s, 1H); 8.24 (d, J=8.3 Hz, 1H); 7.93-7.96 (m, 1H); 7.86-7.91 (m, 1H); 7.80-7.85 (m, 2H); 7.43-7.58 (m, 3H); 4.54 (t, J=5.0 Hz, 2H); 4.35 (t, J=5.0 Hz, 2H); 3.17 (s, 3H).

MS (ESI, m/z): 345.2 [M+H$^+$] for C$_{17}$H$_{16}$N$_2$O$_4$S; $t_R$=0.79 min.

2.v. 3-(2-iodoethyl)-7-phenylquinazolin-4(3H)-one

To a suspension of intermediate 2.iv (0.448 g; 1.3 mmol) in 2-butanone (4.5 mL) was added NaI (0.351 g; 2.34 mmol). The mixture was heated at 90° C. for 75 min. After cooling to rt, the reaction mixture was diluted with water (10 mL) and EA (15 mL). The phases were separated and the aq. layer was extracted twice with EA (2×10 mL). The combined org. layers were washed with 10% Na$_2$S$_2$O$_4$ (10 mL) and brine (10 mL), dried over MgSO$_4$ and concentrated to dryness to afford the title product as a pale yellow solid (0.426 g; 87% yield).

$^1$H NMR (d$_6$-DMSO) δ: 8.43 (s, 1H); 8.24 (d, J=8.2 Hz, 1H); 7.94 (d, J=1.6 Hz, 1H); 7.88 (dd, J=1.6, 8.2 Hz, 1H); 7.80-7.86 (m, 2H); 7.43-7.58 (m, 3H); 4.34 (t, J=6.9 Hz, 2H); 3.58 (t, J=6.9 Hz, 2H).

MS (ESI, m/z): 377.0 [M+H$^-$] for C$_{16}$H$_{13}$N$_2$OI; $t_R$=0.89 min.

2.vi. Ethyl (RS)-2-(methylsulfonyl)-4-(4-oxo-7-phenylquinazolin-3(4H)-yl)butanoate To a mixture of NaH (60%; 0.029 g; 0.72 mmol) in DMF (1.8 mL) at 0° C. was slowly added ethylmethanesulfonyl acetate (0.2 mL; 1.47 mmol). The reaction was allowed to warm to rt and stirred for 90 min. A suspension of intermediate 2.v (0.203 g; 0.54 mmol) in DMF (2 mL) was added dropwise and the reaction mixture was stirred at rt for 15 h. Water (10 mL) was added and the mixture was stirred for 5 min. EA (10 mL) was added and the phases were separated. The aq. phase was extracted twice with EA (2×10 mL). The combined org. layers were dried over $Na_2SO_4$ and evaporated under reduced pressure. The residue was purified by CC (Hept-EA) to afford the title product as a colourless gum (0.160 g; 72% yield).

$^1$H NMR ($d_6$-DMSO) δ: 8.36 (s, 1H); 8.22 (d, J=8.3 Hz, 1H); 7.93 (d, J=1.7 Hz, 1H); 7.87 (dd, J=1.7, 8.3 Hz, 1H); 7.80-7.85 (m, 2H); 7.42-7.58 (m, 3H); 4.39-4.46 (m, 1H); 3.97-4.25 (m, 4H); 3.13 (s, 3H); 2.40-2.52 (overlapped m, 2H); 1.14-1.22 (m, 3H).

MS (ESI, m/z): 415.3 [M+H$^+$] for $C_{21}H_{22}N_2O_5S$; $t_R$: 0.83 min.

2.vii. Ethyl (RS)-2-methyl-2-(methylsulfonyl)-4-(4-oxo-7-phenylquinazolin-3(4H)-yl)butanoate To a solution of intermediate 2.vi (0.160 g; 0.39 mmol) in DMF (1.8 mL) was added $Cs_2CO_3$ (0.161 g; 0.49 mmol). The reaction mixture was stirred at rt for 30 min. MeI (0.036 mL; 0.58 mmol) was added to the reaction was stirred at rt for 1 h. Water (10 mL) and EA (10 mL) were added. The phases were separated. The aq. layer was extracted once with EA (10 mL). The combined org. layers were washed with brine (15 mL), dried over $MgSO_4$ and evaporated under reduced pressure to give the title product as a yellow gum (0.166 g; quant.).

$^1$H NMR ($d_6$-DMSO) δ: 8.43 (s, 1H); 8.23 (d, J=8.3 Hz, 1H); 7.93-7.97 (m, 1H); 7.89 (d, J=8.3 Hz, 1H); 7.81-7.86 (m, 2H); 7.41-7.58 (m, 3H); 3.98-4.19 (m, 4H); 3.16 (s, 3H); 2.60-2.75 (m, 1H); 2.23-2.36 (m, 1H); 1.65 (s, 3H); 1.19 (t, J=7.1 Hz, 3H).

MS (ESI, m/z): 429.3 [M+H$^+$] for $C_{22}H_{24}N_2O_5S$; $t_R$: 0.86 min.

2.viii. (RS)-2-methyl-2-(methylsulfonyl)-4-(4-oxo-7-phenylquinazolin-3(4H)-yl)butanoic acid LiOH (56%; 0.050 g; 0.67 mmol) was added to a solution of intermediate 2.vii (0.165 g; 0.39 mmol) in THF-MeOH-water (2-2-1; 4 mL) at 0° C. The reaction was gradually warmed to rt and stirred for 3.5 h. After evaporation under reduced pressure, the residue was diluted with water (5 mL), acidified to pH 3 with 10% aq. $NaHSO_4$. The resulting white precipitate was filtered, washed with water and dried to a constant weight. The title acid was obtained as a white solid (0.122 g; 79% yield).

$^1$H NMR ($d_6$-DMSO) δ: 8.42 (s, 1H); 8.22 (d, J=8.4 Hz, 1H); 7.94 (d, J=1.7 Hz, 1H); 7.88 (dd, J=1.7, 8.3 Hz, 1H); 7.80-7.85 (m, 2H); 7.42-7.57 (m, 3H); 3.99-4.26 (m, 2H); 3.16 (s, 3H); 2.45-2.67 (overlapped m, 1H); 2.19-2.33 (m, 1H); 1.61 (s, 3H).

MS (ESI, m/z): 401.2 [M+H$^+$] for $C_{20}H_{20}N_2O_5S$; $t_R$=0.75 min.

2.ix. (RS)-2-methyl-2-(methylsulfonyl)-4-(4-oxo-7-phenylquinazolin-3(4H)-yl)-N-((tetrahydro-2H-pyran-2-yl)oxy)butanamide Starting from intermediate 2.viii (0.121 g; 0.303 mmol) and proceeding in analogy to Preparation B, step B.iv, the title product was obtained as a colourless gum (0.152 g; quant.).

$^1$H NMR ($d_6$-DMSO) δ (mixture of diastereoisomers): 11.42 (br. s, 1H); 8.39 (s, 0.5H); 8.36 (s, 0.5H); 8.23 (d, J=8.3 Hz, 1H); 7.94 (d, J=1.7 Hz, 1H); 7.88 (dd, J=1.7, 8.3 Hz, 1H); 7.80-7.85 (m, 2H); 7.42-7.58 (m, 3H); 4.94-4.97 (m, 0.5H); 4.91-4.94 (m, 0.5H); 3.83-4.25 (m, 3H); 3.45-3.59 (m, 1H); 3.10 (s, 1.5H); 3.07 (m, 1.5H); 2.40-2.68 (overlapped m, 1H); 2.18-2.31 (m, 1H); 1.63 (s, 1.5H); 1.62 (s, 1.5H); 1.60-1.72 (overlapped m, 3H); 1.48-1.59 (m, 3H).

MS (ESI, m/z): 500.4 [M+H$^+$] for $C_{25}H_{29}N_3O_6S$, $t_R$=0.83 min.

2.x. (R)-N-hydroxy-2-methyl-2-(methylsulfonyl)-4-(4-oxo-7-phenylquinazolin-3(4H)-yl)butanamide Starting from intermediate 2.ix (0.152 g; 0.305 mmol) and proceeding in analogy to Procedure D, the racemic mixture was obtained as a white solid (0.104 g). The products were separated by semi-preparative chiral HPLC Method A (Hept-MeOH-EtOH-TFA 1-2-2-0.04; flow rate: 24 mL/min, UV detection at 258 nm), the respective retention times (flow rate: 1.2 mL/min) were 13.4 and 18.9 min. The title enantiomer was identified as the first-eluting enantiomer and was obtained as an orange foam (0.045 g).

$^1$H NMR ($d_6$-DMSO) δ: 10.99 (br. s, 1H); 8.38 (s, 1H); 8.21 (d, J=8.3 Hz, 1H); 7.93 (d, J=1.7 Hz, 1H); 7.87 (dd, J=1.7, 8.3 Hz, 1H); 7.79-7.84 (m, 2H); 7.40-7.56 (m, 3H); 4.06-4.22 (m, 1H); 3.81-3.97 (m, 1H); 3.08 (s, 3H); 2.43-2.65 (overlapped m, 1H); 2.13-2.29 (m, 1H); 1.60 (s, 3H).

MS (ESI, m/z): 416.1 [M+H$^+$] for $C_{20}H_{21}N_3O_5S$; $t_R$=0.69 min.

Example 3

(R)-N-hydroxy-4-(7-(((1S,2S)-2-(hydroxymethyl)cyclopropyl)buta-1,3-diyn-1-yl)-4-oxoquinazolin-3(4H)-yl)-2-methyl-2-(methylsulfonyl)butanamide 3.i. ((1S,2S)-2-((3-((3R)-3-methyl-3-(methylsulfonyl)-4-oxo-4-(((tetrahydro-2H-pyran-2-yl)oxy)amino)butyl)-4-oxo-3,4-dihydroquinazolin-7-yl)buta-1,3-diyn-1-yl)cyclopropyl)methyl acetate To a solution of $nBuNH_2$ (30% in water; 2.6 mL) was added at rt, CuCl (0.022 g; 0.22 mmol) and $NH_2OH.HCl$ (0.25 g; 3.34 mmol). The compound of Preparation H (0.7 g; 1.6 mmol) was added and the mixture was immediately cooled to 0° C. The compound of Preparation I ((S,S)-enantiomer; 0.482 g, 1.85 mmol) was added and the reaction proceeded at rt overnight. The mixture was diluted with water (10 mL) and extracted with EA (4×20 mL). The combined org. layers were dried over $MgSO_4$ and concentrated under reduced pressure to afford the crude title compound as a greenish gum (1.22 g).

MS (ESI, m/z): 583.9 [M+H$^+$] for $C_{29}H_{33}N_3O_8S$; $t_R$=0.89 min.

3.ii. (2R)-4-(7-(((1S,2S)-2-(hydroxymethyl)cyclopropyl)buta-1,3-diyn-1-yl)-4-oxoquinazolin-3(4H)-yl)-2-methyl-2-(methylsulfonyl)-N-((tetrahydro-2H-pyran-2-yl)oxy)butanamide Intermediate 3.i (1.22 g; 1.6 mmol) was dissolved in MeOH (6 mL). $K_2CO_3$ (0.5 g; 3.5 mmol) was added in one portion. The reaction mixture was stirred for 5 h. Water (5 mL) was added and the aq. mixture was extracted once with EA (60 mL) then with EA-MeOH (9-1; 4×20 mL). The org. phase was dried over $MgSO_4$, filtered and evaporated under reduced pressure. The crude was purified by CC (DCM-MeOH) to afford a yellow oil (0.80 g; 94% yield).

MS (ESI, m/z): 542.0 [M+H$^+$] for $C_{27}H_{31}N_3O_7S$; $t_R$=0.78 min.

3.iii. (R)-N-hydroxy-4-(7-(((1S,2S)-2-(hydroxymethyl)cyclopropyl)buta-1,3-diyn-1-yl)-4-oxoquinazolin-3(4H)-yl)-2-methyl-2-(methylsulfonyl)butanamide Starting from intermediate 3.ii (0.114 g; 0.210 mmol) and proceeding in analogy to Procedure D, the title product was obtained, after precipitation in water and trituration in Et$_2$O, as a white solid (0.331 g; 56% yield).

$^1$H NMR (d$_6$-DMSO) δ: 11.00 (br. s, 1H); 9.23 (br. s, 1H); 8.38 (s, 1H); 8.12 (d, J=8.3 Hz, 1H); 7.80 (s, 1H); 7.61 (d, J=8.3 Hz, 1H); 4.72 (t, J=5.7 Hz, 1H); 4.06-4.15 (m, 1H); 3.83-3.92 (m, 1H); 3.41-3.47 (m, 1H); 3.23-3.29 (m, 1H); 3.08 (s, 3H); 2.47-2.61 (overlapped m, 1H); 2.13-2.22 (m, 1H); 1.59 (s, 3H); 1.43-1.53 (m, 2H); 0.94-0.99 (m, 1H); 0.88-0.93 (m, 1H).

MS (ESI, m/z): 458.0 [M+H$^+$] for $C_{22}H_{23}N_3O_6S$; $t_R$=0.66 min.

Example 4

(R)-N-hydroxy-4-(7-((3-hydroxyoxetan-3-yl)buta-1,3-diyn-1-yl)-4-oxoquinazolin-3(4H)-yl)-2-methyl-2-(methylsulfonyl)butanamide Starting from the compound of Preparation H (0.131 g; 0.292 mmol) and the compound of Preparation J (0.068 g; 0.303 mmol) and proceeding in analogy to Procedure G (93% yield) and Procedure B (24% yield), the title compound was obtained, after purification by prep-HPLC (Method 1), as a white solid (0.030 g).

$^1$H NMR (d$_6$-DMSO) δ: 10.98 (s, 1H); 9.21 (s, 1H); 8.40 (s, 1H); 8.16 (d, J=8.3 Hz, 1H); 7.90 (s, 1H); 7.68 (d, J=8.3 Hz, 1H); 6.83 (s, 1H); 4.74 (d, J=6.2 Hz, 2H); 4.57 (d, J=6.2 Hz, 2H); 4.06-4.18 (m, 1H); 3.82-3.95 (m, 1H); 3.08 (s, 3H); 2.43-2.65 (overlapped m, 1H); 2.13-2.25 (m, 1H); 1.60 (s, 3H).

MS (ESI, m/z): 459.9 [M+H$^+$] for $C_{21}H_{21}N_3O_7S$; $t_R$=0.61 min.

Example 5

(R)-N-hydroxy-4-(7-(((1R,2R)-2-(hydroxymethyl)cyclopropyl)buta-1,3-diyn-1-yl)-4-oxoquinazolin-3(4H)-yl)-2-methyl-2-(methylsulfonyl)butanamide Starting from the compound of Preparation H (0.110 g; 0.246 mmol) and the compound of Preparation I ((R,R)-enantiomer; 0.059 g; 0.271 mmol) and proceeding successively in analogy to Example 3, steps 3.i and 3.ii and Procedure B, the title compound was obtained, after purification by prep-HPLC (Method 1), as a yellow solid (0.020 g; 16% yield over 3 steps).

$^1$H NMR (d$_6$-DMSO) δ: 10.99 (s, 1H); 9.23 (s, 1H); 8.38 (s, 1H); 8.12 (d, J=8.3 Hz, 1H); 7.80 (d, J=1.4 Hz, 1H); 7.61 (dd, J=1.4, 8.3 Hz, 1H); 4.72 (br. s, 1H); 4.06-4.17 (m, 1H); 3.82-3.93 (m, 1H); 3.41-3.46 (m, 1H); 3.24-3.29 (m, 1H); 3.08 (s, 3H); 2.45-2.61 (overlapped m, 1H); 2.14-2.21 (m, 1H); 1.59 (s, 3H); 1.43-1.52 (m, 2H); 0.95-0.99 (m, 1H); 0.88-0.93 (m, 1H).

MS (ESI, m/z): 458.0 [M+H$^+$] for $C_{22}H_{23}N_3O_6S$; $t_R$=0.66 min.

Example 6

(R)-N-hydroxy-4-(7-((1-(hydroxymethyl)cyclopropyl)buta-1,3-diyn-1-yl)-4-oxoquinazolin-3(4H)-yl)-2-methyl-2-(methylsulfonyl)butanamide

6.i. (R)-4-(7-((1-(((tert-butyldiphenylsilyl)oxy)methyl)cyclopropyl)buta-1,3-diyn-1-yl)-4-oxoquinazolin-3(4H)-yl)-2-methyl-2-(methylsulfonyl)-N-((tetrahydro-2H-pyran-2-yl)oxy)butanamide Starting from the compound of Preparation H (0.134 g; 0.300 mmol) and the compound of Preparation K (0.130 g; 0.314 mmol) and proceeding in analogy to Example 3, step 3.i, the title compound was obtained, after purification by CC (DCM-MeOH), as a yellow oil (0.182 g; 78% yield).

MS (ESI, m/z): 780.0 [M+H$^+$] for $C_{43}H_{49}N_3O_7SSi$; $t_R$=1.13 min.

6.ii. (R)-4-(7-((1-(hydroxymethyl)cyclopropyl)buta-1,3-diyn-1-yl)-4-oxoquinazolin-3(4H)-yl)-2-methyl-2-(methylsulfonyl)-N-((tetrahydro-2H-pyran-2-yl)oxy)butanamide To a solution of intermediate 6.i (0.180 g; 0.230 mmol) in THF (0.46 mL) was added TBAF (1M in THF; 0.48 mL). The reaction procedeed at rt for 1 h. Then, TBAF (0.24 mL) was added and the reaction was stirred at rt for 1 h. The reaction mixture was concentrated in vacuo and the residue was purified by CC (DCM-MeOH) to give the title compound as a yellowish oil (0.097 g; 77% yield).

$^1$H NMR (d$_6$-DMSO) δ: 11.43 (s, 0.5H); 11.41 (s, 0.5H); 8.38 (s, 0.5H); 8.36 (s, 0.5H); 8.12 (d, J=8.2 Hz, 1H); 7.81 (d, J=1.4 Hz, 1H); 7.61-7.64 (m, 1H); 5.07 (t, J=6.1 Hz, 1H); 4.92-4.94 (m, 0.5H); 4.88-4.91 (m, 0.5H); 3.98-4.16 (m, 2H); 3.83-3.95 (m, 1H); 3.47-3.54 (m, 1H); 3.40 (d, J=6.1 Hz, 2H); 3.08 (s, 1.5H); 3.06 (s, 1.5H); 2.46-2.68 (overlapped m, 1H); 2.14-2.27 (m, 1H); 1.61 (s, 1.5H); 1.60 (s, 1.5H); 1.59-1.70 (overlapped m, 3H); 1.49-1.58 (m, 3H); 0.96-1.00 (m, 2H); 0.90-0.93 (m, 2H).

MS (ESI, m/z): 542.0 [M+H$^+$] for $C_{27}H_{31}N_3O_7S$; $t_R$=0.78 min.

6.iii. (R)-N-hydroxy-4-(7-((1-(hydroxymethyl)cyclopropyl)buta-1,3-diyn-1-yl)-4-oxoquinazolin-3(4H)-yl)-2-methyl-2-(methylsulfonyl)butanamide Starting from intermediate 6.ii (0.097 g; 0.179 mmol) and proceeding in analogy to Procedure B, the title compound was obtained, after purification by prep-HPLC (Method 1) and trituration in Et$_2$O, as a white solid (0.029 g; 35% yield).

$^1$H NMR (d$_6$-DMSO) δ: 10.99 (s, 1H); 9.23 (s, 1H); 8.38 (s, 1H); 8.12 (d, J=8.2 Hz, 1H); 7.81 (s, 1H); 7.62 (d, J=8.2 Hz, 1H); 5.07 (s, 1H); 4.07-4.14 (m, 1H); 3.83-3.91 (m, 1H); 3.40 (s, 2H); 3.08 (s, 3H); 2.47-2.61 (overlapped m, 1H); 2.14-2.22 (m, 1H); 1.59 (s, 3H); 0.96-0.99 (m, 2H); 0.90-0.93 (m, 2H).

MS (ESI, m/z): 457.9 [M+H$^+$] for $C_{22}H_{23}N_3O_6S$; $t_R$=0.66 min.

Example 7

(R)-4-(7-(5-amino-5-methylhexa-1,3-diyn-1-yl)-4-oxoquinazolin-3(4H)-yl)-N-hydroxy-2-methyl-2-(methylsulfonyl)butanamide formate Starting from the compound of Preparation H (0.150 g; 0.334 mmol) and the compound of Preparation L (0.104 g; 0.336 mmol) and proceeding successively in analogy to Example 3, step 3.i (77% yield) and Procedure B (10% yield), the title compound was obtained, after purification by prep-HPLC (Method 1), as a yellow solid (0.013 g).

$^1$H NMR (d$_6$-DMSO) δ: 11.00 (br. s, 1H); 9.22 (br. s, 1H); 8.41 (s, 1H); 8.16 (d, J=8.3 Hz, 1H); 8.13 (s, 1H); 7.91 (d, J=1.4 Hz, 1H); 7.68 (dd, J=1.4, 8.3 Hz, 1H); 4.07-4.15 (m, 1H); 3.85-3.93 (m, 1H); 3.08 (s, 3H); 2.46-2.61 (overlapped m, 1H); 2.13-2.23 (m, 1H); 1.60 (s, 3H); 1.59 (s, 6H).

MS (ESI, m/z): 485.9 [M+CH$_3$CN$^+$] for C$_{22}$H$_{26}$N$_4$O$_7$S; t$_R$=0.51 min.

Example 8

(R)-N-hydroxy-4-(7-((4-(2-hydroxyethyl)phenyl)ethynyl)-4-oxoquinazolin-3(4H)-yl)-2-methyl-2-(methylsulfonyl)butanamide Starting from the compound of Preparation H (0.151 g; 0.337 mmol) and 2-(4-iodophenyl)ethan-1-ol (0.085 g; 0.35 mmol; commercial), and proceeding successively in analogy to Procedure F (81% yield) and Procedure D (28% yield), the title compound was obtained, after purification by prep-HPLC (Method 1), as an orange solid (0.037 g).

$^1$H NMR (d$_6$-DMSO) δ: 11.01 (br. s, 1H); 9.25 (br. s, 1H); 8.39 (s, 1H); 8.16 (d, J=8.2 Hz, 1H); 7.81 (d, J=1.4 Hz, 1H); 7.66 (dd, J=1.4, 8.2 Hz, 1H); 7.54 (d, J=8.2 Hz, 2H); 7.32 (d, J=8.2 Hz, 2H); 4.66-4.71 (m, 1H); 4.08-4.18 (m, 1H); 3.84-3.95 (m, 1H); 3.61-3.65 (m, 2H); 3.09 (s, 3H); 2.77 (t, J=6.8 Hz, 2H); 2.47-2.62 (overlapped m, 1H); 2.15-2.24 (m, 1H); 1.60 (s, 3H).

MS (ESI, m/z): 484.0 [M+H$^+$] for C$_{24}$H$_{25}$N$_3$O$_6$S, t$_R$=0.68 min.

Example 9

(R)-4-(6-fluoro-7-(((1S,2S)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation M (0.252 g, 0.540 mmol) and the compound of Preparation I ((S,S)-enantiomer; 0.117 g; 0.540 mmol), and proceeding successively in analogy to Example 3, step 3.i (53% yield) and Procedure D (17% yield), the title compound was obtained, after precipitation in water, as an orange solid (0.023 g).

$^1$H NMR (d$_6$-DMSO) δ: 10.99 (s, 1H); 9.22 (s, 1H); 8.37 (s, 1H); 7.95 (d, J=6.4 Hz, 1H); 7.90 (d, J=9.1 Hz, 1H); 4.73 (t, J=5.7 Hz, 1H); 4.06-4.15 (m, 1H); 3.84-3.93 (m, 1H); 3.41-3.48 (m, 1H); 3.24-3.29 (m, 1H); 3.08 (s, 3H); 2.47-2.61 (overlapped m, 1H); 2.13-2.21 (m, 1H); 1.59 (s, 3H); 1.46-1.55 (m, 2H); 0.98-1.03 (m, 1H); 0.90-0.96 (m, 1H).

MS (ESI, m/z): 475.9 [M+H$^+$] for C$_{22}$H$_{22}$N$_3$O$_6$FS; t$_R$=0.68 min.

Example 10

(R)-4-(7-((R)-5,6-dihydroxyhexa-1,3-diyn-1-yl)-4-oxoquinazolin-3(4H)-yl)-N-hydroxy-2-methyl-2-(methylsulfonyl)butanamide Starting from the compound of Preparation H (0.199 g; 0.446 mmol) and the compound of Preparation Q (0.103 g; 0.454 mmol), and proceeding successively in analogy to Example 3, step 3.i (56% yield) and Procedure D (45% yield), the title compound was obtained, after precipitation in water, as a dark yellow solid (0.051 g).

$^1$H NMR (d$_6$-DMSO) δ: 10.99 (s, 1H); 9.23 (s, 1H); 8.39 (s, 1H); 8.13 (d, J=8.2 Hz, 1H); 7.83 (s, 1H); 7.64 (d, J=8.2 Hz, 1H); 5.08 (d, J=4.9 Hz, 1H); 4.72 (t, J=5.2 Hz, 1H); 4.06-4.15 (m, 1H); 3.82-3.91 (m, 1H); 3.61-3.67 (m, 1H); 3.29-3.41 (overlapped m, 2H); 3.08 (s, 3H); 2.43-2.67 (overlapped m, 3H); 2.13-2.21 (m, 1H); 1.59 (s, 3H).

MS (ESI, m/z): 463.0 [M+H$^+$] for C$_{21}$H$_{23}$N$_3$O$_7$S; t$_R$=0.56 min.

Example 11

(R)-4-(6-fluoro-7-(((1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation M (0.251 g; 0.539 mmol) and the compound of Preparation I ((R,R)-enantiomer; 0.119 g; 0.548 mmol), and proceeding successively in analogy to Example 3, step 3.i (61% yield) and Procedure D (49% yield), the title compound was obtained, after precipitation in water and then EtOH, as a brown solid (0.077 g).

$^1$H NMR (d$_6$-DMSO) δ: 10.99 (d, J=1.8 Hz, 1H); 9.22 (d, J=1.8 Hz, 1H); 8.37 (s, 1H); 7.95 (d, J=6.4 Hz, 1H); 7.90 (d, J=9.1 Hz, 1H); 4.73 (t, J=5.7 Hz, 1H); 4.06-4.14 (m, 1H); 3.84-3.93 (m, 1H); 3.41-3.48 (m, 1H); 3.24-3.30 (m, 1H); 3.08 (s, 3H); 2.46-2.61 (overlapped m, 1H); 2.13-2.21 (m, 1H); 1.59 (s, 3H); 1.46-1.55 (m, 2H); 0.98-1.02 (m, 1H); 0.90-0.95 (m, 1H).

MS (ESI, m/z): 476.0 [M+H$^+$] for C$_{22}$H$_{22}$N$_3$O$_6$FS; t$_R$=0.68 min.

Example 12

(R)-4-(6-fluoro-7-((1-(hydroxymethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation M (0.150 g; 0.323 mmol) and the compound of Preparation K (0.134 g; 0.323 mmol), and proceeding successively in analogy to Example 3, step 3.i (43% yield), Example 6, step 6.ii (70% yield) and Procedure D (47% yield), the title compound was obtained, after precipitation in water, as a white solid (0.022 g).

$^1$H NMR (d$_6$-DMSO) δ: 10.99 (d, J=1.8 Hz, 1H); 9.22 (d, J=1.8 Hz, 1H); 8.37 (s, 1H); 7.96 (d, J=6.4 Hz, 1H); 7.90 (d, J=9.1 Hz, 1H); 5.09 (t, J=5.9 Hz, 1H); 4.06-4.14 (m, 1H); 3.84-3.92 (m, 1H); 3.41 (d, J=5.9 Hz, 2H); 3.08 (s, 3H); 2.47-2.61 (overlapped m, 1H); 2.13-2.21 (m, 1H); 1.59 (s, 3H); 0.99-1.03 (m, 2H); 0.91-0.95 (m, 2H).

MS (ESI, m/z): 475.9 [M+H$^+$] for C$_{22}$H$_{22}$N$_3$O$_6$FS; t$_R$=0.69 min.

Example 13

(R)-N-hydroxy-4-(7-((3-(hydroxymethyl)bicyclo[1.1.1]pentan-1-yl)buta-1,3-diyn-1-yl)-4-oxoquinazolin-3(4H)-yl)-2-methyl-2-(methylsulfonyl)butanamide Starting from the compound of Preparation H (0.104 g; 0.232 mmol) and the compound of Preparation N (0.102 g; 0.233 mmol), and proceeding successively in analogy to Example 3, step 3.i (53% yield), Example 6, step 6.ii (68% yield) and Procedure D (66% yield), the title compound was obtained, after precipitation in water, as a white solid (0.027 g).

$^1$H NMR (d$_6$-DMSO) δ: 10.99 (s, 1H); 9.23 (s, 1H); 8.39 (s, 1H); 8.13 (d, J=8.3 Hz, 1H); 7.83 (d, J=1.3 Hz, 1H); 7.63 (dd, J=1.3, 8.3 Hz, 1H); 4.59 (t, J=5.6 Hz, 1H); 4.07-4.14 (m, 1H); 3.83-3.91 (m, 1H); 3.35 (d, J=5.6 Hz, 2H); 3.08 (s, 3H); 2.46-2.61 (overlapped m, 1H); 2.13-2.23 (m, 1H); 2.00 (s, 6H); 1.59 (s, 3H).

MS (ESI, m/z): 485.0 [M+H$^+$] for C$_{24}$H$_{25}$N$_3$O$_6$S; t$_R$=0.70 min.

Example 14

(R)-N-hydroxy-4-(7-((4-(2-hydroxyethoxy)phenyl)ethynyl)-4-oxoquinazolin-3(4H)-yl)-2-methyl-2-(methylsulfonyl)butanamide Starting from the compound of Preparation H (0.150 g; 0.336 mmol) and 2-(4-iodophenoxy)ethan-1-ol (0.0896 g; 0.339 mmol), and proceeding successively in analogy to Procedure F (31% yield) and Procedure D (23% yield), the title compound was obtained, after precipitation in water, as a yellow solid (0.012 g).

$^1$H NMR (d$_6$-DMSO) δ: 11.01 (s, 1H); 9.24 (s, 1H); 8.38 (s, 1H); 8.15 (d, J=8.2 Hz, 1H); 7.79 (d, J=1.3 Hz, 1H); 7.64 (dd, J=1.3, 8.2 Hz, 1H); 7.54-7.58 (m, 2H); 7.00-7.04 (m, 2H); 4.90 (t, J=5.6 Hz, 1H); 4.08-4.16 (m, 1H); 4.04 (t, J=4.8 Hz, 2H); 3.83-3.93 (m, 1H); 3.71-3.75 (m, 2H); 3.09 (s, 3H); 2.45-2.65 (overlapped m, 1H); 2.15-2.23 (m, 1H); 1.60 (s, 3H).

MS (ESI, m/z): 500.0 [M+H$^+$] for C$_{24}$H$_{25}$N$_3$O$_7$S; t$_R$=0.67 min.

Example 15

(R)-4-(7-(((1s,3R,4S)-3,4-dihydroxycyclopentyl)buta-1,3-diyn-1-yl)-4-oxoquinazolin-3(4H)-yl)-N-hydroxy-2-methyl-2-(methylsulfonyl)butanamide Starting from the compound of Preparation H (0.198 g; 0.443 mmol) and the compound of Preparation O (0.136 g; 0.553 mmol), and proceeding successively in analogy to Example 3, step 3.i (38% yield) and Procedure B (4% yield), the title compound was obtained, after purification by prep-HPLC (Method 1), as a beige solid (0.004 g).

$^1$H NMR (d$_6$-DMSO) δ: 10.98 (br. s, 1H); 9.26 (br. s, 1H); 8.38 (s, 1H); 8.12 (d, J=8.2 Hz, 1H); 7.82 (s, 1H); 7.62 (d, J=8.2 Hz, 1H); 4.58 (br. s, 2H); 4.07-4.14 (m, 1H); 3.96 (br. s, 2H); 3.83-3.91 (m, 1H); 3.16-3.24 (m, 1H); 3.08 (s, 3H); 2.43-2.61 (overlapped m, 1H); 2.14-2.22 (m, 1H); 1.91-1.99 (m, 2H); 1.76-1.83 (m, 1H); 1.59 (s, 3H).

MS (ESI, m/z): 488.0 [M+H$^+$] for C$_{23}$H$_{25}$N$_3$O$_7$S; t$_R$=0.61 min.

Example 16

(R)-N-hydroxy-4-(7-((4-(1-(hydroxymethyl)cyclopropyl)phenyl)ethynyl)-4-oxoquinazolin-3(4H)-yl)-2-methyl-2-(methylsulfonyl)butanamide:

Starting from the compound of Preparation H (0.152 g; 0.339 mmol) and the compound of Preparation P (0.093 g; 0.339 mmol), and proceeding successively in analogy to Procedure F (58% yield) and Procedure D (31% yield), the title compound was obtained, after purification by prep-HPLC (Method 1), as a yellow solid (0.031 g).

$^1$H NMR (d$_6$-DMSO) δ: 11.01 (s, 1H); 9.24 (s, 1H); 8.39 (s, 1H); 8.16 (d, J=8.3 Hz, 1H); 7.81 (d, J=1.4 Hz, 1H); 7.66 (dd, J=1.4, 8.3 Hz, 1H); 7.53 (d, J=8.4 Hz, 2H); 7.37 (d, J=8.4 Hz, 2H); 4.75 (t, J=5.6 Hz, 1H); 4.08-4.17 (m, 1H); 3.83-3.92 (m, 1H); 3.57 (d, J=5.6 Hz, 2H); 3.09 (s, 3H); 2.47-2.62 (overlapped m, 1H); 2.16-2.23 (m, 1H); 1.60 (s, 3H); 0.88-0.92 (m, 2H); 0.78-0.82 (m, 2H).

MS (ESI, m/z): 510.0 [M+H$^+$] for C$_{26}$H$_{27}$N$_3$O$_6$S; t$_R$=0.72 min.

Example 17

(R)-N-hydroxy-4-(7-(((1S,2R)-2-(hydroxymethyl)-2-methylcyclopropyl)buta-1,3-diyn-1-yl)-4-oxoquinazolin-3(4H)-yl)-2-methyl-2-(methylsulfonyl)butanamide Starting from the compound of Preparation H (0.155 g; 0.347 mmol) and the compound of Preparation R (0.100 g; 0.433 mmol), and proceeding successively in analogy to Example 3, step 3.i (42% yield) and Procedure D (32% yield), the title compound was obtained, after purification by prep-HPLC (Method 1), as a white solid (0.022 g).

$^1$H NMR (d$_6$-DMSO) δ: 11.00 (br. s, 1H); 9.24 (br. s, 1H); 8.38 (s, 1H); 8.12 (d, J=8.3 Hz, 1H); 7.81 (d, J=1.3 Hz, 1H); 7.63 (dd, J=1.3, 8.3 Hz, 1H); 4.77 (t, J=5.8 Hz, 1H); 4.06-4.15 (m, 1H); 3.82-3.91 (m, 1H); 3.28-3.35 (overlapped m, 1H); 3.20-3.25 (dd, J=5.4, 11.2 Hz, 1H); 3.08 (s, 3H); 2.46-2.61 (m, 1H); 2.14-2.21 (m, 1H); 1.62 (dd, J=5.4, 8.7 Hz, 1H); 1.59 (s, 3H); 1.20 (s, 3H); 1.09 (dd, J=3.9, 8.7 Hz, 1H); 0.68-0.71 (m, 1H).

MS (ESI, m/z): 472.0 [M+H$^+$] for C$_{23}$H$_{25}$N$_3$O$_6$S; t$_R$=0.69 min.

Example 18

(R)-4-(7-((4((R)-1,2-dihydroxyethyl)phenyl)ethynyl)-4-oxoquinazolin-3(4H)-yl)-N-hydroxy-2-methyl-2-(methylsulfonyl)butanamide:

Starting from the compound of Preparation H (0.147 g; 0.328 mmol) and (R) -1-(4-iodophenyl)ethane-1,2-diol (0.087 g; 0.33 mmol; commercial), and proceeding successively in analogy to Procedure F (52% yield) and Procedure D (64% yield), the title compound was obtained, after precipitation in water, as a brown solid (0.055 g).

$^1$H NMR (d$_6$-DMSO) δ: 11.01 (s, 1H); 9.24 (s, 1H); 8.39 (s, 1H); 8.17 (d, J=8.2 Hz, 1H); 7.82 (s, 1H); 7.67 (dd, J=1.5, 8.2 Hz, 1H); 7.57 (d, J=8.2 Hz, 2H); 7.43 (d, J=8.2 Hz, 2H); 5.37 (br. s, 1H); 4.77 (br. s, 1H); 4.58 (t, J=5.7 Hz, 1H); 4.09-4.16 (m, 1H); 3.83-3.94 (m, 1H); 3.41-3.50 (m, 2H); 3.09 (s, 3H); 2.47-2.67 (overlapped m, 1H); 2.16-2.25 (m, 1H); 1.60 (s, 3H).

MS (ESI, m/z): 500.00 [M+H⁻] for C₂₄H₂₅N₃O₇S; t_R=0.59 min.

Example 19

(2R)-4-(7-((1-((RS)-1,2-dihydroxyethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation H (0.157 g; 0.351 mmol) and the compound of Preparation T (0.094 g; 0.383 mmol), and proceeding successively in analogy to Example 3, step 3.i (75% yield) and Procedure B (18% yield), the compound was obtained, after purification by prep-HPLC (Method 1), as a yellow solid (0.023 g).

¹H NMR (d₆-DMSO) δ: 10.99 (br. s, 1H); 9.22 (br. s, 1H); 8.38 (s, 1H); 8.12 (d, J=8.4 Hz, 1H); 7.81 (d, J=1.3 Hz, 1H); 7.62 (dd, J=1.5, 8.2 Hz, 1H); 5.09 (d, J=4.6 Hz, 1H); 4.63 (t, J=5.7 Hz, 1H); 4.06-4.15 (m, 1H); 3.82-3.92 (m, 1H); 3.55-3.62 (m, 1H); 3.39-3.48 (m, 1H); 3.05-3.12 (overlapped m, 1H); 3.08 (s, 3H); 2.47-2.60 (overlapped m, 1H); 2.13-2.24 (m, 1H); 1.59 (s, 3H); 0.89-1.03 (m, 4H).

MS (ESI, m/z): 488.0 [M+H⁺] for C₂₃H₂₅N₃O₇S; t_R=0.60 min.

Example 20

(R)-N-hydroxy-4-(7-(((1R,2R)-2-(hydroxymethyl)-1-methylcyclopropyl)buta-1,3-diyn-1-yl)-4-oxoquinazolin-3(4H)-yl)-2-methyl-2-(methylsulfonyl)butanamide Starting from the compound of Preparation H (0.189 g; 0.423 mmol) and the compound of Preparation U (0.192 g; 0.448 mmol), and proceeding successively in analogy to Example 3, step 3.i (69% yield), Example 6, step 6.ii (87% yield) and Procedure D (12% yield), the title compound was obtained, after purification by prep-HPLC (Method 1), as an off-white solid (0.015 g).

¹H NMR (d₆-DMSO) δ: 10.99 (s, 1H); 9.23 (s, 1H); 8.38 (s, 1H); 8.12 (d, J=8.3 Hz, 1H); 7.81 (d, J=1.2 Hz, 1H); 7.61 (dd, J=1.2, 8.3 Hz, 1H); 4.70 (t, J=5.4 Hz, 1H); 4.05-4.18 (m, 1H); 3.82-3.94 (m, 1H); 3.59-3.67 (m, 1H); 3.23-3.36 (overlapped m, 1H); 3.08 (s, 3H); 2.45-2.61 (overlapped m, 1H); 2.13-2.24 (m, 1H); 1.59 (s, 3H); 1.43-1.52 (m, 1H); 1.32 (s, 3H); 1.15 (dd, J=4.4, 9.3 Hz, 1H); 0.67 (dd, J=4.7, 6.7 Hz, 1H).

MS (ESI, m/z): 472.0 [M+H⁺] for C₂₃H₂₅N₃O₆S; t_R=0.69 min.

Example 21

(R)-4-(8-fluoro-7-(((1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation V (0.203 g; 0.436 mmol) and the compound of Preparation I ((R,R)-enantiomer; 0.113 g; 0.518 mmol), and proceeding successively in analogy to Example 3, step 3.i (48% yield) and Procedure D (23% yield), the title compound was obtained, after purification by prep-HPLC (Method 1), as a beige solid (0.023 g).

¹H NMR (d₆-DMSO) δ: 10.98 (br. s, 1H); 9.26 (br. s, 1H); 8.44 (s, 1H); 7.92 (d, J=8.4 Hz, 1H); 7.64 (dd, J=6.3, 8.4 Hz, 1H); 4.73 (br. s, 1H); 4.05-4.19 (m, 1H); 3.86-3.95 (m, 1H); 3.42-3.47 (m, 1H); 3.24-3.39 (overlapped m, 1H); 3.08 (s, 3H); 2.43-2.69 (overlapped m, 1H); 2.13-2.26 (m, 1H); 1.59 (s, 3H); 1.45-1.55 (m, 2H); 0.97-1.04 (m, 1H); 0.89-0.96 (m, 1H).

MS (ESI, m/z): 476.0 [M+H⁺] for C₂₂H₂₂N₃O₆FS; t_R=0.67 min.

Example 22

(R)-(1-(4-(3-(4-(hydroxyamino)-3-methyl-3-(methylsulfonyl)-4-oxobutyl)-4-oxo-3,4-dihydroquinazolin-7-yl)ethynyl)phenyl)cyclopropyl)methyl dimethylglycinate hydrochloride Starting from the compound of Preparation H (0.306 g; 0.683 mmol) and the compound of Preparation W (0.245 g; 0.682 mmol), and proceeding successively in analogy to Procedure F (56% yield) and Procedure D (21% yield), the title product was obtained, after purification by prep-HPLC (Method 1), as a yellow solid (0.050 g).

¹H NMR (d₆-DMSO) δ: 11.01 (br. s, 1H); 10.14 (br. s, 1H); 8.41 (s, 1H); 8.17 (d, J=8.3 Hz, 1H); 7.82 (d, J=1.3 Hz, 1H); 7.66 (dd, J=1.3, 8.3 Hz, 1H); 7.56 (d, J=8.4 Hz, 2H); 7.40 (d, J=8.4 Hz, 2H); 4.39 (s, 2H); 3.82-4.29 (overlapped m, 2H); 4.19 (d, J=3.4 Hz, 2H); 3.09 (s, 3H); 2.80 (d, J=2.8 Hz, 6H); 2.42-2.67 (overlapped m, 1H); 2.14-2.25 (m, 1H); 1.60 (s, 3H); 1.07-1.11 (m, 2H); 1.00-1.04 (m, 2H).

MS (ESI, m/z): 595.0 [M+H⁺] for C₃₀H₃₅N₄O₇ClS; t_R=0.65 min.

Example 23

(R)-4-(8-fluoro-7-(((1S,2S)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation V (0.250 g; 0.537 mmol) and the compound of Preparation I ((S,S)-enantiomer; 0.135 g; 0.623 mmol), and proceeding successively in analogy to Example 3, step 3.i (35% yield) and Procedure D (20% yield), the title compound was obtained, after purification by CC (DCM-MeOH), as a yellow solid (0.018 g).

¹H NMR (d₆-DMSO) δ: 10.99 (br. s, 1H); 9.22 (s, 1H); 8.44 (s, 1H); 7.92 (d, J=8.3 Hz, 1H); 7.65 (dd, J=6.2, 8.3 Hz, 1H); 4.73 (t, J=5.7 Hz, 1H); 4.07-4.15 (m, 1H); 3.86-3.94 (m, 1H); 3.41-3.49 (m, 1H); 3.24-3.37 (overlapped m, 1H); 3.08 (s, 3H); 2.44-2.65 (overlapped m, 1H); 2.13-2.22 (m, 1H); 1.59 (s, 3H); 1.46-1.55 (m, 2H); 0.98-1.04 (m, 1H); 0.89-0.96 (m, 1H).

MS (ESI, m/z): 476.0 [M+H⁺] for C₂₂H₂₂N₃O₆FS; t_R=0.67 min.

Example 24

(R)-N-hydroxy-4-(7-(((1R,2S)-2-(hydroxymethyl)-2-methylcyclopropyl)buta-1,3-diyn-1-yl)-4-oxoquinazolin-3(4H)-yl)-2-methyl-2-(methylsulfonyl)butanamide Starting from the compound of Preparation H (0.152 g; 0.339 mmol) and the compound of Preparation X (0.081 g; 0.351 mmol), and proceeding successively in analogy to Example 3, step 3.i (64% yield) and Procedure D (35% yield), the title compound was obtained, after purification by prep-HPLC (Method 1), as a white solid (0.040 g).

¹H NMR (d₆-DMSO) δ: 10.99 (br. s, 1H); 9.23 (s, 1H); 8.38 (s, 1H); 8.11 (d, J=8.2 Hz, 1H); 7.81 (d, J=1.3 Hz, 1H); 7.63 (dd, J=1.6, 8.2 Hz, 1H); 4.77 (t, J=5.8 Hz, 1H); 4.04-4.15 (m, 1H); 3.81-3.93 (m, 1H); 3.29-3.34 (overlapped m, 1H); 3.23 (dd, J=5.6, 11.3 Hz, 1H); 3.08 (s, 3H); 2.48-2.61 (overlapped m, 1H); 2.13-2.22 (m, 1H); 1.62 (dd, J=5.3, 8.7 Hz, 1H); 1.59 (s, 3H); 1.20 (s, 3H); 1.06-1.12 (m, 1H); 0.67-0.72 (m, 1H).

MS (ESI, m/z): 472.0 [M+H⁺] for $C_{23}H_{25}N_3O_6S$; $t_R$=0.69 min.

Example 25

(R)-4-(7-((1-aminocyclopropyl)buta-1,3-diyn-1-yl)-4-oxoquinazolin-3(4H)-yl)-N-hydroxy-2-methyl-2-(methylsulfonyl)butanamide formate Starting from the compound of Preparation H (0.150 g; 0.336 mmol) and the compound of Preparation Y (0.103 g; 0.337 mmol), and proceeding successively in analogy to Procedure F (37% yield) and Procedure B (21% yield), the title compound was obtained, after purification by prep-HPLC (Method 2), as an orange solid (0.013 g).

¹H NMR (d₆-DMSO) δ: 11.00 (br. s, 1H); 9.24 (br. s, 1H); 8.41 (s, 1H); 8.15 (d, J=8.2 Hz, 1H); 8.13 (s, 1H); 7.87 (d, J=1.4 Hz, 1H); 7.66 (dd, J=1.4, 8.2 Hz, 1H); 4.08-4.17 (m, 1H); 3.84-3.94 (m, 1H); 3.09 (s, 3H); 2.47-2.62 (overlapped m, 1H); 2.12-2.24 (m, 1H); 1.60 (s, 3H); 1.26-1.32 (m, 2H); 1.19-1.24 (m, 2H).

MS (ESI, m/z): 442.9 [M+H⁺] for $C_{22}H_{24}N_4O_7S$; $t_R$=0.50 min.

Example 26

(R)-4-(7-(((1R,2R)-2-((S)-1,2-dihydroxyethyl)cyclopropyl)buta-1,3-diyn-1-yl)-4-oxoquinazolin-3(4H)-yl)-N-hydroxy-2-methyl-2-(methylsulfonyl)butanamide Starting from the compound of Preparation H (0.157 g; 0.351 mmol) and the compound of Preparation Z (0.178 g: 0.363 mmol), and proceeding successively in analogy to Example 3, step 3.i (57% yield) and Procedure B (14% yield), the title compound was obtained, after purification by prep-HPLC (Method 2), as a white solid (0.014 g).

¹H NMR (d₆-DMSO) δ: 10.99 (br. s, 1H); 9.23 (s, 1H); 8.38 (s, 1H); 8.12 (d, J=8.2 Hz, 1H); 7.80 (d, J=1.4 Hz, 1H); 7.61 (dd, J=1.4, 8.2 Hz, 1H); 4.72 (d, J=4.0 Hz, 1H); 4.59-4.65 (m, 1H); 4.06-4.15 (m, 1H); 3.82-3.92 (m, 1H); 3.28-3.40 (overlapped m, 3H); 3.08 (s, 3H); 2.46-2.61 (overlapped m, 1H); 2.13-2.22 (m, 1H); 1.59 (s, 3H); 1.53 (m, 1H); 1.39-1.45 (m, 1H); 0.96-1.01 (m, 1H); 0.86-0.91 (m, 1H).

MS (ESI, m/z): 487.9 [M+H⁺] for $C_{23}H_{25}N_3O_7S$; $t_R$=0.60 min.

Example 27

(R)-4-(7-((3-(2-aminoacetamido)cyclopentyl)buta-1,3-diyn-1-yl)-6-fluoro-4-oxoquinazolin-3(4H)-yl)-N-hydroxy-2-methyl-2-(methylsulfonyl)butanamide hydrochloride Starting from the compound of Preparation M (0.231 g; 0.496 mmol) and the compound of Preparation AA (0.195 g; 0.498 mmol), and proceeding successively in analogy to Procedure G (30% yield) and Procedure B (33% yield), the title salt was obtained, after purification by prep-HPLC (Method 2), as a yellow solid (0.028 g; mixture of cis/trans isomers).

¹H NMR (d₆-DMSO) δ: 11.00 (br. s, 1H); 8.53-8.60 (m, 1H); 8.37-8.42 (m, 1H); 8.01-8.08 (m, 3H); 7.98 (d, J=6.4 Hz, 0.5H); 7.97 (d, J=6.4 Hz, 0.5H); 7.91 (d, J=8.9 Hz, 1H); 4.20-4.28 (m, 0.5H); 4.06-4.15 (m, 1.5H); 3.85-3.96 (m, 1H); 3.46-3.57 (m, 2H); 3.12-3.19 (m, 0.5H); 3.08 (s, 3H); 2.99-3.10 (overlapped m, 0.5H); 2.35-2.62 (overlapped m, 1H); 1.77-2.21 (m, 4.5H); 1.65-1.73 (m, 0.5H); 1.46-1.63 (overlapped m, 2H); 1.59 (s, 3H).

MS (ESI, m/z): 546.0 [M+H⁺] for $C_{25}H_{29}N_5O_6ClFS$; $t_R$=0.59 min.

Example 28

(R)-4-(7-(((1R,2R)-2-(aminomethyl)cyclopropyl)buta-1,3-diyn-1-yl)-6-fluoro-4-oxoquinazolin-3(4H)-yl)-N-hydroxy-2-methyl-2-(methylsulfonyl)butanamide hydrochloride Starting from the compound of Preparation M (0.260 g; 0.557 mmol) and the compound of Preparation AB (0.176 g; 0.549 mmol), and proceeding successively in analogy to Procedure G (29% yield) and Procedure B (34% yield), the title compound was obtained, after purification by prep-HPLC (Method 2), as a yellow solid (0.028 g).

¹H NMR (d₆-DMSO) δ: 10.99 (br. s, 1H); 8.39 (s, 1H); 8.05 (br. s, 3H); 7.97 (d, J=6.4 Hz, 1H); 7.91 (d, J=9.1 Hz, 1H); 4.06-4.17 (m, 1H); 3.84-3.98 (m, 1H); 3.08 (s, 3H); 2.84-2.96 (m, 1H); 2.65-2.73 (m, 1H); 2.44-2.61 (overlapped m, 1H); 2.11-2.23 (m, 1H); 1.75-1.82 (m, 1H); 1.53-1.63 (overlapped m, 1H); 1.59 (s, 3H); 1.14-1.19 (m, 1H); 1.04-1.10 (m, 1H).

MS (ESI, m/z): 474.9 [M+H⁺] for $C_{22}H_{24}N_4O_5ClFS$; $t_R$=0.55 min.

Example 29

(R)-4-(6-fluoro-7-(5-hydroxy-5-methylhexa-1,3-diyn-1-yl)-4-oxoquinazolin-3(4H)-yl)-N-hydroxy-2-methyl-2-(methylsulfonyl)butanamide Starting from the compound of Preparation M (0.260 g; 0.557 mmol) and 4-iodo-2-methylbut-3-yn-2-ol (0.119 g; 0.567 mmol; prepared as described in Rajender Reddy et al., *Tetrahedron Lett.* (2010), 51, 2170-2173), and proceeding successively in analogy to Procedure G (48% yield) and Procedure D (39% yield), the title compound was obtained, after purification by CC (DCM-MeOH), as an off-white solid (0.043 g).

¹H NMR (d₆-DMSO) δ: 10.99 (s, 1H); 9.22 (s, 1H); 8.38 (s, 1H); 8.01 (d, J=6.3 Hz, 1H); 7.92 (d, J=9.1 Hz, 1H); 5.78 (s, 1H); 4.06-4.16 (m, 1H); 3.84-3.95 (m, 1H); 3.08 (s, 3H); 2.47-2.61 (overlapped m, 1H); 2.13-2.22 (m, 1H); 1.59 (s, 3H); 1.45 (s, 6H).

MS (ESI, m/z): 465.0 [M+H⁺] for $C_{21}H_{22}N_3O_6FS$; $t_R$=0.68 min.

Example 30

(R)-4-(7-(((1R*,2R*)-1-fluoro-2-(hydroxymethyl) cyclopropyl)buta-1,3-diyn-1-yl)-4-oxoquinazolin-3 (4H)-yl)-N-hydroxy-2-methyl-2-(methylsulfonyl) butanamide Starting from the compound of Preparation H (0.136 g; 0.305 mmol) and the compound of Preparation AC (0.139 g; 0.323 mmol) and proceeding successively in analogy to Example 3, step 3.i (78% yield), Example 6, step 6.ii (72% yield) and Procedure C (59% yield), the title compound was obtained, after precipitation in EtOH, as a yellow solid (0.048 g).

$^1$H NMR ($d_6$-DMSO) δ: 10.99 (s, 1H); 9.23 (d, J=1.3 Hz, 1H); 8.40 (s, 1H); 8.16 (d, J=8.2 Hz, 1H); 7.90 (d, J=0.9 Hz, 1H); 7.69 (dd, J=1.3, 8.2 Hz, 1H); 4.88-4.96 (m, 1H); 4.07-4.15 (m, 1H); 3.84-3.92 (m, 1H); 3.66-3.73 (m, 1H); 3.29-3.41 (overlapped m, 1H); 3.08 (s, 3H); 2.45-2.62 (overlapped m, 1H); 2.14-2.22 (m, 1H); 1.67-1.76 (m, 1H); 1.59 (s, 3H); 1.42-1.49 (m, 1H); 1.27-1.35 (m, 1H).

MS (ESI, m/z): 475.98 [M+H$^+$] for $C_{22}H_{22}N_3O_6FS$; $t_R$=0.67 min.

Example 31

(R)-(1-((3-(4-(hydroxyamino)-3-methyl-3-(methylsulfonyl)-4-oxobutyl)-4-oxo-3,4-dihydroquinazolin-7-yl)buta-1,3-diyn-1-yl)cyclopropyl)methyl dihydrogen phosphate Starting from the compound of Preparation H (0.096 g; 0.215 mmol) and the compound of Preparation AD (0.148 g; 0.402 mmol) and proceeding successively in analogy to Example 3, step 3.i (51% yield) and Procedure B (32% yield), the title compound was obtained, after purification by prep-HPLC (Method 2), as a white solid (0.019 g).

$^1$H NMR ($d_6$-DMSO) δ: 10.99 (br. s, 1H); 9.29 (br. s, 1H); 8.38 (s, 1H); 8.10 (d, J=8.3 Hz, 1H); 7.81 (d, J=1.4 Hz, 1H); 7.62 (dd, J=1.5, 8.2 Hz, 1H); 7.17 (br. s, 2H); 4.05-4.16 (m, 1H); 3.84-3.93 (m, 1H); 3.68 (d, J=5.9 Hz, 2H); 3.08 (s, 3H); 2.47-2.60 (overlapped m, 1H); 2.13-2.22 (m, 1H); 1.59 (s, 3H); 1.01-1.08 (m, 4H).

MS (ESI, m/z): 538.93 [M+H$^+$] for $C_{22}H_{24}N_3O_9PS$; $t_R$=0.57 min.

Example 32

(R)-4-(7-(5-(dimethylamino)penta-1,3-diyn-1-yl)-6-fluoro-4-oxoquinazolin-3(4H)-yl)-N-hydroxy-2-methyl-2-(methylsulfonyl)butanamide formate Starting from the compound of Preparation M (0.204 g; 0.438 mmol) and 3-iodo-N,N-dimethylprop-2-yn-1-amine (0.097 g; 0.465 mmol, prepared as described in Crossley and Browne, *J. Org. Chem.* (2010), 75, 5414-5416), and proceeding successively in analogy to Procedure G (67% yield) and Procedure B (12% yield), the title compound was obtained, after purification by prep-HPLC (Method 2), as a yellow solid (0.015 g).

$^1$H NMR ($d_6$-DMSO) δ: 10.99 (s, 1H); 9.22 (s, 1H); 8.40 (s, 1H); 8.13 (s, 1H); 8.08 (d, J=6.3 Hz, 1H); 7.95 (d, J=9.1 Hz, 1H); 4.27 (s, 2H); 4.07-4.17 (m, 1H); 3.86-3.96 (m, 1H); 3.08 (s, 3H); 2.76 (s, 6H); 2.45-2.62 (overlapped m, 1H); 2.13-2.21 (m, 1H); 1.60 (s, 3H).

MS (ESI, m/z): 463.0 [M+H$^+$] for $C_{21}H_{23}N_4O_5FS$; $t_R$=0.51 min.

Example 33

(R)-4-(7-(((1R*,2R*)-2-fluoro-2-(hydroxymethyl) cyclopropyl)buta-1,3-diyn-1-yl)-4-oxoquinazolin-3 (4H)-yl)-N-hydroxy-2-methyl-2-(methylsulfonyl) butanamide Starting from the compound of Preparation H (0.100 g; 0.178 mmol) and the compound of Preparation AE (0.078 g; 0.332 mmol), and proceeding successively in analogy to Example 3, step 3.i (77% yield) and Procedure B (23% yield), the title compound was obtained, after purification by prep-HPLC (Method 2), as a beige solid (0.019 g).

$^1$H NMR ($d_6$-DMSO) δ: 11.03 (br.s, 1H); 9.23 (br. s, 1H); 8.39 (s, 1H); 8.14 (d, J=6.8 Hz, 1H); 7.84 (d, J=1.3 Hz, 1H); 7.64 (dd, J=1.3, 8.2 Hz, 1H); 5.23-5.30 (m, 1H); 4.07-4.18 (m, 1H); 3.83-3.94 (m, 1H); 3.59-3.77 (overlapped m, 2H); 3.08 (s, 3H); 2.47-2.61 (overlapped m, 1H); 2.14-2.22 (m, 1H); 1.99-2.05 (m, 1H); 1.59 (s, 3H); 1.36-1.47 (m, 2H).

MS (ESI, m/z): 476.96 [M+H$^+$] for $C_{22}H_{22}N_3O_6FS$; $t_R$=0.66 min.

Example 34

(R)-4-(6-fluoro-7-((1-(hydroxymethyl)cyclobutyl) buta-1,3-diyn-1-yl)-4-oxoquinazolin-3(4H)-yl)-N-hydroxy-2-methyl-2-(methylsulfonyl)butanamide Starting from the compound of Preparation M (0.151 g; 0.323 mmol) and the compound of Preparation AF (0.138 g; 0.323 mmol) and proceeding successively in analogy to Example 3, step 3.i (38% yield), Example 6, step 6.ii (57% yield) and Procedure C (32% yield), the title compound was obtained, after precipitation in EtOH, as a white solid (0.011 g).

$^1$H NMR ($d_6$-DMSO) δ: 10.99 (s, 1H); 9.22 (s, 1H); 8.38 (s, 1H); 7.98 (d, J=6.3 Hz, 1H); 7.91 (d, J=9.0 Hz, 1H); 5.24 (t, J=5.7 Hz, 1H); 4.06-4.15 (m, 1H); 3.84-3.93 (m, 1H); 3.53 (d, J=5.7 Hz, 2H); 3.08 (s, 3H); 2.45-2.61 (overlapped m, 1H); 2.11-2.23 (m, 5H); 1.88-2.03 (m, 2H); 1.59 (s, 3H).

MS (ESI, m/z): 490.0 [M+H$^+$] for $C_{23}H_{24}N_3O_6FS$; $t_R$=0.73 min.

Example 35

(R)-4-(6-fluoro-7-(5-(3-hydroxyoxetan-3-yl)penta-1, 3-diyn-1-yl)-4-oxoquinazolin-3(4H)-yl)-N-hydroxy-2-methyl-2-(methylsulfonyl)butanamide Starting from the compound of Preparation M (0.102 g; 0.219 mmol) and the compound of Preparation AG (0.103 g; 0.433 mmol) and proceeding successively in analogy to Example 3, step 3.i (87% yield) and Procedure D (11% yield), the title compound was obtained, after purification by CC (DCM-MeOH) and by prep-HPLC (Method 2), as a white solid (0.010 g).

$^1$H NMR ($d_6$-DMSO) δ: 10.82 (br. s, 1H); 9.30 (br. s, 1H); 8.38 (s, 1H); 8.00 (d, J=5.9 Hz, 1H); 7.91 (d, J=8.9 Hz, 1H); 6.14 (s, 1H); 4.38-4.50 (m, 4H); 4.10 (m, 1H); 3.89 (m, 1H); 3.08 (s, 3H); 2.94 (s, 2H); 2.44-2.65 (overlapped m, 1H); 2.17 (m, 1H); 1.59 (s, 3H).

MS (ESI, m/z): 492.0 [M+H$^+$] for $C_{22}H_{22}N_3O_7FS$; $t_R$=0.63 min.

The racemic mixtures of Reference Examples 1 to 12 can be separated into their enantiomers using, for example, chiral HPLC. Thus the following further invention compounds or salts would be obtained:

(R)-4-(7-(2-fluoro-4-(3-morpholinopropoxy)phenyl)-4-oxoquinazolin-3(4H)-yl)-N-hydroxy-2-methyl-2-(methylsulfonyl)butanamide;

(R)-N-hydroxy-2-methyl-2-(methylsulfonyl)-4-(7-(4-(3-morpholinopropoxy)phenyl)-4-oxoquinazolin-3(4H)-yl)butanamide;

(R)-4-(7-(2-fluoro-4-(2-morpholinoethoxy)phenyl)-4-oxoquinazolin-3(4H)-yl)-N-hydroxy-2-methyl-2-(methylsulfonyl)butanamide;

(R)-4-(7-(2-fluoro-3-methoxyphenyl)-4-oxoquinazolin-3(4H)-yl)-N-hydroxy-2-methyl-2-(methylsulfonyl)butanamide;

(R)-4-(7-(3-fluoro-4-methoxyphenyl)-4-oxoquinazolin-3(4H)-yl)-N-hydroxy-2-methyl-2-(methylsulfonyl)butanamide;

(R)-4-(7-(4-(dimethylamino)phenyl)-4-oxoquinazolin-3(4H)-yl)-N-hydroxy-2-methyl-2-(methylsulfonyl)butanamide;

(R)-N-hydroxy-4-(7-(4-(hydroxymethyl)phenyl)-4-oxoquinazolin-3(4H)-yl)-2-methyl-2-(methylsulfonyl)butanamide;

(R)-N-hydroxy-2-methyl-2-(methylsulfonyl)-4-(7-(4-(morpholinomethyl)phenyl)-4-oxoquinazolin-3(4H)-yl)butanamide;

(R)-4-(6-fluoro-4-oxo-7-phenylquinazolin-3(4H)-yl)-N-hydroxy-2-methyl-2-methylsulfonyl)butanamide;

(R)-N-hydroxy-4-(7-((4-(hydroxymethyl)phenyl)ethynyl)-4-oxoquinazolin-3(4H)-yl)-2-methyl-2-(methylsulfonyl)butanamide;

(R)-N-hydroxy-4-(7-((4-(3-hydroxyoxetan-3-yl)phenyl)ethynyl)-4-oxoquinazolin-3(4H)-yl)-2-methyl-2-(methylsulfonyl)butanamide; and (R)-N-hydroxy-2-methyl-2-(methylsulfonyl)-4-(7-((4-(morpholinomethyl)phenyl)ethynyl)-4-oxoquinazolin-3(4H)-yl)butanamide.

Pharmacological Properties of the Invention Compounds

In Vitro Assays

Bacterial Growth Minimal Inhibitory Concentrations:

Experimental Methods:

Minimal Inhibitory Concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, 7$^{th}$ ed., Clinical and Laboratory Standards Institute (CLSI) Document M7-A7, Wayne, Pa., U.S.A. (2006).

Results:

All Example compounds were tested against several Gram-positive and Gram-negative bacteria. Typical antibacterial test results are given in Table 1 hereafter (MICs in mg/L). *K. pneumoniae* A-651 is a multiply-resistant strain (in particular quinolone-resistant), while *E. coli* ATCC25922 and *P. aeruginosa* ATCC27853 are quinolone-sensitive strains.

TABLE 1

| Example No. | MIC for *E. coli* ATCC25922 | MIC for *P. aeruginosa* ATCC27853 | MIC for *K. Pneumoniae* A-651 |
|---|---|---|---|
| RE1 | 1 | 16 | 2 |
| RE2 | 1 | 8 | 2 |
| RE3 | 2 | 16 | 4 |
| RE4 | 0.125 | 8 | ≤0.063 |
| RE5 | 0.25 | 16 | 1 |
| RE6 | 0.125 | 16 | 0.125 |
| RE7 | 2 | 16 | 8 |
| RE8 | 1 | 16 | 2 |
| RE9 | 0.25 | 16 | ≤0.063 |
| RE10 | 0.25 | 16 | 1 |
| RE11 | 1 | 8 | 1 |
| RE12 | 0.5 | 16 | 0.5 |
| 1 | ≤0.063 | 4 | 0.25 |
| 2 | 0.25 | 8 | ≤0.063 |
| 3 | 0.125 | 1 | 0.5 |
| 4 | 4 | 4 | 4 |
| 5 | ≤0.063 | 1 | 0.25 |
| 6 | 0.25 | 2 | 1 |
| 7 | 1 | 2 | 4 |
| 8 | 0.125 | 4 | 0.25 |
| 9 | 0.125 | 1 | 0.25 |
| 10 | 8 | 4 | 8 |
| 11 | ≤0.063 | 1 | 0.25 |
| 12 | 0.25 | 2 | 0.5 |
| 13 | 0.125 | .5 | 0.25 |
| 14 | 0.25 | 16 | 0.5 |
| 15 | 1 | 2 | 1 |
| 16 | 0.125 | 4 | 0.25 |
| 17 | ≤0.063 | 0.5 | 0.125 |
| 18 | 0.5 | 4 | 2 |
| 19 | 8 | 8 | 32 |
| 20 | 0.125 | 1 | 0.5 |
| 21 | 0.25 | 4 | 0.5 |
| 22 | 0.5 | 16 | 4 |
| 23 | 0.5 | 4 | 0.5 |
| 24 | 0.25 | 1 | 0.25 |
| 25 | 0.25 | 1 | 0.5 |
| 26 | 1 | 1 | 1 |
| 27 | 1 | 8 | 4 |
| 28 | 8 | 8 | 8 |
| 29 | 1 | 2 | 1 |
| 30 | 0.25 | 1 | 0.5 |
| 32 | 0.25 | 2 | 0.5 |
| 33 | 0.25 | 0.5 | 0.5 |
| 34 | 0.25 | 2 | 1 |
| 35 | 4 | 4 | 4 |
| Cipro | 0.5 | >32 | >32 |

The compound of Example 31 was tested against wild-type *E. coli* A-1261 in the absence of alkaline phosphatase, in the presence of an alkaline phosphatase and in the presence of an esterase. The corresponding antibacterial test results are given in Table 2 hereafter (MICs in mg/L).

TABLE 2

| | MIC for *E. coli* A-1261 | | |
|---|---|---|---|
| Example No. | In the absence of alkaline phosphatase or esterase | In the presence of an alkaline phosphatase (2 i.U./mL) | In the presence of an esterase (10 i.U./mL) |
| 31 | >16 | 0.5 | >16 |

The invention claimed is:

1. A compound of formula I

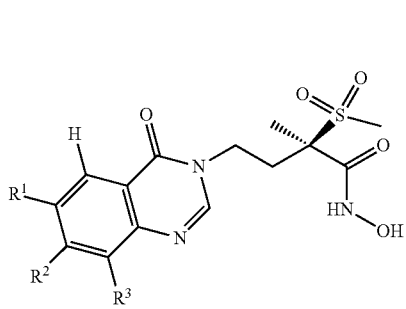

wherein
R¹ is H or halogen;
R² is the group M;
R³ is H or halogen;
M is one of the groups $M^A$ and $M^B$ represented below

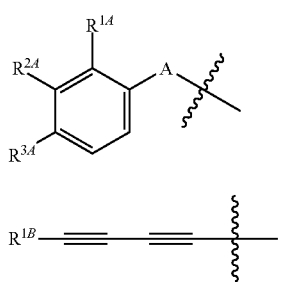

wherein A represents a bond or C.C;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy $(C_1-C_4)$alkyl, 1,2-dihydroxyethyl, di$(C_1-C_3)$alkylamino, 1-hydroxymethyl-cycloprop-1-yl, 1-((dimethylglycyl)oxy)methyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, [di$(C_1-C_3)$alkylamino]-$(C_1-C_3)$alkyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy($C_1-C_3$)alkyl)oxetan-3-yl, 3-hydroxythietan-3-yl, trans-(cis-3,4-dihydroxy)-cyclopent-1-yl, 3-(2-aminoacetamido)cyclopentyl, 3-hydroxymethylbicyclo[1,1,1]pentan-1-yl or 3-hydroxyoxetan-3-ylmethyl;
or a salt thereof.

2. The compound of formula I according to claim 1, which is a compound of formula $I_{CE}$

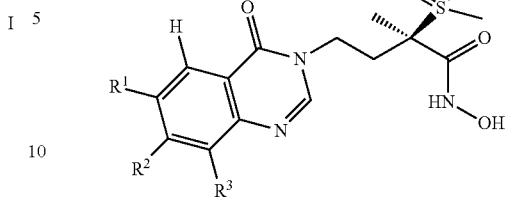

wherein
R¹ is H or halogen;
R² is the group M;
R³ is H or halogen;
M is one of the groups $M^A$ and $M^B$ represented below

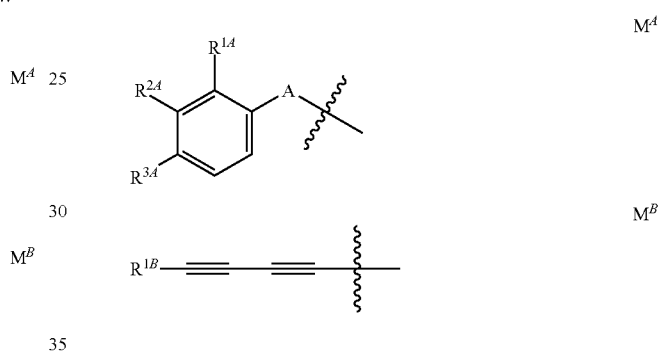

wherein A represents a bond or C.C;
$R^{1A}$ is H or halogen;
$R^{2A}$ is H, $(C_1-C_3)$alkoxy or halogen;
$R^{3A}$ is H, $(C_1-C_3)$alkoxy, hydroxy$(C_2-C_4)$alkoxy, hydroxy $(C_1-C_4)$alkyl, 1,2-dihydroxyethyl, di$(C_1-C_3)$alkylamino, 1-hydroxymethyl-cycloprop-1-yl, 1-((dimethylglycyl)oxy)methyl-cycloprop-1-yl, 3-hydroxyoxetan-3-yl, morpholin-4-yl-$(C_1-C_2)$alkyl or morpholin-4-yl$(C_2-C_3)$alkoxy; and
$R^{1B}$ is hydroxy$(C_1-C_3)$alkyl, amino$(C_1-C_3)$alkyl, dimethylamino-$(C_1-C_3)$alkyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, trans-(cis-3,4-dihydroxy)-cyclopent-1-yl, 3-(2-aminoacetamido)cyclopentyl, 3-hydroxymethylbicyclo[1,1,1]pentan-1-yl or 3-hydroxyoxetan-3-ylmethyl;
or a salt thereof.

3. The compound of formula I according to claim 1, which is a compound of formula $I_P$ wherein
R¹ is H or halogen;
R² is the group M;
R³ is H or halogen;
M is one of the groups M^A and M^B represented below

M^A

M^B wherein A represents a bond or C.C;
R^{1A} is H or halogen;
R^{2A} is H, (C₁-C₃)alkoxy or halogen;
R^{3A} is H, (C₁-C₃)alkoxy, hydroxy(C₂-C₄)alkoxy, hydroxy (C₁-C₄)alkyl, 1,2-dihydroxyethyl, di(C₁-C₃)alkylamino, 1-hydroxymethyl-cycloprop-1-yl, 1-((dimethylglycyl)oxy)methyl-cycloprop-1-yl, 3-hydroxyoxetan-3-yl, morpholin-4-yl-(C₁-C₂)alkyl or morpholin-4-yl(C₂-C₃)alkoxy; and R^{1B} is hydroxy(C₁-C₃)alkyl, amino(C₁-C₃)alkyl, 1,2-dihydroxyprop-3-yl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 3-hydroxyoxetan-3-yl, 3-(hydroxy(C1-C3)alkyl)oxetan-3-yl, 3-hydroxythietan-3-yl, trans-(cis-3,4-dihydroxy)-cyclopent-1-yl, 3-(2-aminoacetamido)cyclopentyl or 3-hydroxymethylbicyclo[1,1,1]pentan-1-yl;
or a salt thereof.

4. The compound of formula I according to claim 1, wherein R¹ is H or fluorine, R³ is H or fluorine, R^{1A}, when present, is H or fluorine and R^{2A}, when present, is H;
or a salt thereof.

5. The compound of formula I according to claim 1, wherein R¹ is the group M^A;
or a salt thereof.

6. The compound of formula I according to claim 5, wherein A represents a bond;
or a salt thereof.

7. The compound of formula I according to claim 5, wherein A represents C.C;
or a salt thereof.

8. The compound of formula I according to claim 7, wherein R^{1A} is H or fluorine, R^{2A} is H and R^{3A} is hydroxymethyl, 1,2-dihydroxyethyl or 3-hydroxyoxetan-3-yl;
or a salt thereof.

9. The compound of formula I according to claim 1, wherein R² is the group M^B;
or a salt thereof.

10. The compound of formula I according to claim 1, wherein R² is the group M^B and R^{1B} is 1-amino-cycloprop-1-yl, trans-2-hydroxymethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, trans-2-(1,2-dihydroxyethyl)-cycloprop-1-yl, trans-(cis-3,4-dihydroxy)-cyclopent-1-yl or 3-hydroxymethylbicyclo[1,1,1]pentan-1-yl;
or a salt thereof.

11. The compound of formula I according to claim 1, wherein the compound includes:
(R)-4-(7-(2-fluoro-4-methoxyphenyl)-4-oxoquinazolin-3(4H)-yl)-N-hydroxy-2-methyl-2-(methylsulfonyl)butanamide;
(R)-N-hydroxy-2-methyl-2-(methylsulfonyl)-4-(4-oxo-7-phenylquinazolin-3(4H)-yl)butanamide;
(R)-N-hydroxy-4-(7-(((1S,2S)-2-(hydroxymethyl)cyclopropyl)buta-1,3-diyn-1-yl)-4-oxoquinazolin-3(4H)-yl)-2-methyl-2-(methylsulfonyl)butanamide;
(R)-N-hydroxy-4-(7-((3-hydroxyoxetan-3-yl)buta-1,3-diyn-1-yl)-4-oxoquinazolin-3(4H)-yl)-2-methyl-2-(methylsulfonyl)butanamide;
(R)-N-hydroxy-4-(7-(((1R,2R)-2-(hydroxymethyl)cyclopropyl)buta-1,3-diyn-1-yl)-4-oxoquinazolin-3(4H)-yl)-2-methyl-2-(methylsulfonyl)butanamide;
(R)-N-hydroxy-4-(7-((1-(hydroxymethyl)cyclopropyl)buta-1,3-diyn-1-yl)-4-oxoquinazolin-3(4H)-yl)-2-methyl-2-(methylsulfonyl)butanamide;
(R)-4-(7-(5-amino-5-methylhexa-1,3-diyn-1-yl)-4-oxoquinazolin-3(4H)-yl)-N-hydroxy-2-methyl-2-(methylsulfonyl)butanamide;
(R)-N-hydroxy-4-(7-((4-(2-hydroxyethyl)phenyl)ethynyl)-4-oxoquinazolin-3(4H)-yl)-2-methyl-2-(methylsulfonyl)butanamide;
(R)-4-(6-fluoro-7-(((1S,2)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-4-(7-((R)-5,6-dihydroxyhexa-1,3-diyn-1-yl)-4-oxoquinazolin-3(4H)-yl)-N-hydroxy-2-methyl-2-(methylsulfonyl)butanamide;
(R)-4-(6-fluoro-7-(((1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-4-(6-fluoro-7-((1-(hydroxymethyl)cyclopropyl)buta-1,3-diyn-1-yl)-4-oxoquinazolin-3(4H)-yl)-N-hydroxy-2-methyl-2-(methylsulfonyl)butanamide;
(R)-N-hydroxy-4-(7-((3-(hydroxymethyl)bicyclo[1.1.1]pentan-1-yl)buta-1,3-diyn-1-yl)-4-oxoquinazolin-3(4H)-yl)-2-methyl-2-(methylsulfonyl)butanamide;
(R)-N-hydroxy-4-(7-((4-(2-hydroxyethoxy)phenyl)ethynyl)-4-oxoquinazolin-3(4H)-yl)-2-methyl-2-(methylsulfonyl)butanamide;
(R)-4-(7-(((1s,3R,4S)-3,4-dihydroxycyclopentyl)buta-1,3-diyn-1-yl)-4-oxoquinazolin-3(4H)-yl)-N-hydroxy-2-methyl-2-(methylsulfonyl)butanamide;

(R)-N-hydroxy-4-(7-((4-(1-(hydroxymethyl)cyclopropyl)phenyl)ethynyl)-4-oxoquinazolin-3(4H)-yl)-2-methyl-2-(methylsulfonyl)butanamide;

(R)-N-hydroxy-4-(7-(((1S,2R)-2-(hydroxymethyl)-2-methylcyclopropyl)buta-1,3-diyn-1-yl)-4-oxoquinazolin-3(4H)-yl)-2-methyl-2-(methylsulfonyl)butanamide;

(R)-4-(7-((4-((R)-1,2-dihydroxyethyl)phenyl)ethynyl)-4-oxoquinazolin-3(4H)-yl)-N-hydroxy-2-methyl-2-(methylsulfonyl)butanamide;

(2R)-4-(7-((1-(1,2-dihydroxyethyl)cyclopropyl)buta-1,3-diyn-1-yl)-4-oxoquinazolin-3(4H)-yl)-N-hydroxy-2-methyl-2-(methylsulfonyl)butanamide;

(R)-N-hydroxy-4-(7-(((1R,2R)-2-(hydroxymethyl)-1-methylcyclopropyl)buta-1,3-diyn-1-yl)-4-oxoquinazolin-3(4H)-yl)-2-methyl-2-(methylsulfonyl)butanamide;

(R)-4-(8-fluoro-7-(((1R,2R)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-(1-(4-((3-(4-(hydroxyamino)-3-methyl-3-(methylsulfonyl)-4-oxobutyl)-4-oxo-3,4-dihydroquinazolin-7-yl)ethynyl)phenyl)cyclopropyl)methyl dimethylglycinate;

(R)-4-(8-fluoro-7-(((1S,2S)-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-N-hydroxy-4-(7-(((1R,2S)-2-(hydroxymethyl)-2-methylcyclopropyl)buta-1,3-diyn-1-yl)-4-oxoquinazolin-3(4H)-yl)-2-methyl-2-(methylsulfonyl)butanamide;

(R)-4-(7-((1-aminocyclopropyl)buta-1,3-diyn-1-yl)-4-oxoquinazolin-3(4H)-yl)-N-hydroxy-2-methyl-2-(methylsulfonyl)butanamide;

(R)-4-(7-(((1R,2R)-2-((S)-1,2-dihydroxyethyl)cyclopropyl)buta-1,3-diyn- 1-yl)-4-oxoquinazolin-3(4H)-yl)-N-hydroxy-2-methyl-2-(methylsulfonyl)butanamide;

(R)-4-(7-((3-(2-aminoacetamido)cyclopentyl)buta-1,3-diyn-1-yl)-6-fluoro-4-oxoquinazolin-3(4H)-yl)-N-hydroxy-2-methyl-2-(methylsulfonyl)butanamide;

(R)-4-(7-(((1R,2R)-2-(aminomethyl)cyclopropyl)buta-1,3-diyn-1-yl)-6-fluoro-4-oxoquinazolin-3(4H)-yl)-N-hydroxy-2-methyl-2-(methylsulfonyl)butanamide;

(R)-4-(6-fluoro-7-(5-hydroxy-5-methylhexa-1,3-diyn-1-yl)-4-oxoquinazolin-3(4H)-yl)-N-hydroxy-2-methyl-2-(methylsulfonyl)butanamide;

(R)-4-(7-(2-fluoro-4-(3-morpholinopropoxy)phenyl)-4-oxoquinazolin-3(4H)-yl)-N-hydroxy-2-methyl-2-(methylsulfonyl)butanamide;

(R)-N-hydroxy-2-methyl-2-(methylsulfonyl)-4-(7-(4-(3-morpholinopropoxy)phenyl)-4-oxoquinazolin-3(4H)-yl)butanamide;

(R)-4-(7-(2-fluoro-4-(2-morpholinoethoxy)phenyl)-4-oxoquinazolin-3(4H)-yl)-N-hydroxy-2-methyl-2-(methylsulfonyl)butanamide;

(R)-4-(7-(2-fluoro-3-methoxyphenyl)-4-oxoquinazolin-3(4H)-yl)-N-hydroxy-2-methyl-2-(methylsulfonyl)butanamide;

(R)-4-(7-(3-fluoro-4-methoxyphenyl)-4-oxoquinazolin-3(4H)-yl)-N-hydroxy-2-methyl-2-(methylsulfonyl)butanamide;

(R)-4-(7-(4-(dimethylamino)phenyl)-4-oxoquinazolin-3(4H)-yl)-N-hydroxy-2-methyl-2-(methylsulfonyl)butanamide;

(R)-N-hydroxy-4-(7-(4-(hydroxymethyl)phenyl)-4-oxoquinazolin-3(4H)-yl)-2-methyl-2-(methylsulfonyl)butanamide;

(R)-N-hydroxy-2-methyl-2-(methylsulfonyl)-4-(7-(4-(morpholinomethyl)phenyl)-4-oxoquinazolin-3(4H)-yl)butanamide;

(R)-4-(6-fluoro-4-oxo-7-phenylquinazolin-3(4H)-yl)-N-hydroxy-2-methyl-2-methylsulfonyl)butanamide;

(R)-N-hydroxy-4-(7-((4-(hydroxymethyl)phenypethynyl)-4-oxoquinazolin-3(4H)-yl)-2-methyl-2-(methylsulfonyl)butanamide;

(R)-N-hydroxy-4-(7-((4-(3-hydroxyoxetan-3-yl)phenypethynyl)-4-oxoquinazolin-3(4H)-yl)-2-methyl-2-(methylsulfonyl)butanamide;

(R)-N-hydroxy-2-methyl-2-(methylsulfonyl)-4-(7-((4-(morpholinomethyl)phenyethynyl)-4-oxoquinazolin-3(4H)-yl)butanamide;

(R)-4-(7-(((1R*,2R*)-1-fluoro-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-4-(7-(((1R*,2R*)-1-fluoro-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-(1-((3-(4-(hydroxyamino)-3-methyl-3-(methylsulfonyl)-4-oxobutyl)-4-oxo-3,4-dihydroquinazolin-7-yl)buta-1,3-diyn-1-yl)cyclopropyl)methyl dihydrogen phosphate;

(R)-4-(7-(5-(dimethylamino)penta-1,3-diyn-1-yl)-6-fluoro-4-oxoquinazolin-3(4H)-yl)-N-hydroxy-2-methyl-2-(methylsulfonyl)butanamide;

(R)-4-(7-(((1R*,2R*)-2-fluoro-2-(hydroxymethyl)cyclopropyl)buta-1,3-diyn-1-yl)-4-oxoquinazolin-3(4H)-yl)-N-hydroxy-2-methyl-2-(methylsulfonyl)butanamide;

(R)-4-(6-fluoro-7-((1-(hydroxymethyl)cyclobutyl)buta-1,3-diyn-1-yl)-4-oxoquinazolin-3(4H)-yl)-N-hydroxy-2-methyl-2-(methylsulfonyl)butanamide; or (R)-4-(6-fluoro-7-(5-(3-hydroxyoxetan-3-yl)penta-1,3-diyn-1-yl)-4-oxoquinazolin-3(4H)-yl)-N-hydroxy-2-methyl-2-(methylsulfonyl)butanamide;

or a salt thereof.

12. The compound of formula I as defined in claim 1, or a pharmaceutically acceptable salt thereof, formulated as a medicament.

13. A pharmaceutical composition comprising, as active principle, the compound of formula I as defined in claim 1, or a pharmaceutically acceptable salt thereof, and at least one therapeutically inert excipient.

14. A method of preventing or treating a bacterial infection comprising administering a therapeutically effective amount of the compound of formula I as defined in claim 1 to a subject in need thereof.

15. The method according to claim 14, wherein the bacterial infection is Gram-negative bacterial infection.

\* \* \* \* \*